US009624211B2

(12) United States Patent
Zhang et al.

(10) Patent No.: US 9,624,211 B2
(45) Date of Patent: Apr. 18, 2017

(54) ANTI-CANCER COMPOUNDS

(71) Applicant: Board of Regents, The University of Texas System, Austin, TX (US)

(72) Inventors: Shuxing Zhang, Pearland, TX (US); Hui-Kuan Lin, Winston-Salem, NC (US); Chia-Hsin Chan, Houston, TX (US); John Kenneth Morrow, San Diego, CA (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/905,726

(22) PCT Filed: Jul. 18, 2014

(86) PCT No.: PCT/US2014/047216
§ 371 (c)(1),
(2) Date: Jan. 15, 2016

(87) PCT Pub. No.: WO2015/010032
PCT Pub. Date: Jan. 22, 2015

(65) Prior Publication Data
US 2016/0145250 A1     May 26, 2016

Related U.S. Application Data

(60) Provisional application No. 61/847,892, filed on Jul. 18, 2013.

(51) Int. Cl.
C07D 417/14 (2006.01)
A61K 31/454 (2006.01)
A61K 31/428 (2006.01)
A61K 31/5377 (2006.01)
A61K 31/352 (2006.01)
C07D 405/04 (2006.01)
C07D 413/04 (2006.01)
C07D 417/04 (2006.01)
A61K 31/4184 (2006.01)
A61K 31/423 (2006.01)
A61K 31/55 (2006.01)
A61K 45/06 (2006.01)

(52) U.S. Cl.
CPC .......... *C07D 417/14* (2013.01); *A61K 31/352* (2013.01); *A61K 31/4184* (2013.01); *A61K 31/423* (2013.01); *A61K 31/428* (2013.01); *A61K 31/454* (2013.01); *A61K 31/5377* (2013.01); *A61K 31/55* (2013.01); *A61K 45/06* (2013.01); *C07D 405/04* (2013.01); *C07D 413/04* (2013.01); *C07D 417/04* (2013.01)

(58) Field of Classification Search
IPC ................ C07D 417/14; A61K 31/454,31/428, 31/5377
See application file for complete search history.

(56) References Cited

U.S. PATENT DOCUMENTS 8,987,258 B2 * 3/2015 Oalmann ............. A61K 31/353
514/233.5
2009/0149417 A1    6/2009 Ossovskaya et al.

OTHER PUBLICATIONS

Goodman and Gilman (the Pharm. Basis of therapeutics 9th ed. 1225-1232 and 1269-1271.*
Ahad et al., "Development of sulfonamide AKT PH domain inhibitors," *Bioorg. Med. Chem.*, 19:2046-2054, 2011.
Bornstein et al., "Role of the SCFSkp2 ubiquitin ligase in the degradation of p21Cip1 in S phase," *J. Biol. Chem.*, 278:25752-25757, 2003.
Brenke et al., "Fragment-based identification of druggable 'hot spots' of proteins using Fourier domain correlation techniques," *Bioinformatics*, 25(5):621-627, 2009.
Buzzai et al., "The glucose dependence of Akt-transformed cells can be reversed by pharmacologic activation of fatty acid beta-oxidation," *Oncogene*, 24:4165-4173, 2005.
Carrano et al.,"SKP2 is required for ubiquitin-mediated degradation of the CDK inhibitor p27," *Nat. Cell Biol.*, 1:193-199, 1999.
Chan et al., "Deciphering the transcription complex critical for RhoA gene expression and cancer metastasis," *Nat. Cell Biol.*, 12:457-467, 2010.
Chan et al., "Novel ARF/p53-independent senescence pathways in cancer repression," *J. Mol. Med. (Berl)*, 89:857-867, 2011.
Chan et al., "The Skp2-SCF E3 ligase regulates Akt ubiquitination, glycolysis, herceptin sensitivity, and tumorigenesis," *Cell*, 149(5):1098-1111, 2012.
Chen et al., "Targeting the p27 E3 ligase $SCF^{Skp2}$ results in p27- and Skp2-mediated cell-cycle arrest and activation of autophagy," *Blood*, 111:4690-4699, 2008.
Cosconati et al., "Shooting for selective druglike G-quadruplex binders: evidence for telomeric DNA damage and tumor cell death," *J. Med. Chem.*, 55:9785-9792, 2012.
Costa et al., "Action of (2-benzothiazoly1) methyllithium with organic polar functions," *Journal of Heterocyclic Chemistry*, 28:1541-1544, 1991.
Ding and Wang, "Efficient synthesis of isoflavone analogues via a Suzuki coupling reaction," *Tetrahedron Letters*, 46:3707-3709, 2005.
Du-Cuny et al., "Computational modeling of novel inhibitors targeting the Akt pleckstrin homology domain," *Bioorg. Med. Chem.*, 17:6983-6992, 2009.
Elstrom et al., "Akt stimulates aerobic glycolysis in cancer cells," *Cancer Res.*, 64:3892-3899, 2004.
Frasinyuk et al., "Chemistry of the hetero analogs if isoflavones. 22. Mannich reaction in the benzimidazole and benzothiazole analogs of isoflavones," *Chemistry of Heterocyclic Compunds*, 34:923-928, 1998.

(Continued)

*Primary Examiner* — Shirley V Gembeh
(74) *Attorney, Agent, or Firm* — Parker Highlander PLLC

(57) ABSTRACT

Provided are methods and compositions for the treatment of diseases such as cancer. In certain aspects, compounds which can inhibit Skp2 are provided. Specifically chromenone derivatives are disclosed that have the capability toward reducing differentiation of pluripotent, multipotent or totipotent cells and thus have therapeutic utility in the treatment of a proliferative disease such as cancer.

14 Claims, 15 Drawing Sheets

(56) References Cited

OTHER PUBLICATIONS

Frescas and Pagano, "Deregulated proteolysis by the F-box proteins SKP2 and beta-TrCP: tipping the scales of cancer," *Nat. Rev. Cancer*, 8:438-449, 2008.
Gao et al., "Synthesis of daidzin analogues as potential agents for alcohol abuse," *Bioorg Med Chem.*, 11:4069-4081, 2003
Gohlke et al., "Predicting binding modes, binding affinities andhot spots' for protein-ligand complexes using a knowledge-based scoring function," *Perspectives Drug Discov. Design*, 20:115-144, 2000.
Hadj-esfandiari et al., "Synthesis, antibacterial activity, and quantitative structure-activity relationships of new (Z)-2-(nitroimidazolylmethylene)-3(2H)-benzofuranone derivatives," *Bioorg Med Chem Lett*, 17:6354-6363, 2007.
Hao et al., "Structural basis of the Cks1-dependent recognition of p27(Kip1) by the SCF(Skp2) ubiquitin ligase," *Mol Cell*, 20(1):9-19, 2005.
Harmes and DiRenzo, "Cellular quiescence in mammary stem cells and breast tumor stem cells: got testable hypotheses?" *J. Mammary Gland Biol. Neoplasia*, 14:19-27, 2009.
Hershko, "Oncogenic properties and prognostic implications of the ubiquitin ligase Skp2 in cancer," *Cancer*, 112:1415-1424, 2008.
Huang et al., "Searching for new cures for tuberculosis: design, synthesis, and biological evaluation of 2-methylbenzothiazoles," *J Med Chem*, 52:6757-6767, 2009.
Kashiyama et al., "Antitumor benzothiazoles. 8. Synthesis, metabolic formation, and biological properties of the C- and N-oxidation products of antitumor 2-(4-aminophenyl)benzothiazoles," *J Med Chem*, 42:4172-4184, 1999.
Kim et al., "Skp2 regulates Myc protein stability and activity," *Mol. Cell*, 11:1177-1188, 2003.
Koch et al., "Cancer stem cells at the crossroads of current cancer therapy failures—radiation oncology perspective," *Semin. Cancer Biol.*, 20:116-124, 2010.
Lee et al., "Syntheses and radical scavenging activities of resveratrol derivatives," *Bioorg Med Chem Lett*, 14:463-466, 2004.
Li and Tang, "Prostate cancer stem cells and their potential roles in metastasis," *J. Surg. Oncol.*, 103:558-562, 2011.
Lin et al., "Phosphorylation-dependent regulation of the SCF complex formation and Skp2 oncogenic function by Akt/PKB," *Nat. Cell Biol.*, 11:420-432, 2009.
Lin et al., "Skp2 targeting suppresses tumorigenesis by Arf-p53-independent cellular senescence," *Nature*, 464:374-379, 2010.
Liu et al., "NEDD8 modification of CUL 1 dissociates p120(CAND1), an inhibitor of CUL1-SKP1 binding and SCF ligases," *Mol. Cell*, 10:1511-1518, 2002.
Liu et al., "Nitrogen-containing flavonoids as CDK1/Cyclin B inhibitors: design, synthesis, and biological evaluation," *Bioorg Med Chem Lett.*, 17:278-281, 2007.
Mahadevan et al., "Discovery of a novel class of AKT pleckstrin homology domain inhibitors," *Mol. Cancer Ther.*, 7:2621-2632, 2008.
Mandinova and Lee, "The p53 pathway as a target in cancer therapeutics: obstacles and promise," *Sci. Transl. Med.*, 3:64rv1, 2011.
Marian et al., "The effects of telomerase inhibition on prostate tumor-initiating cells," *Int. J. Cancer*, 127:321-331, 2010.
Marian et al., "The telomerase antagonist, imetelstat, efficiently targets glioblastoma tumor-initiating cells leading to decreased proliferation and tumor growth," *Clin. Cancer Res.*, 16:154-163, 2010.
Mathis et al., "Synthesis and evaluation of 11C-labeled 6-substituted 2-arylbenzothiazoles as amyloid imaging agents," *J Med Chem.*, 46:2740-2754, 2003.
Nakayama et al., "Skp2-mediated degradation of p27 regulates progression into mitosis," *Dev. Cell*, 6:661-672, 2004.

Nakayama et al., "Targeted disruption of Skp2 results in accumulation of cyclin E and p27(Kip1), polyploidy and centrosome overduplication," *EMBO J*, 19:2069-2081, 2000.
Nussbaumer et al., "2-Substituted 4-(thio)chromenone 6-O-sulfamates: potent inhibitors of human steroid sulfatase," *J Med Chem.*, 45:4310-4320, 2002.
PCT International Preliminary Report on Patentability issued in International Application No. PCT/US2014/047216, mailed Jan. 19, 2016.
PCT International Search Report and Written Opinion issued in International Application No. PCT/US2014/047216, mailed Oct. 22, 2014.
Robey and Hay, "Is Akt the "Warburg kinase"?-Akt-energy metabolism interactions and oncogenesis," *Semin. Cancer Biol.*, 19:25-31, 2009.
Sakai et al.,"Skp2 controls adipocyte proliferation during the development of obesity," *J. Biol. Chem.*, 282:2038-2046, 2007.
Schulman et al., "Insights into SCF ubiquitin ligases from the structure of the Skp1-Skp2 complex," *Nature*, 408(6810):381-386, 2000.
Soucy et al., "An inhibitor of NEDD8-activating enzyme as a new approach to treat cancer," *Nature*, 458:732-736, 2009.
Tran and Zhang, "Accurate prediction of the bound form of the Akt pleckstrin homology domain using normal mode analysis to explore structural flexibility," *J. Chem. Inf. Model*, 51:2352-2360, 2011.
Tuncbag et al., "HotPoint: hot spot prediction server for protein interfaces," *Nucleic Acids Res.*, 38(Web Server issue):W402-6, 2010.
Vander Heiden et al., "Understanding the Warburg effect: the metabolic requirements of cell proliferation," *Science*, 324:1029-1033, 2009.
Vazquez et al., "The genetics of the p53 pathway, apoptosis and cancer therapy," *Nat. Rev. Drug Discov.*, 7:979-987, 2008.
Velasco-Velazquez et al., "The role of breast cancer stem cells in metastasis and therapeutic implications," *Am. J. Pathol.*, 179:2-11, 2011.
von der Lehr et al., "The F-box protein Skp2 participates in c-Myc proteosomal degradation and acts as a cofactor for c-Myc-regulated transcription," *Mol. Cell*, 11:1189-1200, 2003.
Wang et al.,"Skp2 is required for survival of aberrantly proliferating Rb1-deficient cells and for tumorigenesis in Rbl+/− mice," *Nat. Genet.*, 42:83-88, 2010.
Yadav et al., "3-Formylchromone interacts with cysteine 38 in p65 protein and with cysteine 179 in IκBα kinase, leading to down-regulation of nuclear factor ζB (NF-ζB)-regulated gene products and sensitization of tumor cells," *J. Biol. Chem.*, 287:245-256, 2012.
Yang et al., "The E3 ligase TRAF6 regulates Akt ubiquitination and activation," *Science*, 325:1134-1138, 2009.
Yu et al., "Human CUL-1 associates with the SKP1/SKP2 complex and regulates p21(CIP1/WAF1) and cyclin D proteins," *Proc. Natl. Acad. Sci. USA*, 95:11324-11329, 1998.
Zhang et al., "Antitumor mining 252. Application of validated QSAR models to database mining: discovery of novel tylophorine derivatives as potential anticancer agents," *J. Comput. Aided Mol. Des.*, 21:97-112, 2007.
Zhang et al., "Glycine decarboxylase activity drives non-small cell lung cancer tumor-initiating cells and tumorigenesis," *Cell*, 148:259-272, 2012.
Zhang, "Computer-aided drug discovery and development," *Methods Mol. Biol.*, 716:23-38, 2011.
Zheng et al., "CAND1 binds to unneddylated CUL1 and regulates the formation of SCF ubiquitin E3 ligase complex," *Mol. Cell*, 10:1519-1526, 2002.
Zheng et al., "Structure of the Cul1-Rbx1-Skp1-F boxSkp2 SCF ubiquitin ligase complex," *Nature*, 416:703-709, 2002.

\* cited by examiner

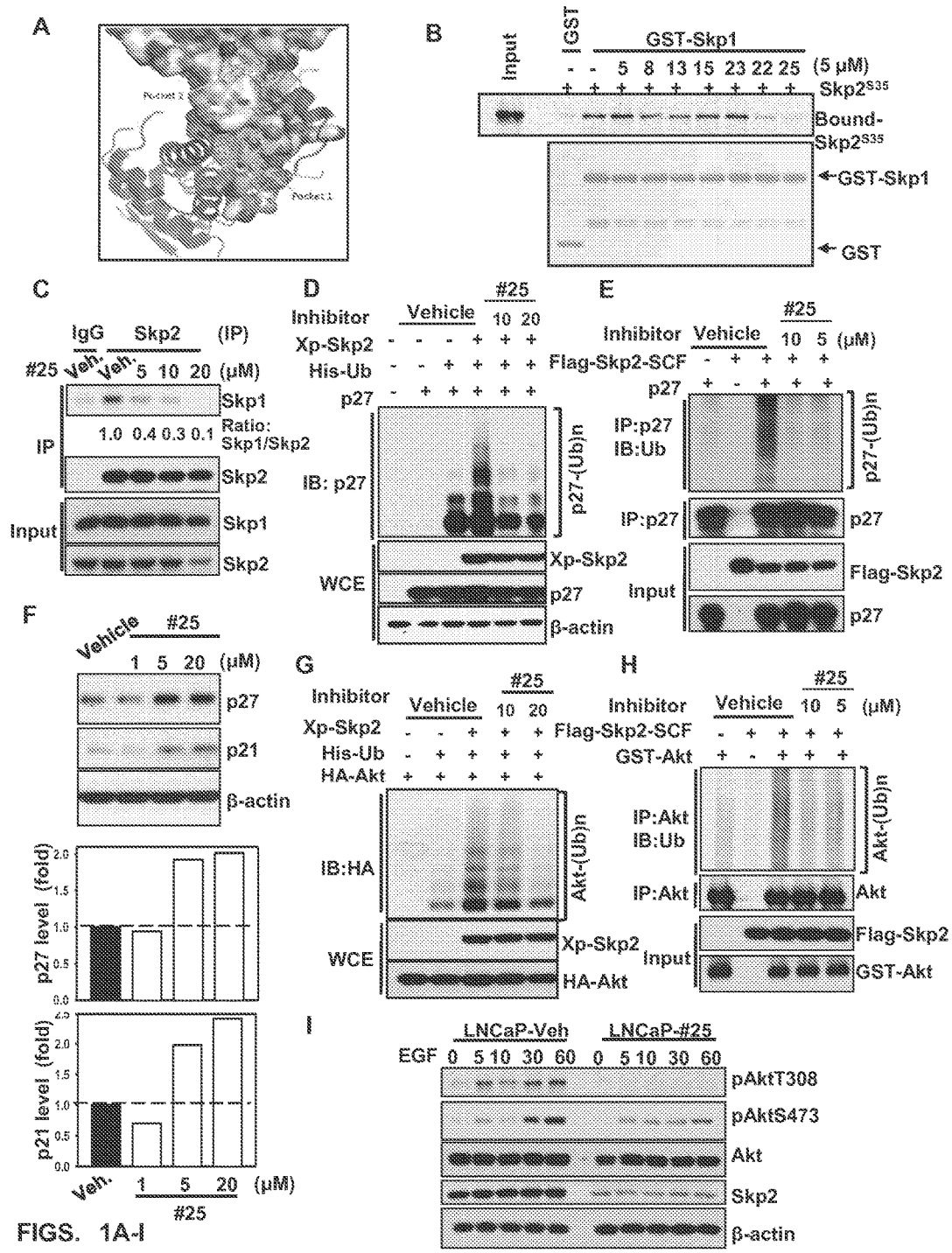
FIGS. 1A-I

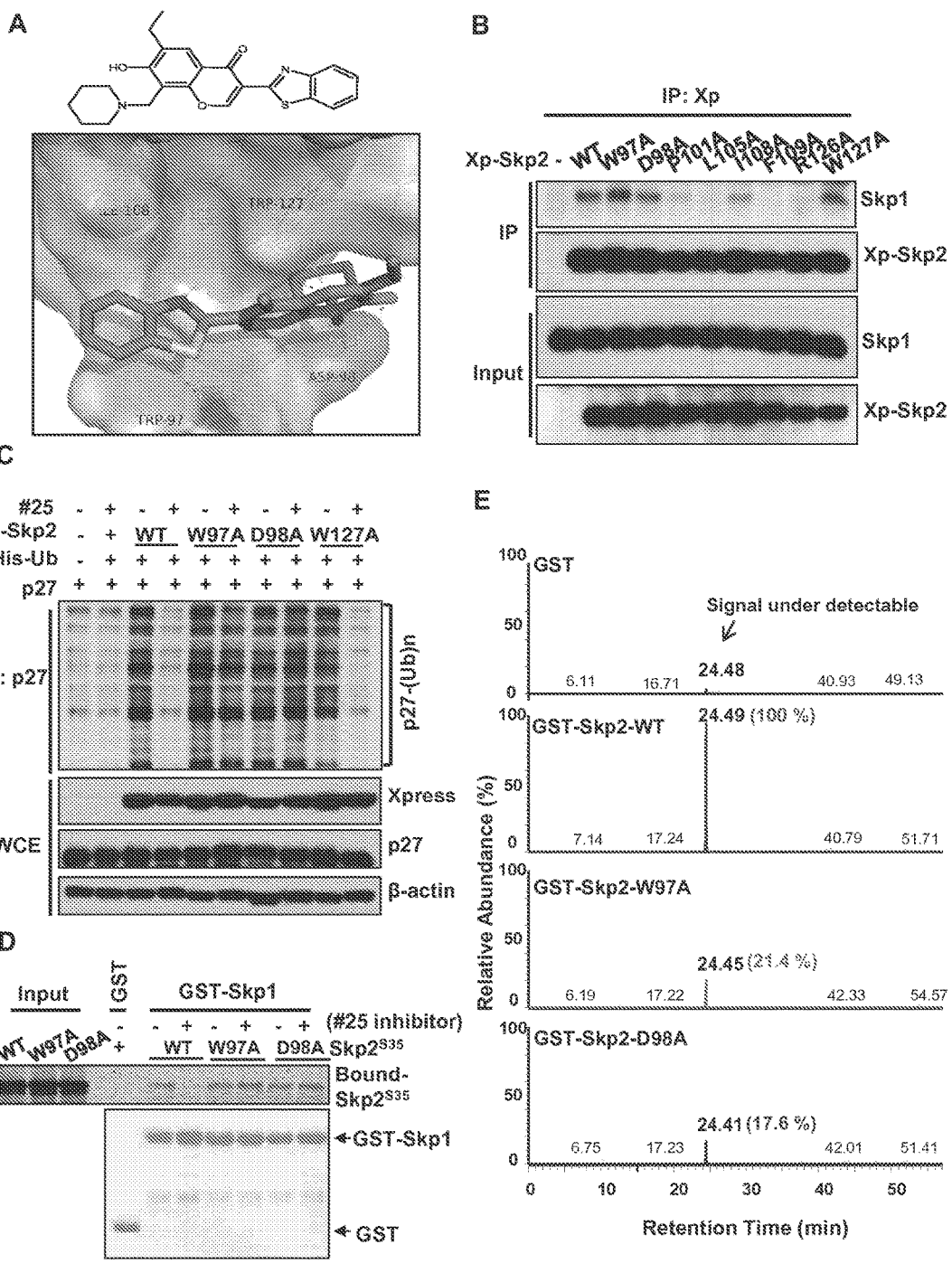
FIGS. 2A-E

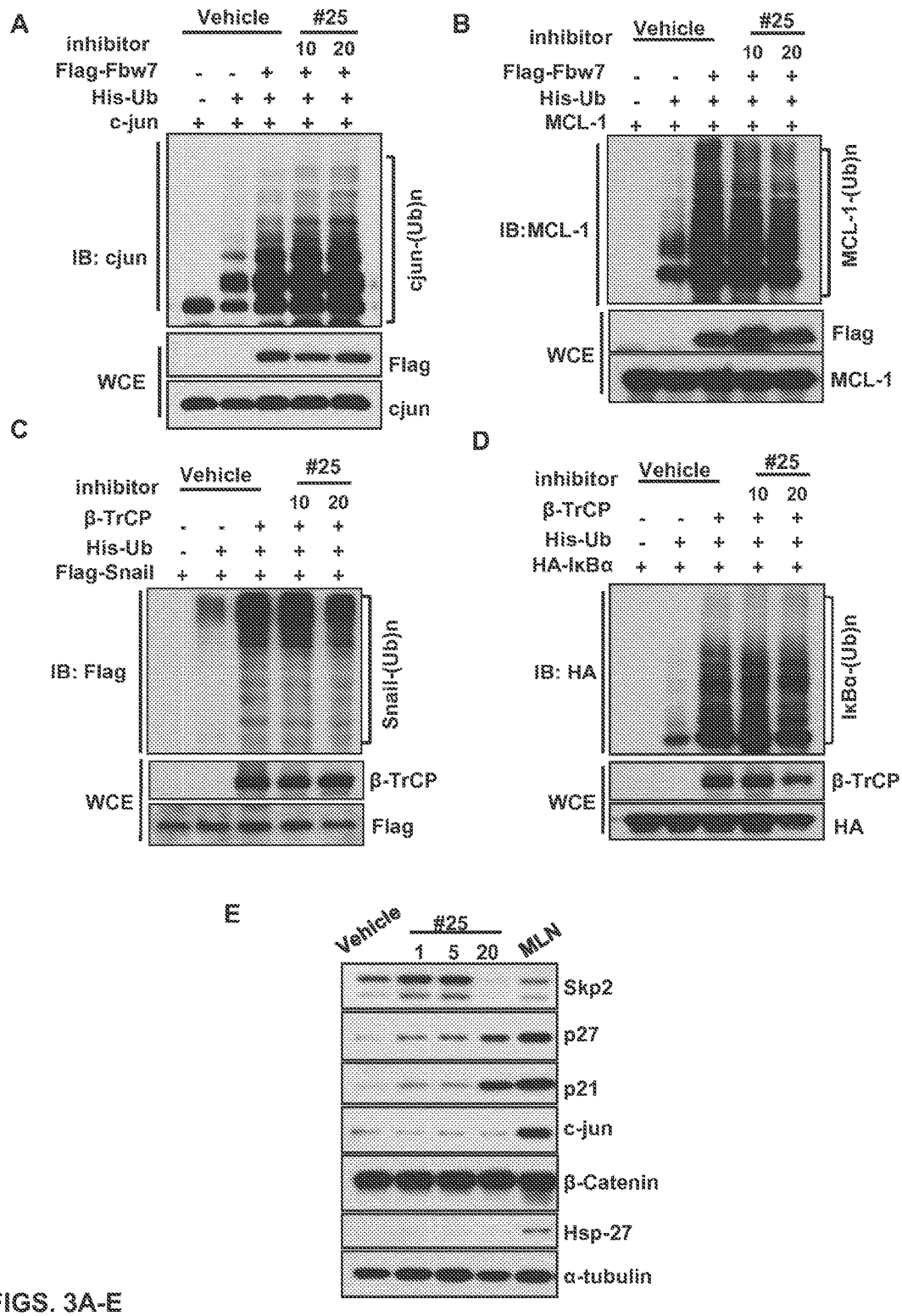
FIGS. 3A-E

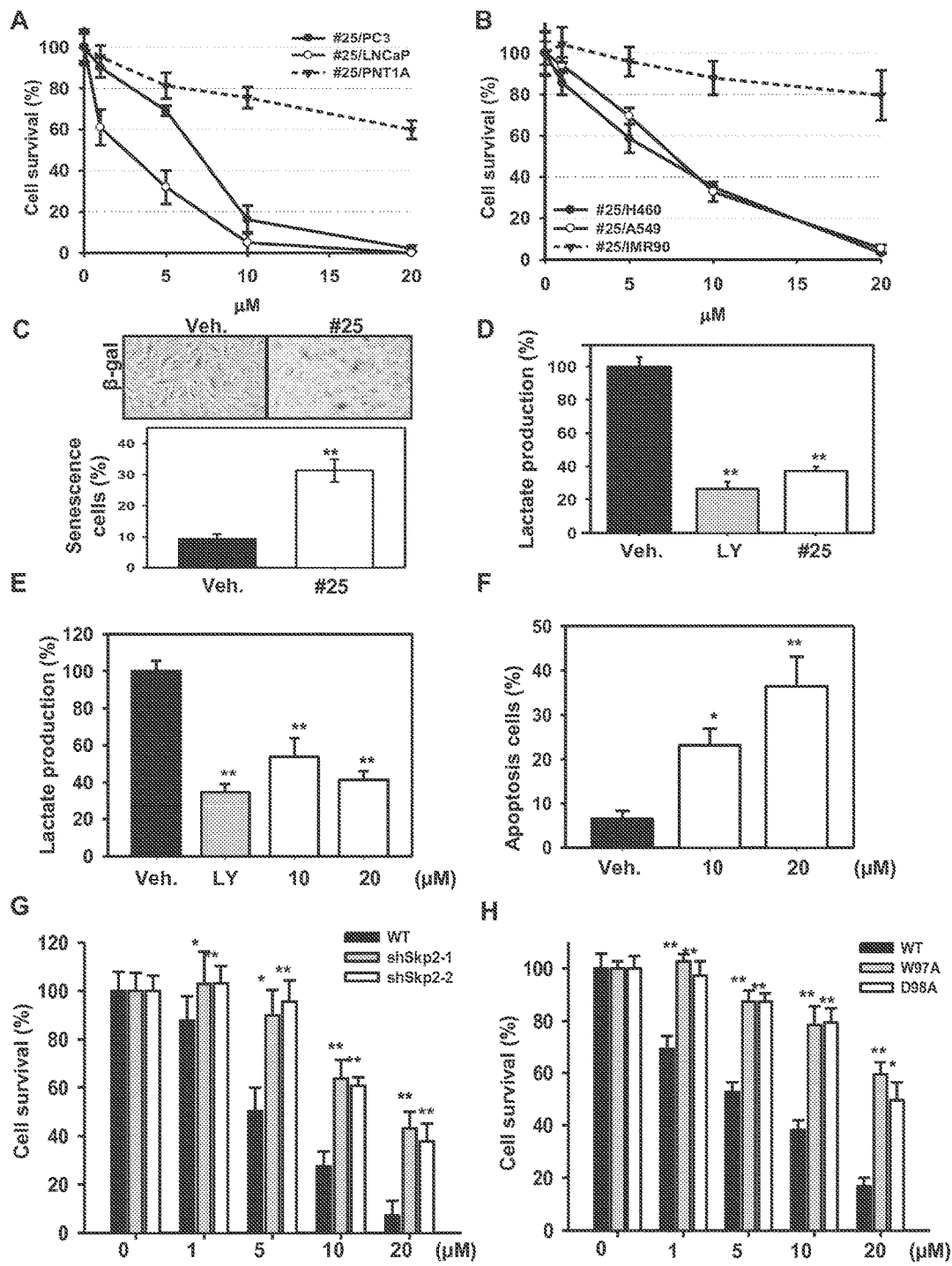
FIGS. 4A-H

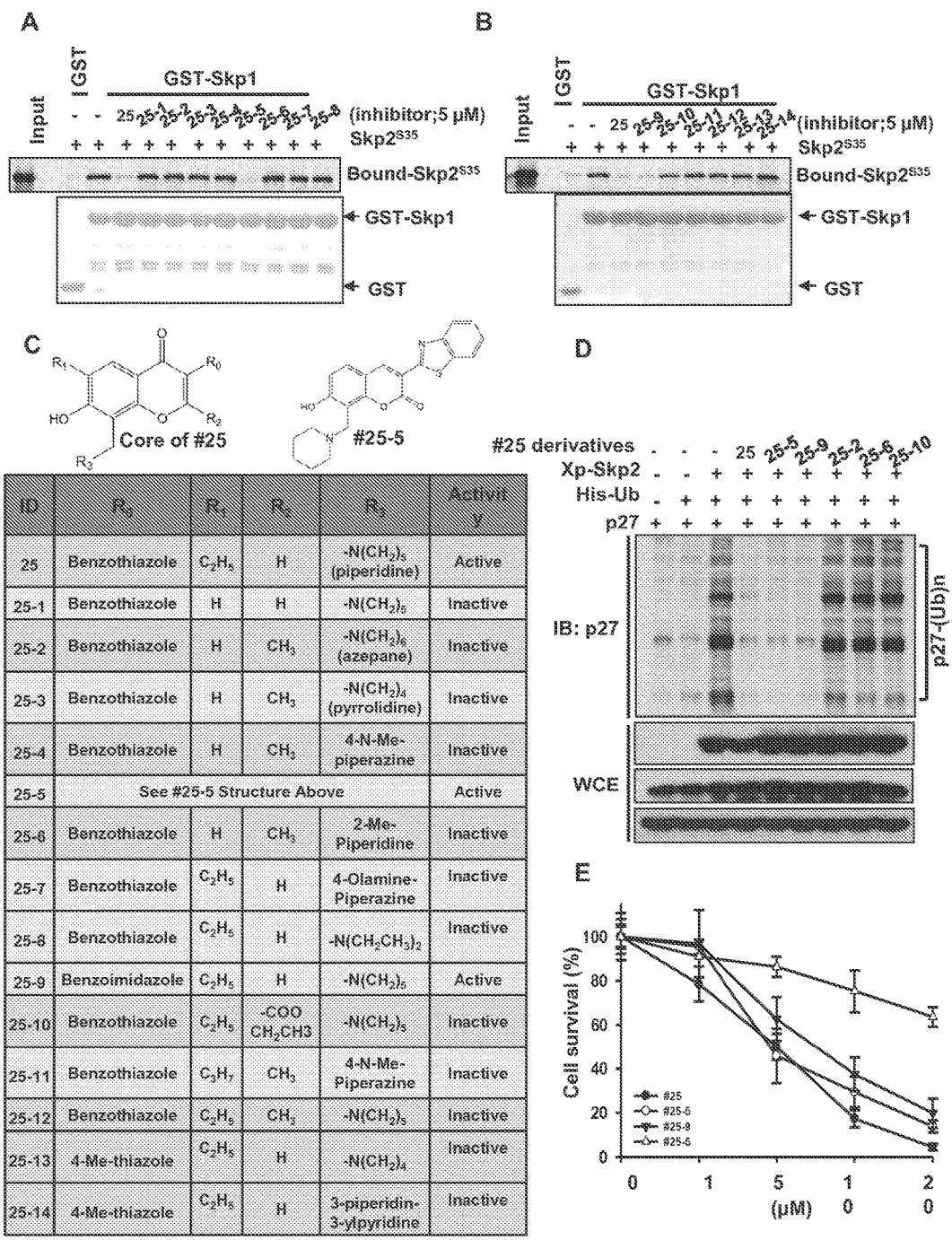
FIGS. 5A-E

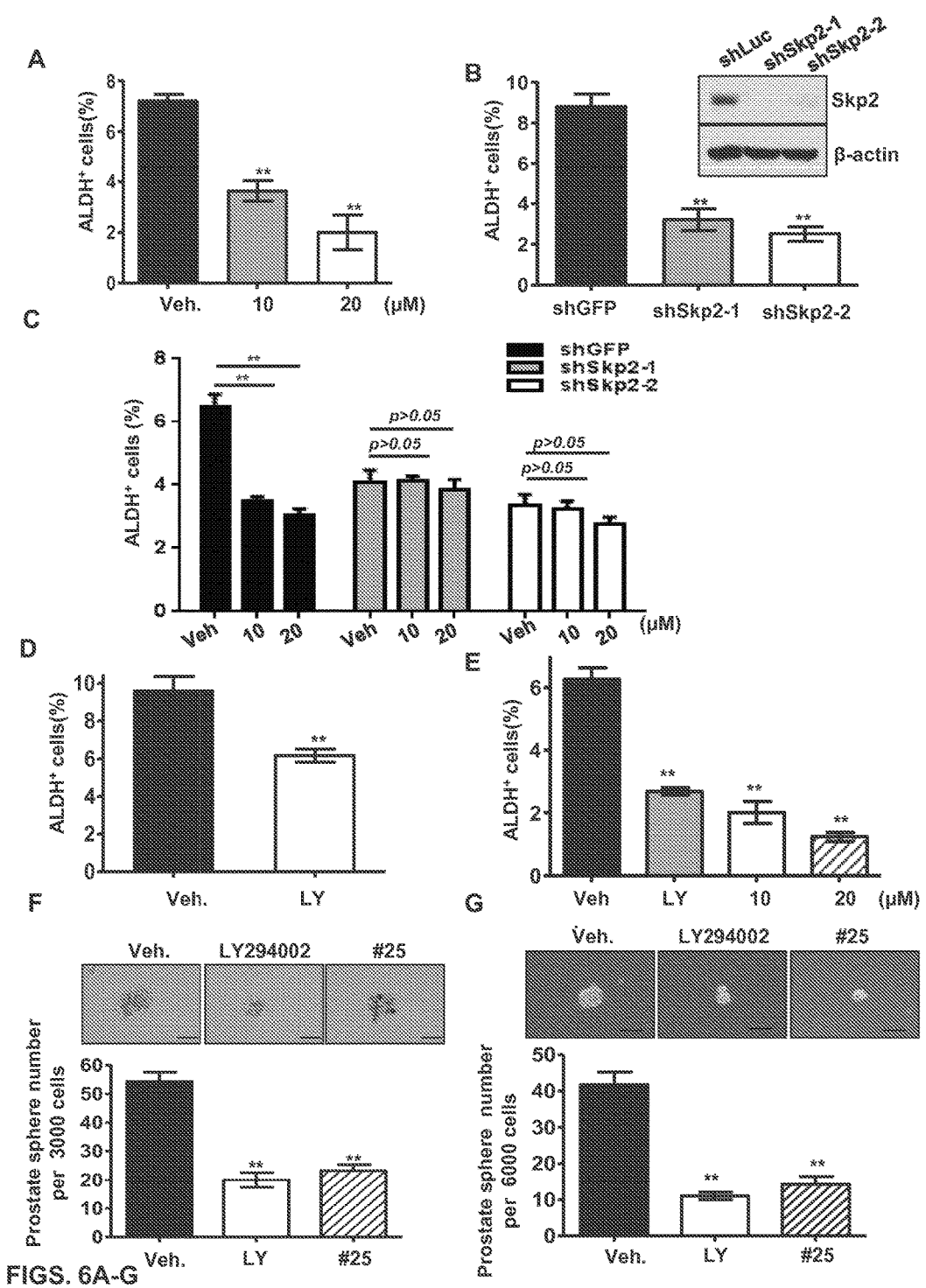
FIGS. 6A-G

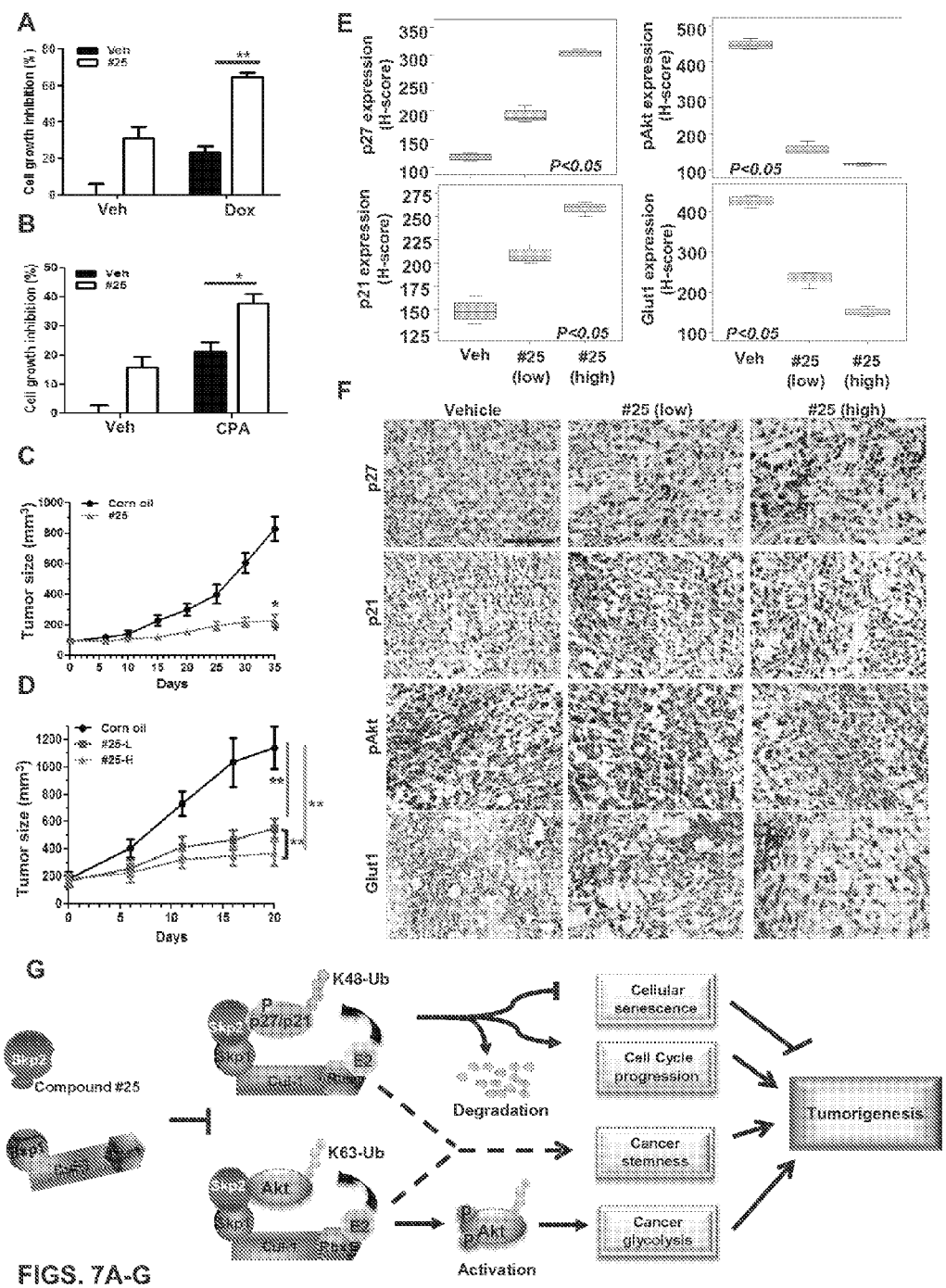
FIGS. 7A-G

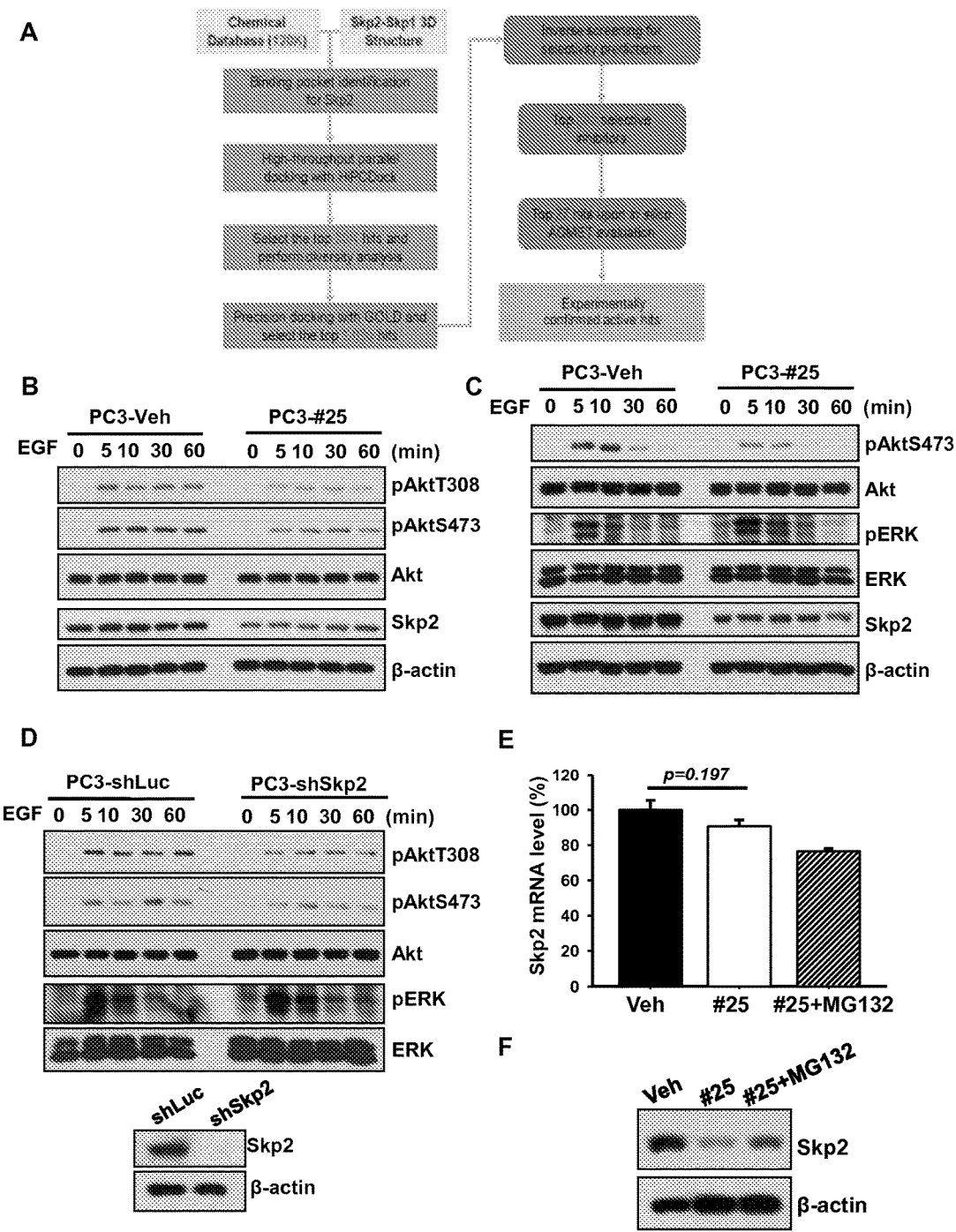
FIGS. 8A-F

A

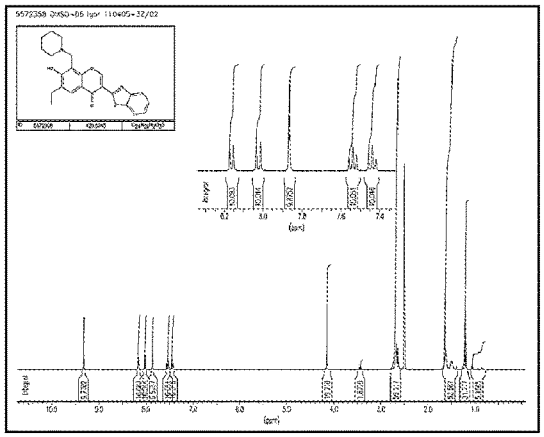

B

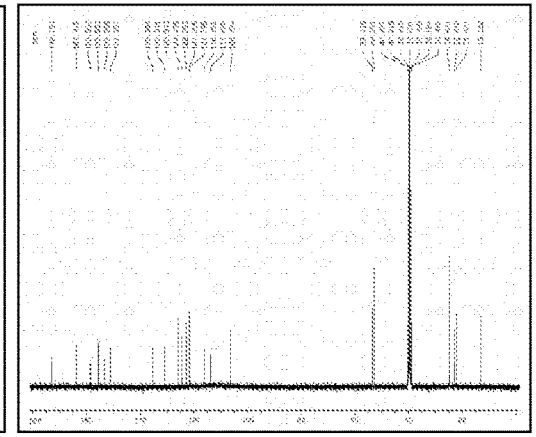

C

```
Column: Onyx C18 50x4.6mm | 3.75ml/min | Columns Reg Valve
Gradient: "A"->@2.2min->"B"(Hold 0.4min)->@0.2min->"A"->PostRun
PMP1, Solvent A         : 0.1%TFA in Acn/H2O (2.5:97.5)
PMP1, Solvent B         : 0.1% TFA in AcN
PMP1, Solvent C         : 0.1%FA in ACN/H2O (2.5:97.5)
PMP1, Solvent D         : 0.1%FA in ACN
Ionization mode         :   APCI Positive
Signal 1: ADC1 A, ELSD
Peak RetTime Type  Width     Area       Height      Area
  #   [min]       [min]    [mV*s]       [mV]         %
----|-------|----|-------|----------|----------|--------|
  1   1.456 BB   0.0504  3017.67554  967.60461  100.0000
Totals :                 3017.67554  967.60461
Signal 2: DAD1 A, Sig=300,200 Ref=off
Peak RetTime Type  Width     Area       Height      Area
  #   [min]       [min]    [mAU*s]      [mAU]        %
----|-------|----|-------|----------|----------|--------|
  1   1.247 BV   0.0235    30.81036   20.53621   0.3754
  2   1.312 VV   0.0234    40.63704   27.22821   0.4952
  3   1.400 VV   0.0562  7873.91309 2345.29272  95.9435
  4   1.520 VV   0.0304    63.08567   31.51116   0.7687
  5   1.580 VV   0.0269    28.00304   15.65306   0.3412
  6   1.624 VB   0.0428    66.53894   21.67898   0.8108
  7   1.833 BP   0.0271   103.83321   60.15947   1.2652
Totals :                 8206.82133 2522.05981
Signal 3: MSD1 TIC, MS File
Peak RetTime Type  Width     Area       Height      Area
  #   [min]       [min]                             %
----|-------|----|-------|----------|----------|--------|
  1   1.470 VV   0.0725  4.53833e8  8.37005e7  100.0000
Totals :                 4.53833e8  8.37005e7
```

FIGS. 9A-C

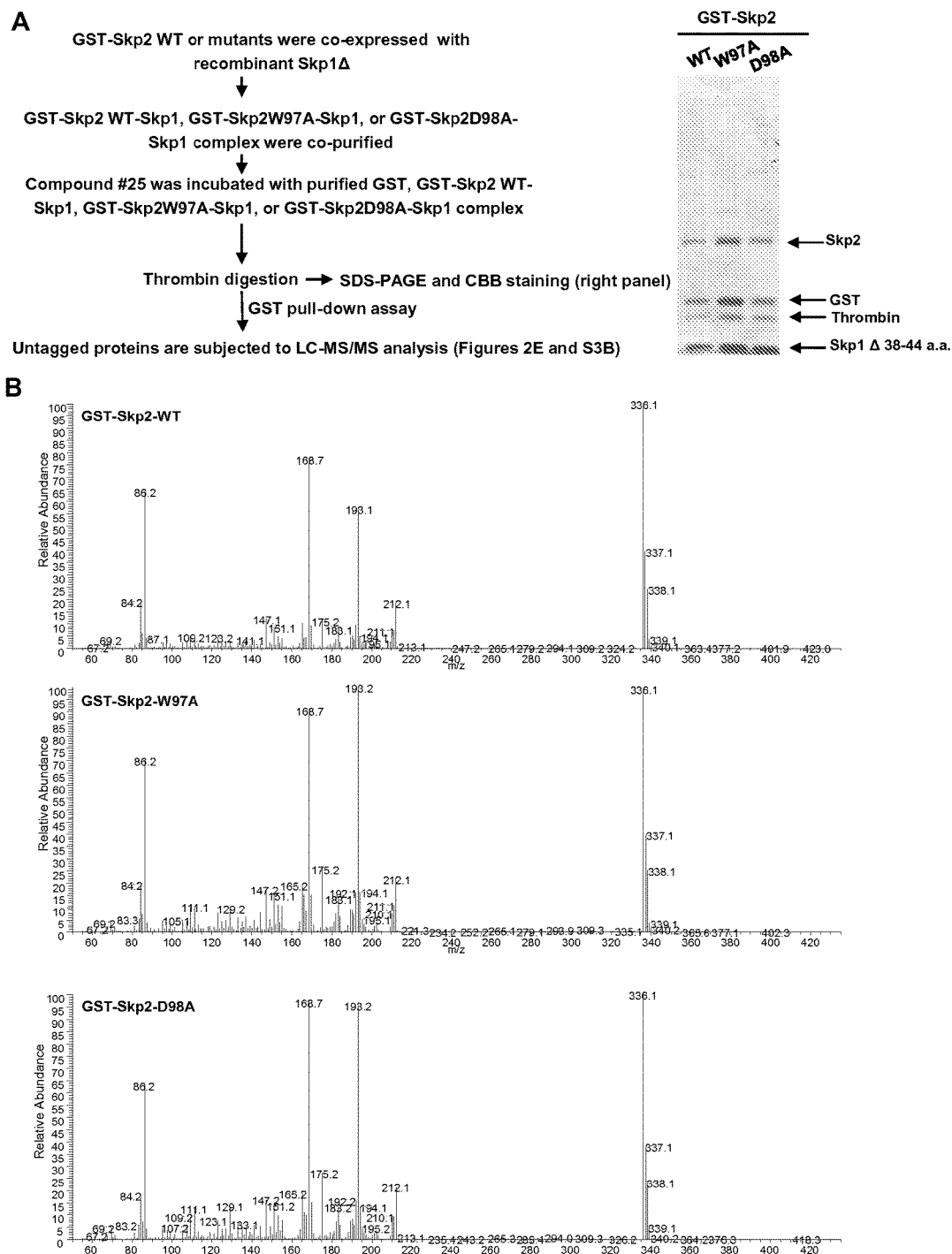
FIGS. 10A-B

A
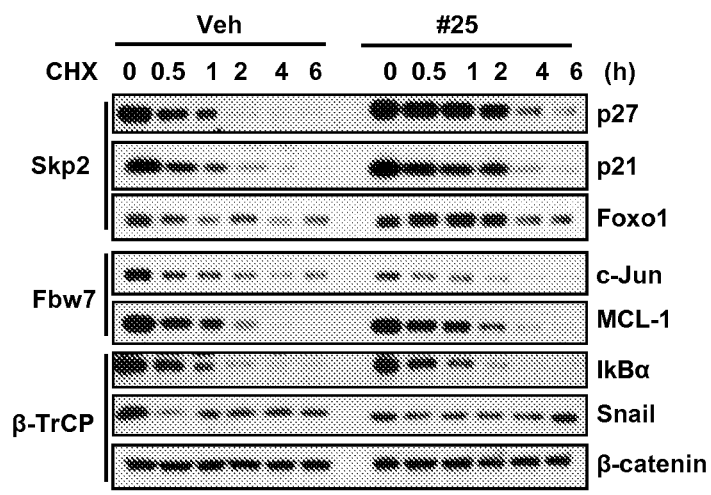
B
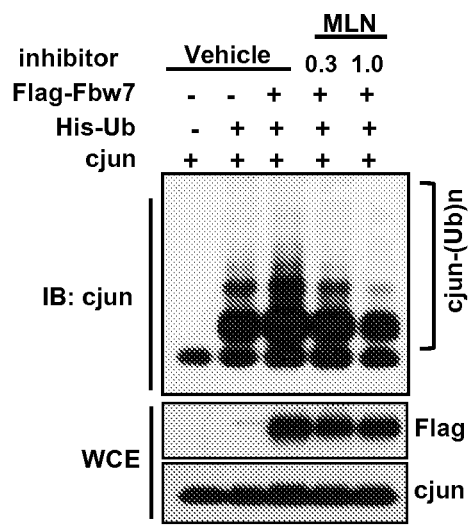
FIGS. 11A-B

A
| | Cancer type | IC$_{50}$ | p53 status |
|---|---|---|---|
| LNCaP | Prostate | 1.22 | WT |
| PC3 | Prostate | 5.61 | Null |
| A549 | Lung | 5.36 | WT |
| NCI-H460 | Lung | 5.15 | WT |
| NCI-H3255 | Lung | 5.38 | Mutant |
| NCI-H1299 | Lung | 10.50 | Deletion |
| Hep3B | Liver | 9.84 | Deletion |
| U2OS | Osteosarcoma | 5.41 | WT |
B 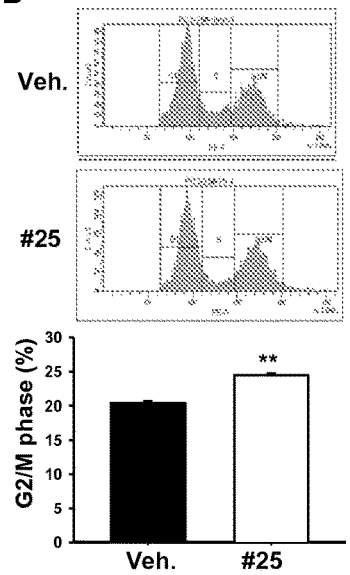
C 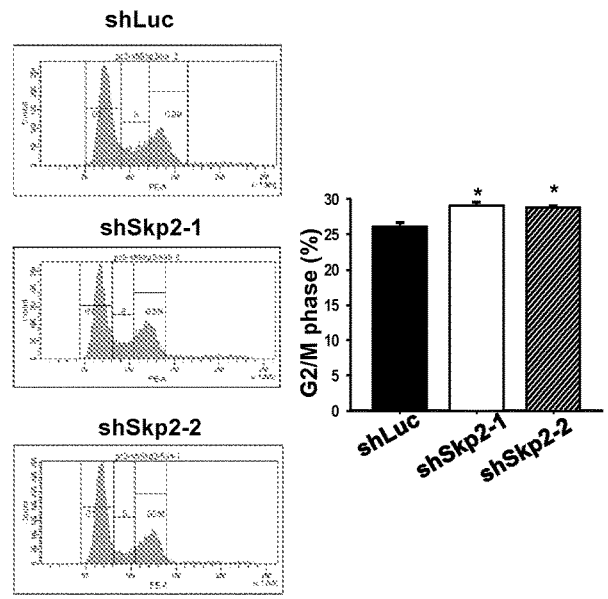
D 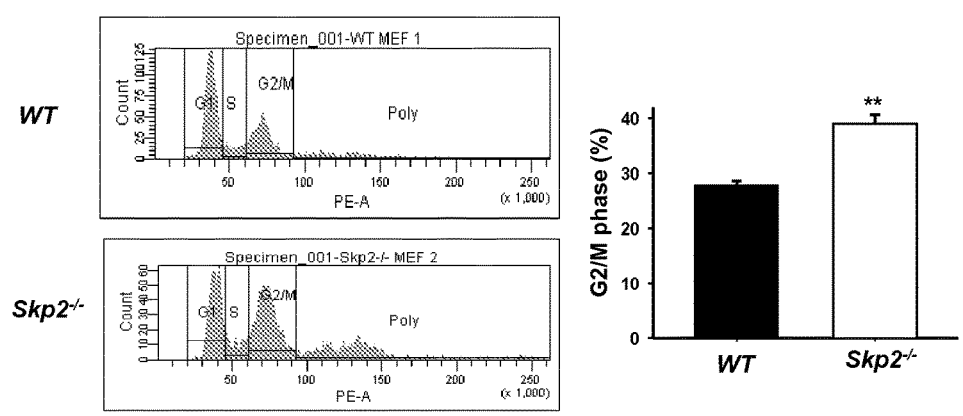
FIGS. 12A-D

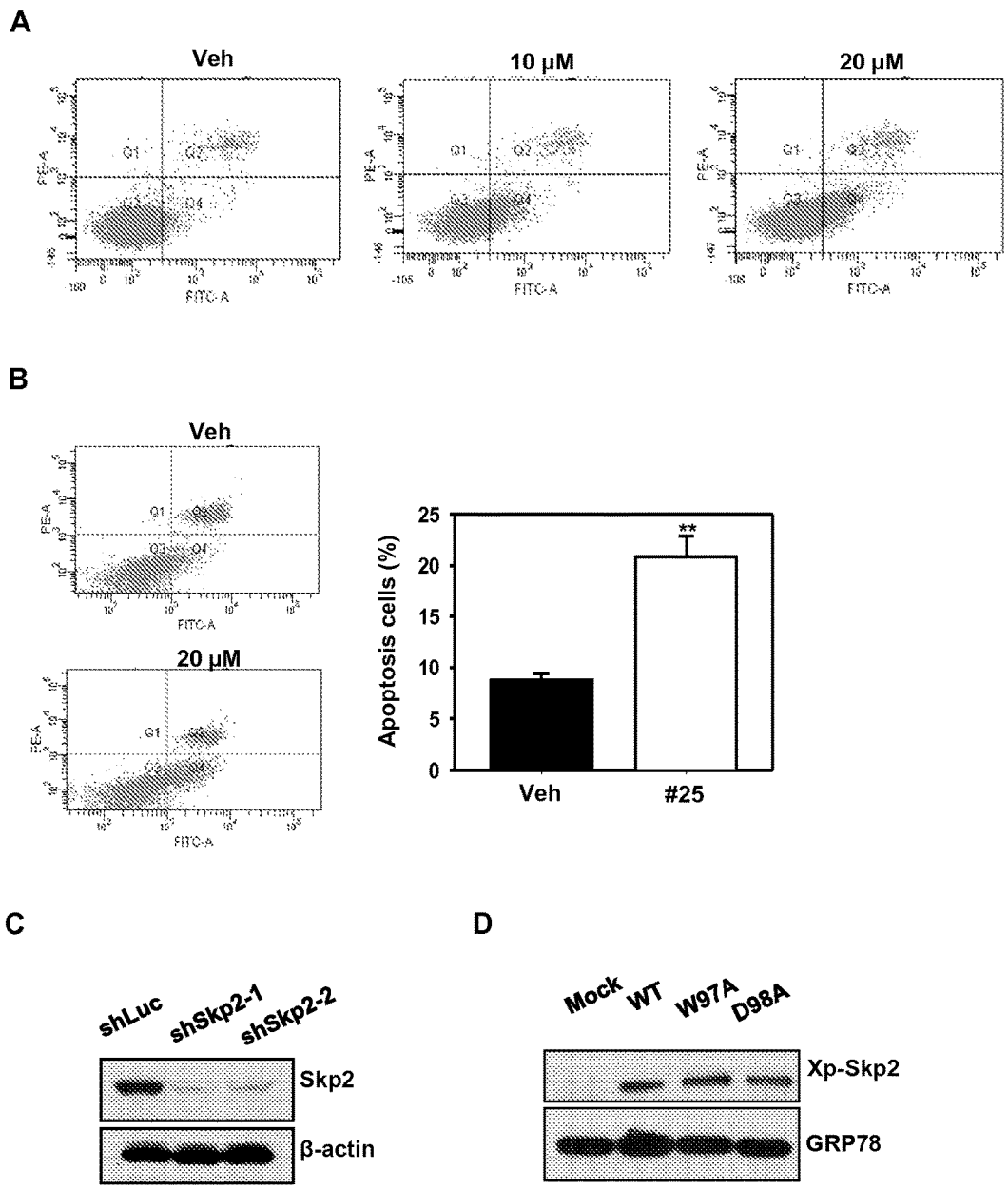
FIGS. 13A-D

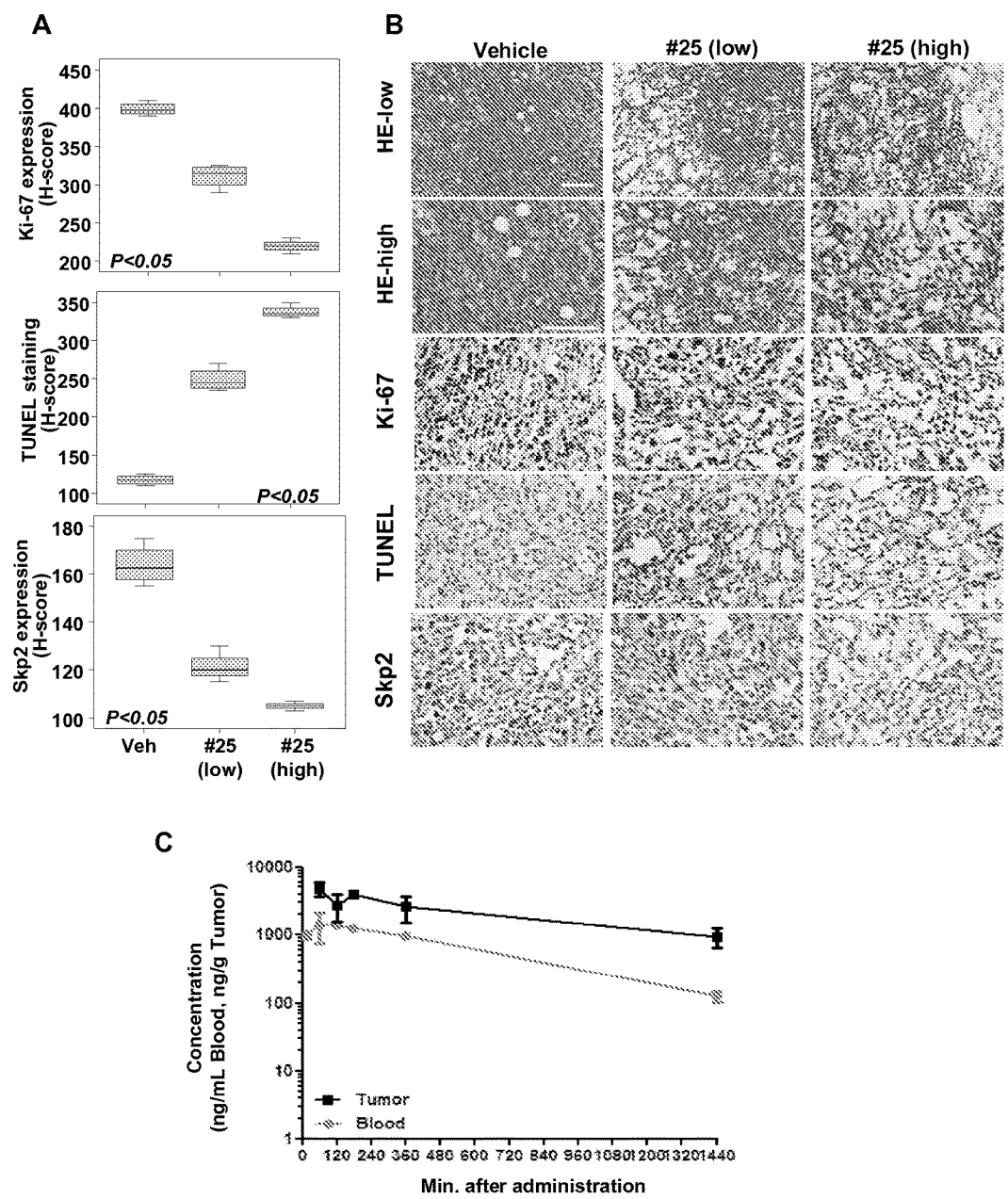
FIGS. 14A-C

ANTI-CANCER COMPOUNDS

This application is a national phase application under 35 U.S.C. 371 of International Application No. PCT/US2014/047216, filed Jul. 18, 2014, which claims the benefit of U.S. Provisional Patent Application No. 61/847,892, filed Jul. 18, 2013, the entirety of each of which is incorporated herein by reference.

The invention was made with government support under Grant Nos. 1RO1CA149321-01 and 1R01CA136787-01A2 awarded by the National Institutes of Health. The government has certain rights in the invention.

BACKGROUND OF THE INVENTION

1. Field of the Invention

The present invention relates generally to the fields of molecular biology, pharmaceuticals, and medicine. More particularly, it concerns Skp2 inhibitors.

2. Description of Related Art

Cancer is a complex disease characterized by multiple steps of genetic alterations occurring primarily through mutations of tumor suppressors and oncogenes. To date, chemotherapy and radiotherapy represent two major options for cancer treatment through inducing p53-dependent cellular senescence and apoptosis (Mandinova and Lee, 2011; Vazquez et al., 2008). However, advanced cancers often develop resistance to these treatments as they had often lost the p53 response due to frequent mutations on the p53 gene (accounting for ~50% in cancers). In this scenario, developing novel cancer treatment strategies via boosting p53-independent senescence and/or apoptosis responses is a key to the success of advanced cancer treatments.

In addition to activating senescence and apoptosis for cancer treatment, targeting aerobic glycolysis, a phenomenon called the Warburg effect (Vander Heiden et al., 2009; Warburg, 1956), has recently emerged as a promising strategy for cancer therapies. Cancer cells can display elevated glycolyis irrespectively of the presence or absence of oxygen, which warrants cancer cell proliferation and survival. Aerobic glycolysis is affected by oncogenic Akt kinase, a master kinase regulating many biological processes by phosphorylating its substrates (Buzzai et al., 2005; Elstrom et al., 2004; Robey and Hay, 2009). Activation of Akt is achieved by engaging growth factors to their cognate receptors. It has been recently discovered that Akt undergoes non-proteolytic K63-linked ubiquitination by TRAF6 E3 ligase upon IGF-1 treatment, which plays a critical role for Akt membrane recruitment, phosphorylation, and activation (Yang et al., 2009). Thus, K63-linked ubiquitination of Akt represents a posttranslational modification critical for Akt membrane recruitment and activation. Interestingly, Akt ubiquitination is also induced by activation of ErbB family receptors. Surprisingly, Skp2 SCF complex, but not TRAF6, is found to be critical for EGF-mediated Akt ubiquitination, phosphorylation, and activation (Chan et al., 2012). Thus, distinct E3 ligases are utilized to trigger Akt ubiquitination and activation by various growth factors.

Skp2 is an F-box protein, constituting one of the four subunits of the Skp1-Cullin-1 (Cul-1)-F-Box (SCF) ubiquitin E3 ligase complex. Earlier studies showed that Skp2 regulates apoptosis, cell cycle progression and proliferation by promoting ubiquitination and degradation of its substrates such as cell cycle inhibitor p27 (Nakayama et al., 2000; Nakayama et al., 2004). However, a new role of Skp2 SCF complex has been attributed in triggering non-proteolytic K63-linked ubiquitination (Chan et al., 2012). Overexpression of Skp2 is frequently observed in human cancer, and is inversely correlated with p27 levels, suggesting that Skp2 overexpression may have essential functions in human cancer development as a result of p27 downregulation (Hershko, 2008). In line with these observations, overexpression of Skp2 in prostate cancer cells significantly promotes tumorigenesis in a xenograft tumor model (Lin et al., 2009). Moreover, Skp2 overexpression has been found to promote cancer invasion and metastasis, whereas its deficiency inhibits these processes (Chan et al., 2010a). Using a Skp2-deficient mouse model, it has been shown that that Skp2 is required for cancer development in multiple tumor-promoting conditions, including PTEN, ARF, pRB inactivation as well as Her2/Neu overexpression. This may be achieved by triggering p53 independent, p27-dependent cellular senescence/apoptosis or inhibiting Akt-mediated glycolysis (Chan et al., 2012; Lin et al., 2010; Wang et al., 2010). Collectively, these studies suggest Skp2 targeting is a promising strategy for cancer treatment, thereby calling for an urgent need to develop specific Skp2 inhibitors.

SUMMARY OF THE INVENTION

The present invention overcomes limitations in the prior art by providing new treatments for cancer. In certain aspects, inhibitors of Skp2 are provided and may be used to treat a cancer.

An aspect of the present invention relates to a method of treating a hyperproliferative disease, comprising administering to a subject an effective amount of a compound having the structure:

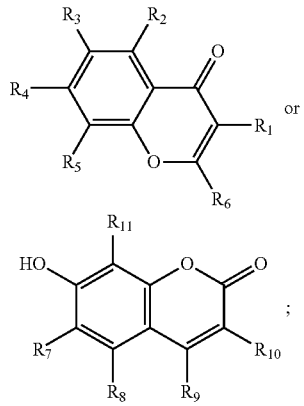

wherein $R_1$ is heteroaryl$_{(C \leq 18)}$ or substituted heteroaryl$_{(C \leq 18)}$; $R_2$, $R_3$, $R_4$, $R_5$, $R_7$, $R_8$, $R_9$, and $R_{10}$ are each independently selected from the group consisting of hydrogen, alkyl$_{(C \leq 18)}$, substituted alkyl$_{(C \leq 18)}$, heteroaryl$_{(C \leq 18)}$, substituted heteroaryl$_{(C \leq 18)}$, heterocycloalkyl$_{(C \leq 18)}$, substituted heterocycloalkyl$_{(C \leq 18)}$, acyl$_{(C \leq 18)}$, —C(O)O-alkyl$_{(C \leq 18)}$, -alkyl$_{(C \leq 12)}$-heterocycloalkyl$_{(C \leq 18)}$, aryl$_{(C \leq 18)}$, OH, SH, CF$_3$,

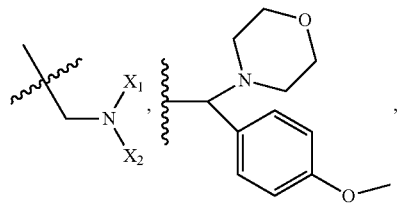

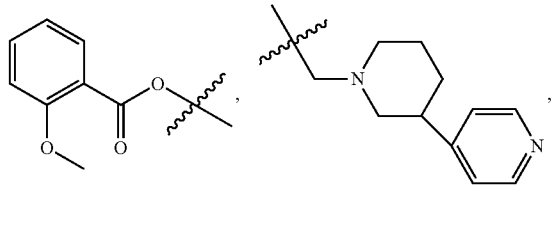

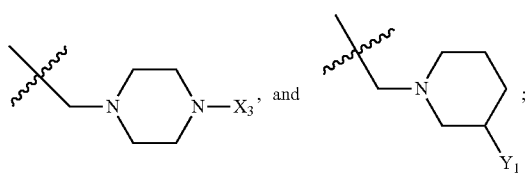

wherein $X_1$ and $X_2$ are each independently hydrogen, substituted alkyl$_{(C1-12)}$, or alkyl$_{(C1-12)}$; wherein $X_3$ is alkyl$_{(C\leq12)}$ or substituted alkyl$_{(C\leq12)}$; wherein $Y_1$ is —H, aryl$_{(C\leq18)}$, or heteroaryl$_{(C\leq18)}$; and wherein $R_6$ is selected from the group consisting of —H, alkyl$_{(C\leq18)}$, —NH$_2$, C(O)Oalkyl$_{(C\leq18)}$, and substituted alkyl$_{(C\leq18)}$; wherein $R_{11}$ is -alkyl$_{(C\leq6)}$-heterocycloalkyl$_{(C\leq18)}$ or -alkyl$_{(C\leq6)}$-substituted heterocycloalkyl$_{(C\leq18)}$; or a pharmaceutically acceptable salt or tautomer thereof. In some embodiments, the compound has the structure the compound has the structure

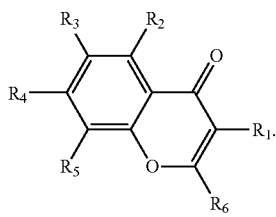

In some embodiments, $R_2$, $R_3$, $R_4$, and $R_5$ are each independently selected from the group consisting of —H, OH, alkyl$_{(C1-12)}$, substituted alkyl$_{(C1-12)}$, —CH$_2$-heterocycloalkyl$_{(C\leq12)}$, —C(O)O-alkyl$_{(C1-12)}$,

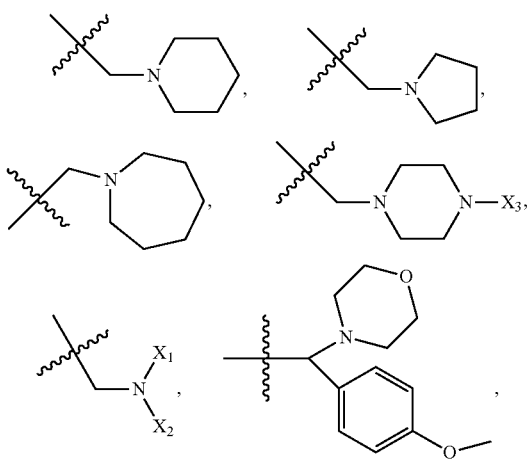

wherein $X_3$ is alkyl$_{(C1-6)}$ or substituted alkyl$_{(C1-6)}$. $R_1$ may be heteroaryl$_{(C\leq12)}$ or heteroaryl$_{(C\leq8)}$. In some embodiments, $R_1$ is selected from the group consisting of

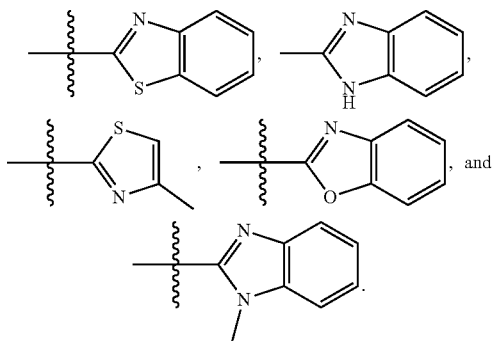

In some embodiments, $R_1$ is

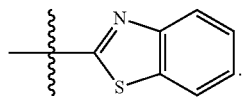

$R_2$ may be —H or —CH$_2$-heterocycloalkyl$_{(C\leq18)}$. $R_2$ may be —CH$_2$-heterocycloalkyl$_{(C\leq8)}$ In some embodiments, $R_2$ is —H. $R_3$ may be —H, —OH, alkyl$_{(C1-12)}$, or substituted alkyl$_{(C1-12)}$. $R_3$ may be —H or alkyl$_{(C1-C6)}$. In some embodiments, $R_3$ is —CH$_2$CH$_3$. $R_4$ may be —OH or —SH. In some preferred embodiments, $R_4$ is —OH. $R_5$ may be —H, -alkyl$_{(C1-6)}$-substituted heterocycloalkyl$_{(C\leq18)}$, heterocycloalkyl$_{(C\leq18)}$, alkyl$_{(C1-12)}$, or substituted alkyl$_{(C1-12)}$. $R_5$ may be a —CH$_2$-substituted heterocycloalkyl$_{(C\leq18)}$, more preferably a —CH$_2$-substituted heterocycloalkyl$_{(C\leq8)}$, more preferably a —CH$_2$-substituted heterocycloalkyl$_{(C\leq6)}$. In some embodiments, $R_5$ is —CH$_2$—Y$_2$; wherein $Y_2$ is selected from the group consisting of —N(CH$_3$)$_2$, N(CH$_2$CH$_2$OH)$_2$,

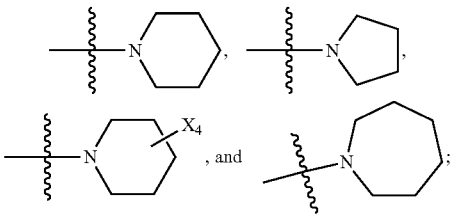

wherein $X_4$ is alkyl$_{(C1-12)}$. In some preferred embodiments, $Y_2$ is
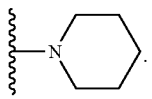
$R_6$ may be —H, CH$_3$, alkyl$_{(C1-12)}$, NH$_2$, or CF$_3$. In some embodiments, $R_6$ is —H.
In some embodiments, the compound is selected from the group consisting of
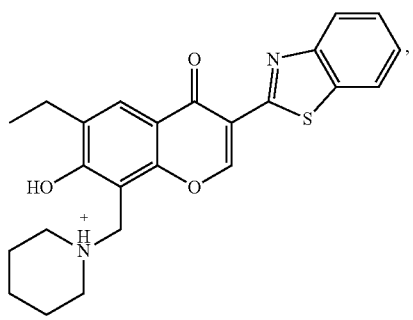
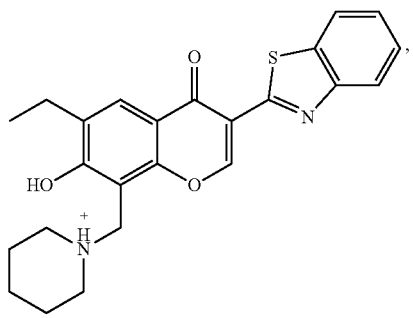
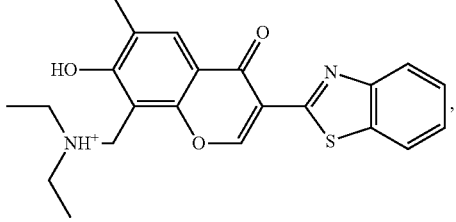
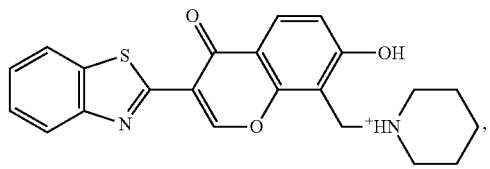
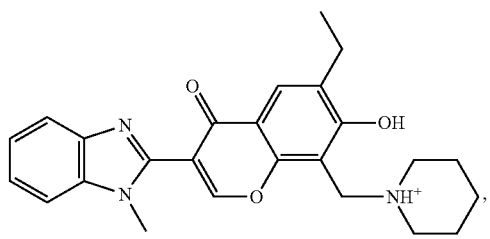
-continued
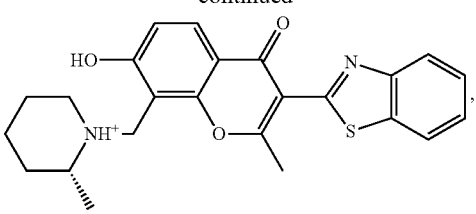
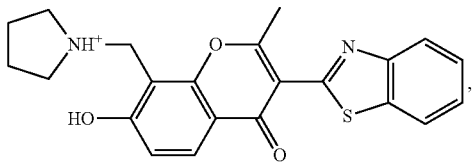
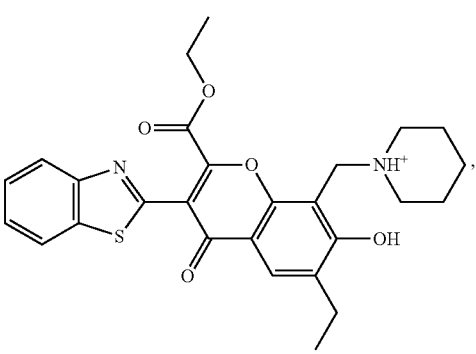
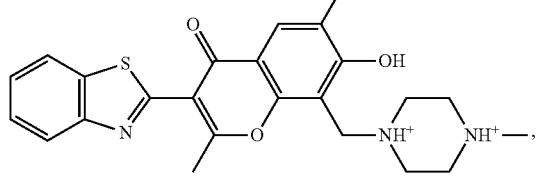
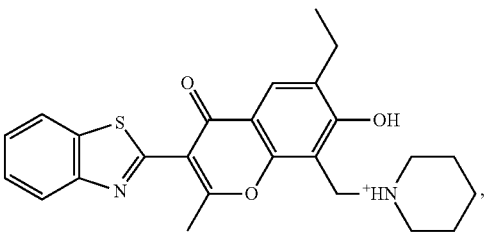
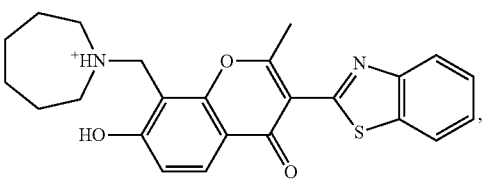
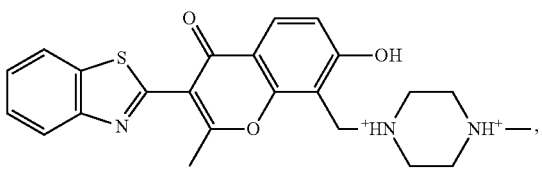

-continued
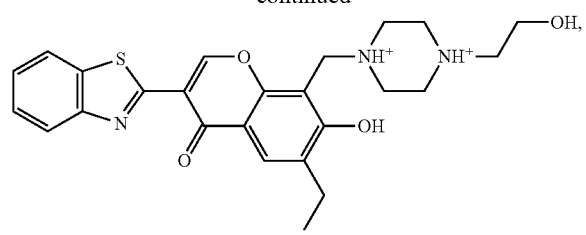
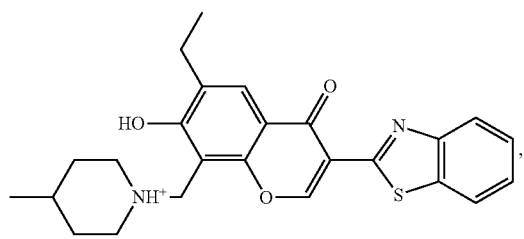
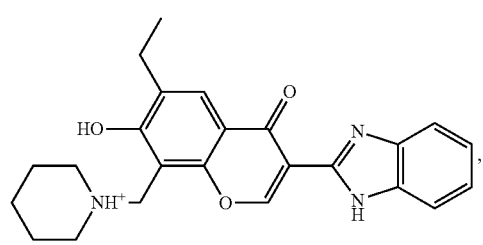
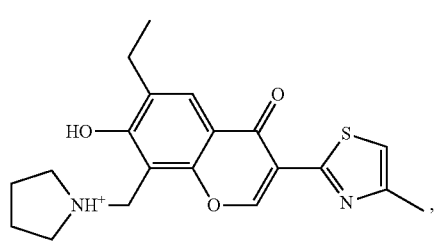
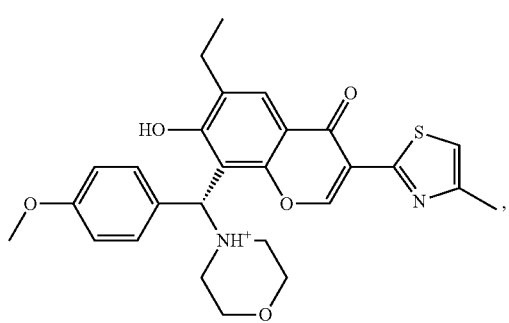
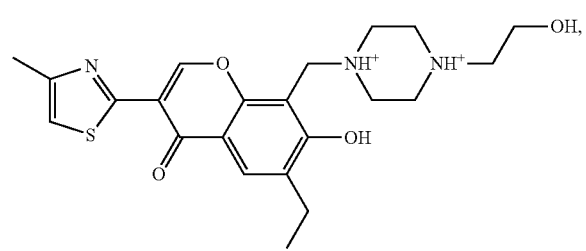
-continued
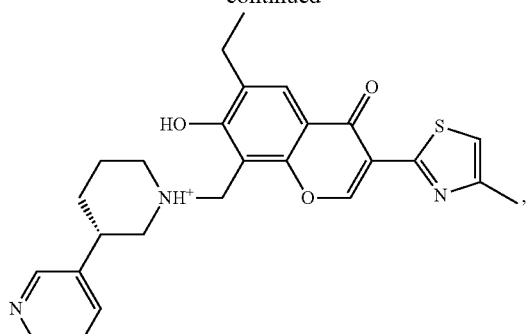
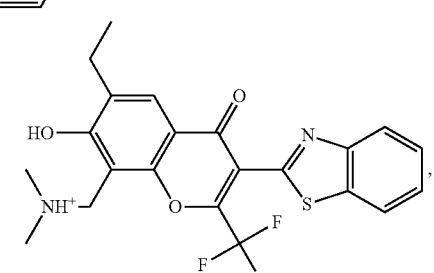
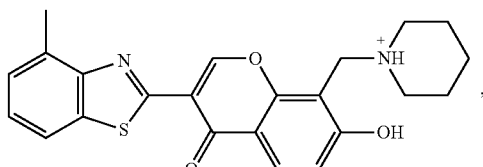
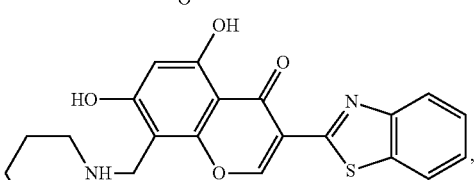
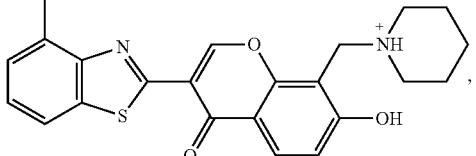
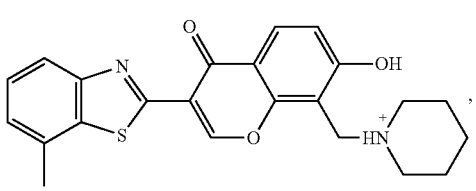
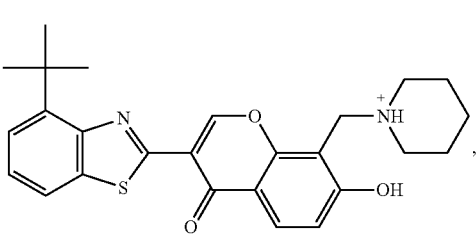

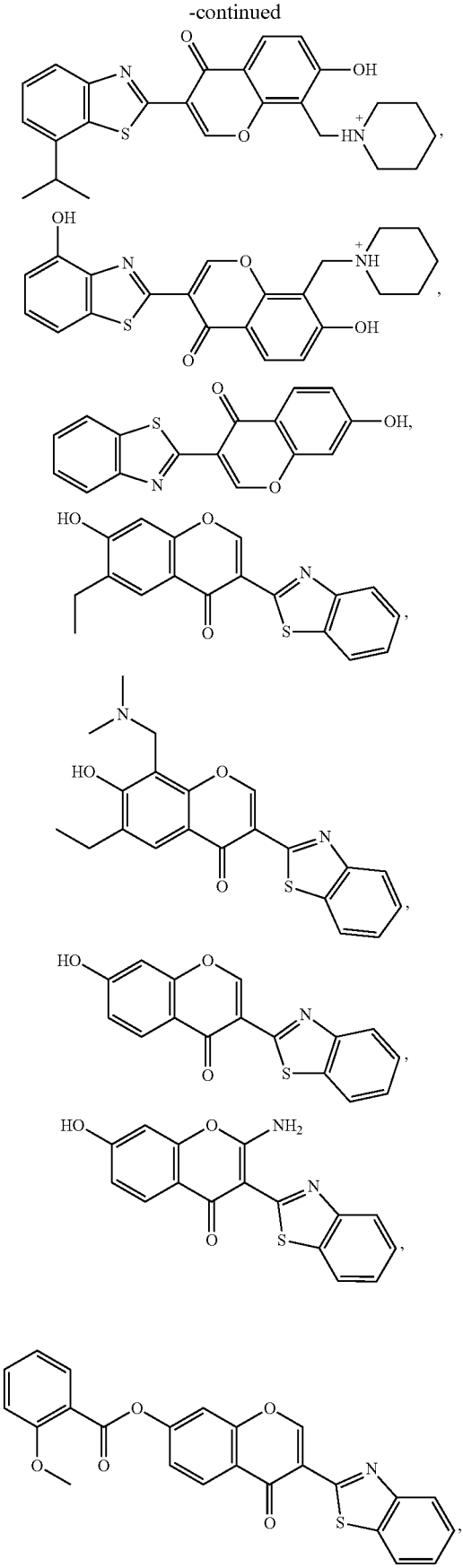
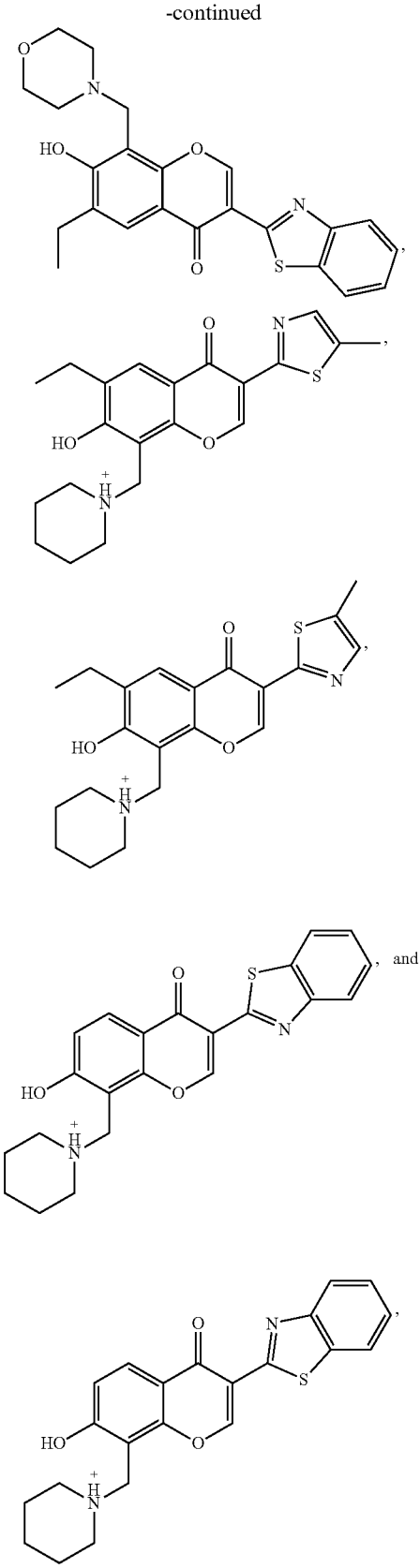
or a pharmaceutically acceptable salt thereof. In some embodiments, the compound has the structure:

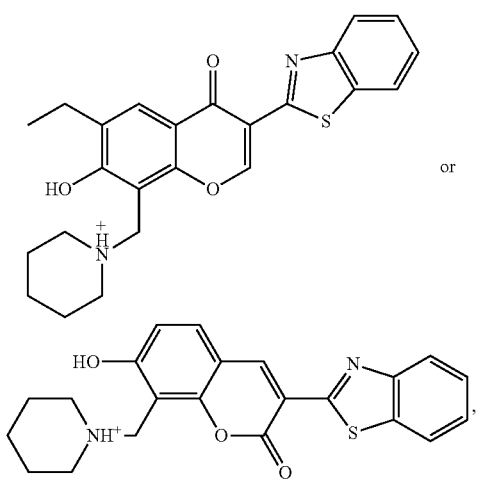

or a pharmaceutically acceptable salt thereof.

In some embodiments, the compound has the structure:

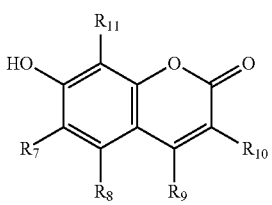

or a pharmaceutically acceptable salt or tautomer thereof. In some embodiments, $R_{10}$ is

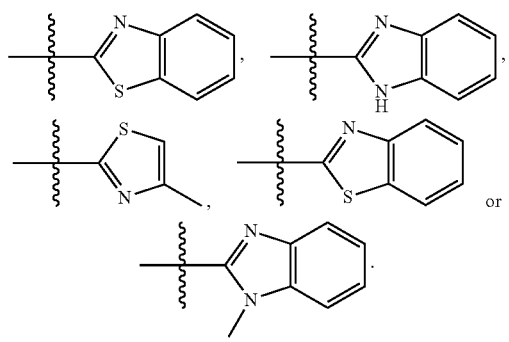

In some embodiments, $R_{10}$ is

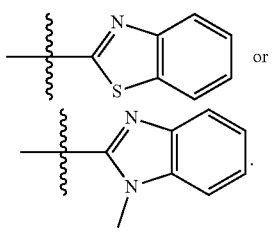

$R_{11}$ may be -alkyl$_{(C1-6)}$-substituted heterocycloalkyl$_{(C\leq 18)}$, heterocycloalkyl$_{(C\leq 18)}$, alkyl$_{(C1-12)}$, or substituted alkyl$_{(C1-12)}$. In some embodiments, $R_{11}$ is —CH$_2$-substituted heterocycloalkyl$_{(C\leq 18)}$. $R_{11}$ may be —CH$_2$-substituted heterocycloalkyl$_{(C\leq 8)}$. $R_{11}$ may be —CH$_2$-substituted heterocycloalkyl$_{(C\leq 6)}$. In some embodiments, $R_{11}$ is —CH$_2$—Y$_2$; wherein Y$_2$ is selected from the group consisting of —N(CH$_3$)$_2$, N(CH$_2$CH$_2$OH)$_2$,

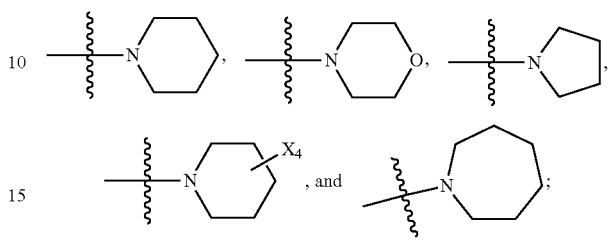

wherein $X_4$ is alkyl$_{(C1-12)}$. $R_7$ may be H. $R_8$ may be H. $R_9$ may be H. In some embodiments, $R_7$, $R_8$, and $R_9$ are H. In some embodiments, the compound has the structure

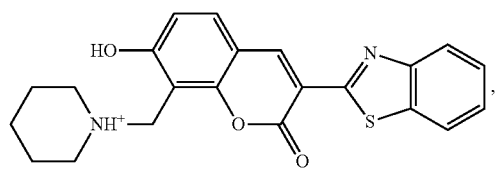

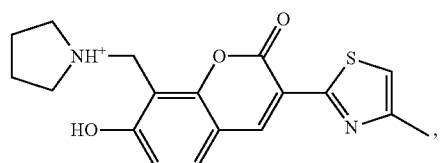

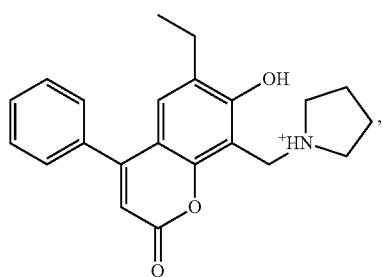

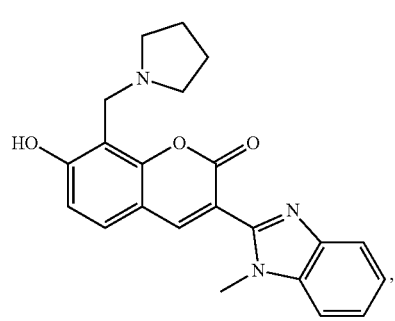

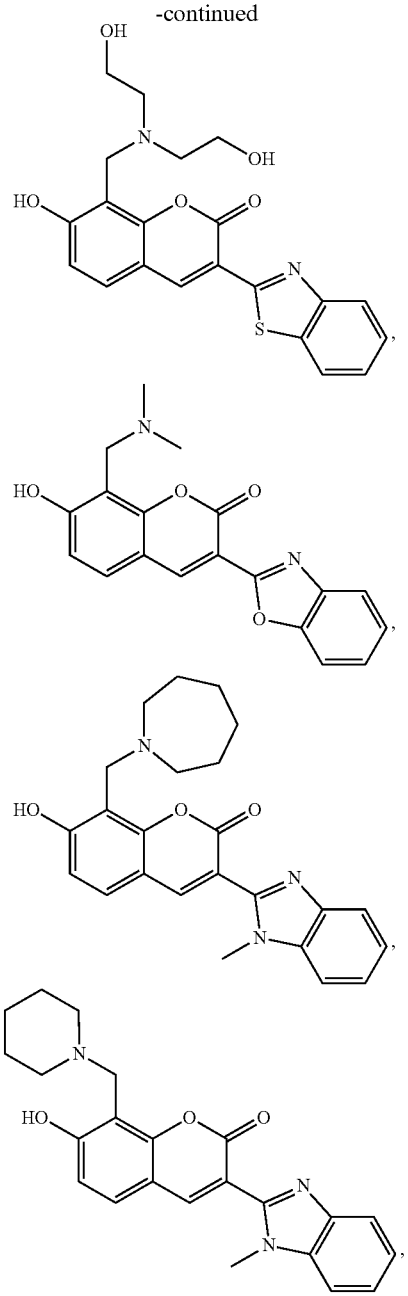

or a pharmaceutically acceptable salt thereof.

The subject may be a mammal such as, e.g., a human. The disease may be a cancer. The cancer may be a breast cancer, lung cancer, prostate cancer, ovarian cancer, brain cancer, liver cancer, cervical cancer, pancreatic cancer, colon cancer, colorectal cancer, renal cancer, skin cancer, head and neck cancer, bone cancer, esophageal cancer, bladder cancer, uterine cancer, lymphatic cancer, stomach cancer, pancreatic cancer, testicular cancer, lymphoma, or leukemia. In some embodiments, the cancer is a lymphoma, breast cancer, prostate cancer, liver cancer, or osteosarcoma. In some embodiments, the method further comprises administering an additional anticancer therapy to the subject. The additional anticancer therapy may comprise a chemotherapeutic agent, radiation therapy, surgical therapy, immunotherapy, gene therapy, or a combination thereof. In some embodiments, the additional anticancer therapy comprises a chemotherapeutic agent. The chemotherapeutic agent may be doxorubicin, cyclophosphamide, docetaxel, paclitaxel, chlorambucil, gencitabine, 6-thioguanine, mercaptupurine, methotrexate, cisplatin, oxaliplatin, carboplatin, vinbastine, etoposide, vincristine, daunomycin, capecitabine, procarbazine, mechlorethamine, cyclophosphamide, camptothecin, bleomycin, busulfan, dactinomycin, tamoxifen, raloxifene, or 5-fluorouracil. In some embodiments, the composition is administered to the patient intravenously, intraperitoneally, intratracheally, intratumorally, intramuscularly, endoscopically, intralesionally, percutaneously, subcutaneously, regionally, or by direct injection or perfusion.

Another aspect of the present invention relates to a method of culturing a cell, comprising contacting a plurality of cells in vitro with an amount of a compound of the present invention effective to reduce differentiation, maintain an amount of dedifferentiation, or maintain a substantially dedifferentiated state in the cells; wherein the cells are pluripotent, multipotent, or totipotent.

Yet another aspect of the present invention relates to a pharmaceutical composition comprising a compound and a pharmaceutically acceptable carrier or excipient wherein the compound is of the formula:

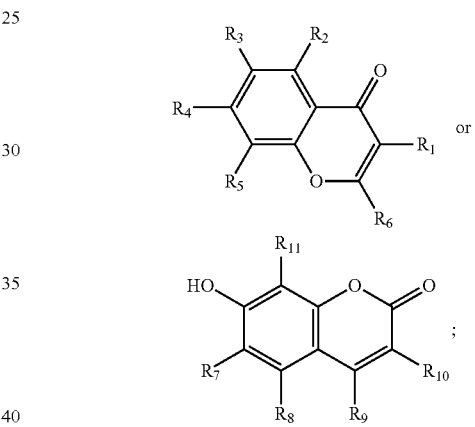

wherein: $R_1$ is heteroaryl$_{(C\leq18)}$ or substituted heteroaryl$_{(C\leq18)}$; $R_2$, $R_3$, $R_4$, $R_5$, $R_7$, $R_8$, $R_9$, and $R_{10}$ are each independently selected from the group consisting of hydrogen, alkyl$_{(C\leq18)}$, substituted alkyl$_{(C\leq18)}$, heteroaryl$_{(C\leq18)}$, substituted heteroaryl$_{(C\leq18)}$, heterocycloalkyl$_{(C\leq18)}$, substituted heterocycloalkyl$_{(C\leq18)}$, acyl$_{(C\leq18)}$, —C(O)O-alkyl$_{(C\leq18)}$, -alkyl$_{(C\leq12)}$-heterocycloalkyl$_{(C\leq18)}$, aryl$_{(C\leq18)}$, OH, SH, CF$_3$,

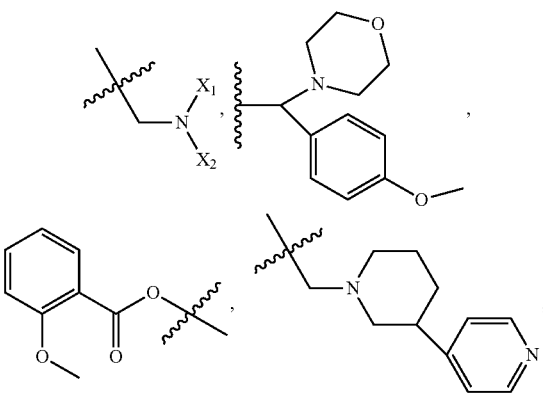

-continued

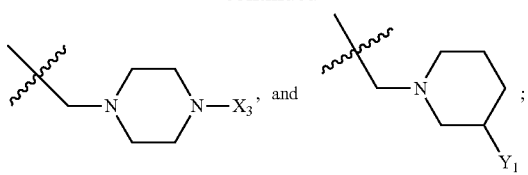

$X_1$ and $X_2$ are each independently hydrogen, substituted alkyl$_{(C1-12)}$, or alkyl$_{(C1-12)}$; $X_3$ is alkyl$_{(C\leq12)}$ or substituted alkyl$_{(C\leq12)}$; $Y_1$ is —H, aryl$_{(C\leq18)}$, or heteroaryl$_{(C\leq18)}$; and $R_6$ is selected from the group consisting of —H, alkyl$_{(C\leq18)}$, —NH$_2$, C(O)O alkyl$_{(C\leq18)}$, and substituted alkyl$_{(C\leq18)}$; $R_{11}$ is -alkyl$_{(C\leq6)}$-heterocycloalkyl$_{(C\leq18)}$ or -alkyl$_{(C\leq6)}$-substituted heterocycloalkyl$_{(C\leq18)}$; or a pharmaceutically acceptable salt or tautomer thereof. In some embodiments, the compound has the structure

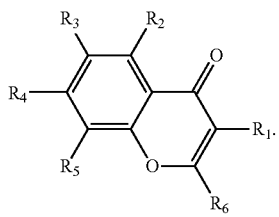

In some embodiments, $R_2$, $R_3$, $R_4$, and $R_5$ are each independently selected from the group consisting of —H, OH, alkyl$_{(C1-12)}$, substituted alkyl$_{(C1-12)}$, —CH$_2$-heterocycloalkyl$_{(C\leq12)}$, —C(O)O-alkyl$_{(C1-12)}$,

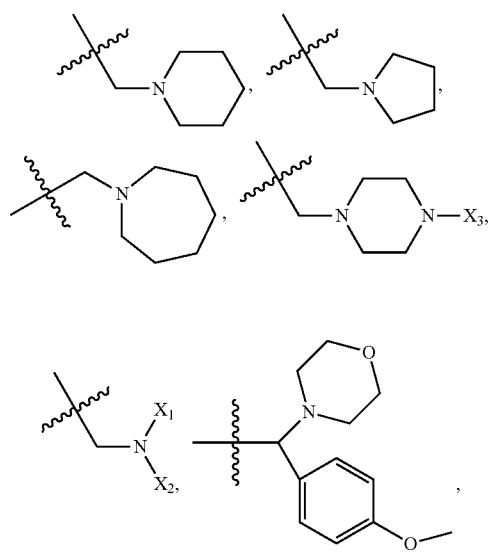

-continued

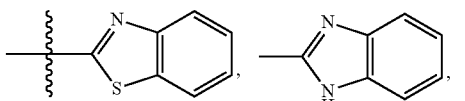

wherein $X_3$ is alkyl$_{(C1-6)}$ or substituted alkyl$_{(C1-6)}$. In some embodiments, $R_1$ is heteroaryl$_{(C\leq12)}$. In some embodiments, $R_1$ is heteroaryl$_{(C\leq8)}$. In a preferred embodiments, $R_1$ is selected from the group consisting of

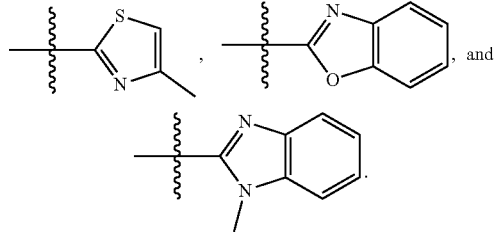

In some embodiments, $R_1$ is

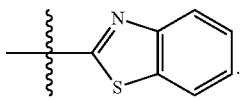 [SMILES: *c1nc2ccccc2s1]

$R_2$ may be —H or —CH$_2$-heterocycloalkyl$_{(C\leq18)}$. In some embodiments, $R_2$ is —CH$_2$-heterocycloalkyl$_{(C\leq8)}$ In other embodiments, $R_2$ is —H. $R_3$ may be —H, —OH, alkyl$_{(C1-12)}$, or substituted alkyl$_{(C1-12)}$. In some embodiments, $R_3$ is —H or alkyl$_{(C1-C6)}$. In a preferred embodiment, $R_3$ is —CH$_2$CH$_3$. $R_4$ may be —OH or —SH. In some embodiments, $R_4$ is —OH. In some embodiments, $R_5$ is —H, -alkyl$_{(C1-6)}$-substituted heterocycloalkyl$_{(C\leq18)}$, heterocycloalkyl$_{(C\leq18)}$, alkyl$_{(C1-12)}$, or substituted alkyl$_{(C1-12)}$. In some embodiments, $R_5$ is —CH$_2$-substituted heterocycloalkyl$_{(C\leq18)}$. In some embodiments, $R_5$ is —CH$_2$-substituted heterocycloalkyl$_{(C\leq8)}$. In some embodiments, $R_5$ is —CH$_2$-substituted heterocycloalkyl$_{(C\leq6)}$. In some embodiments, $R_5$ is —CH$_2$—$Y_2$; wherein $Y_2$ is selected from the group consisting of —N(CH$_3$)$_2$, N(CH$_2$CH$_2$OH)$_2$,

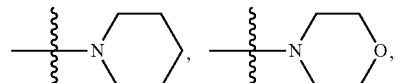

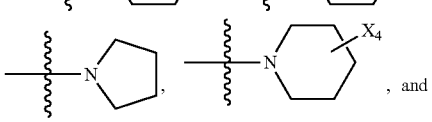

-continued
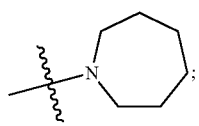
wherein $X_4$ is alkyl$_{(C1-12)}$. In some embodiments, $Y_2$ is
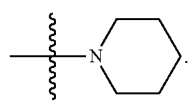 [SMILES: *N1CCCCC1]
$R_6$ may be —H, —CH$_3$, alkyl$_{(C1-12)}$, NH$_2$, or CF$_3$. In some embodiments, $R_6$ is —H.
In some embodiments, the compound is selected from the group consisting of
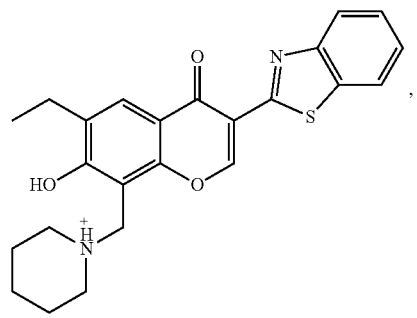
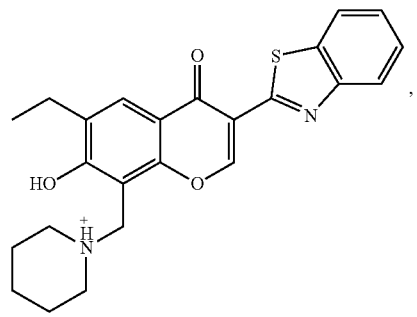
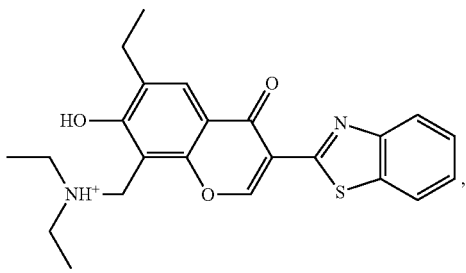
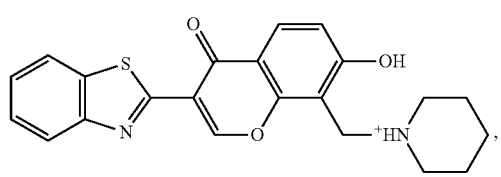
-continued
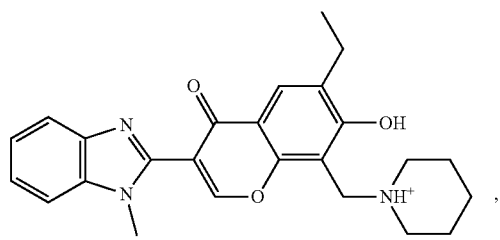
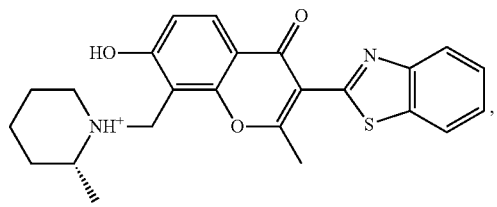
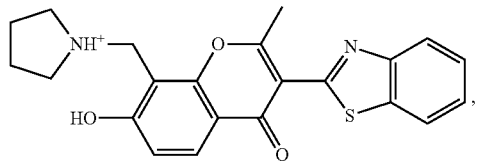
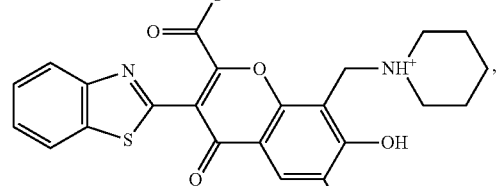
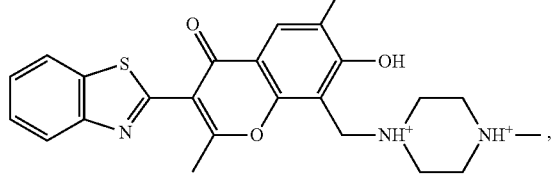
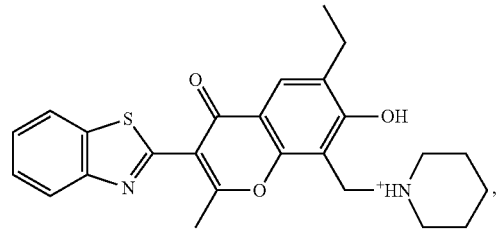
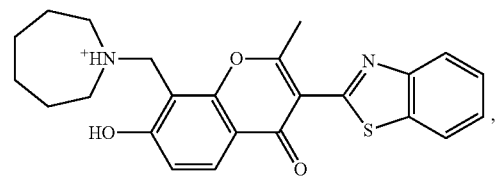

19
-continued
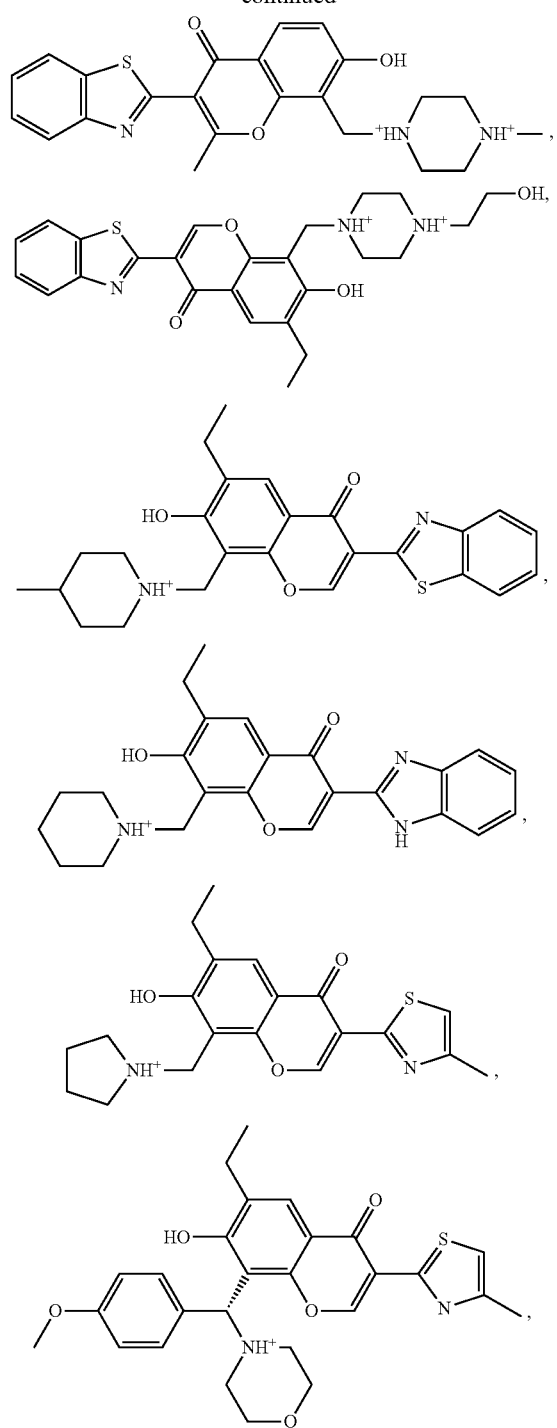
20
-continued
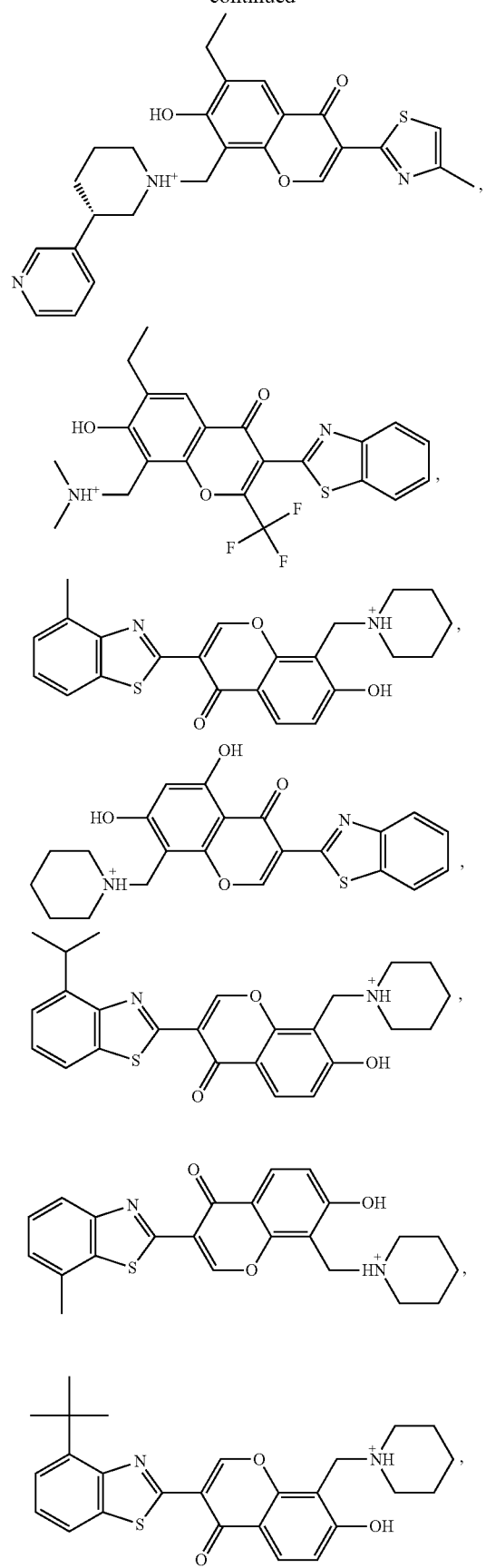

-continued
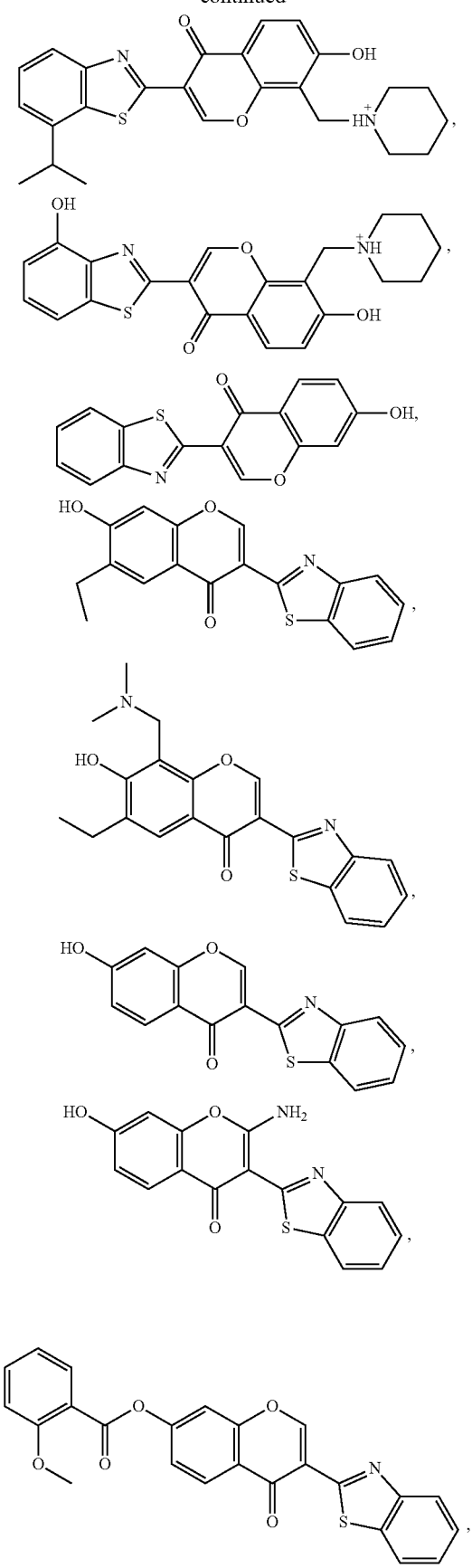
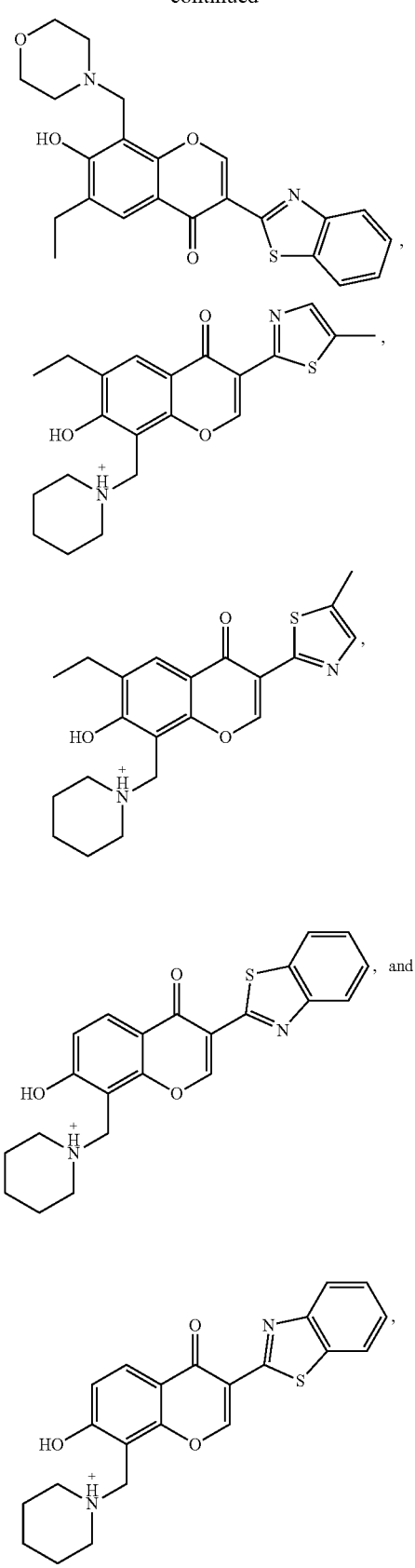
or a pharmaceutically acceptable salt thereof.

In other embodiments, the compound has the structure:

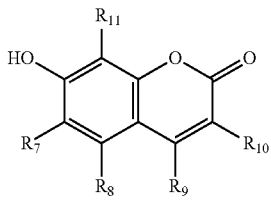

or a pharmaceutically acceptable salt or tautomer thereof. $R_{10}$ may be

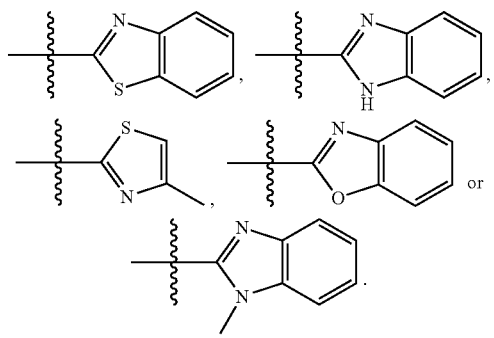

In some embodiments, $R_{10}$ is

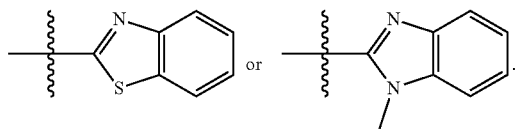 [SMILES: *c1nc2ccccc2s1 ; *c1nc2ccccc2n1C]

In some embodiments, $R_{11}$ is -alkyl$_{(C1-6)}$-substituted heterocycloalkyl$_{(C\leq18)}$, heterocycloalkyl$_{(C\leq18)}$, alkyl$_{(C1-12)}$, or substituted alkyl$_{(C1-12)}$. In some embodiments, $R_{11}$ is —CH$_2$-substituted heterocycloalkyl$_{(C\leq18)}$. In some embodiments, $R_{11}$ is —CH$_2$-substituted heterocycloalkyl$_{(C\leq8)}$. In some embodiments, $R_{11}$ is —CH$_2$-substituted heterocycloalkyl$_{(C\leq6)}$. In some embodiments, $R_{11}$ is —CH$_2$—Y$_2$; wherein Y$_2$ is selected from the group consisting of —N(CH$_3$)$_2$, N(CH$_2$CH$_2$—OH)$_2$,

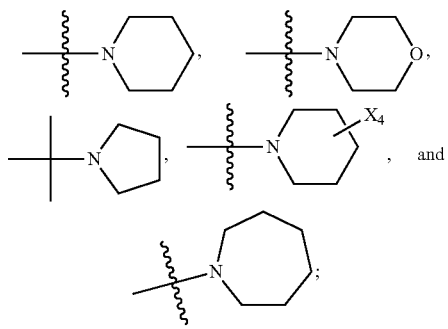

wherein $X_4$ is alkyl$_{(C1-12)}$. In some embodiments, $R_7$ is H. In some embodiments, $R_8$ is H. In some embodiments, $R_9$ is H. In some embodiments, $R_7$, $R_8$, and $R_9$ are H. In some embodiments, the compound has the structure

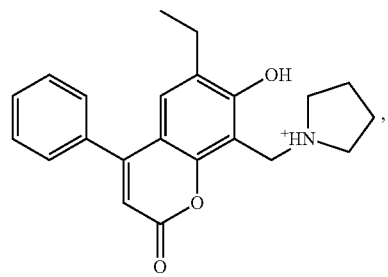

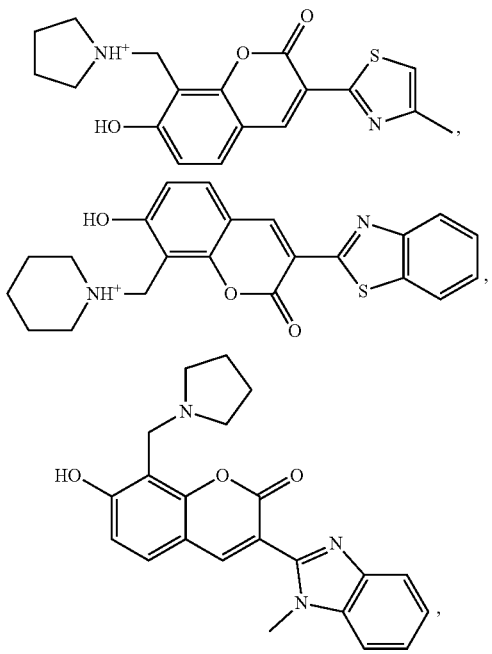

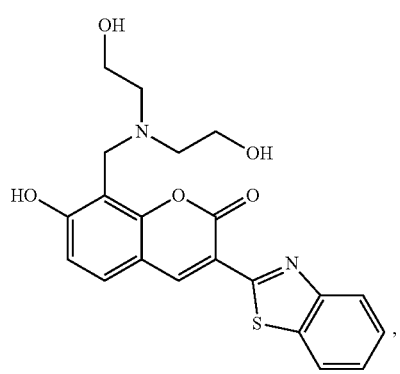

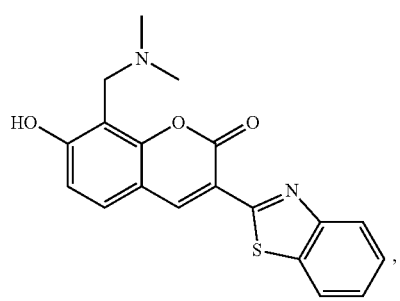

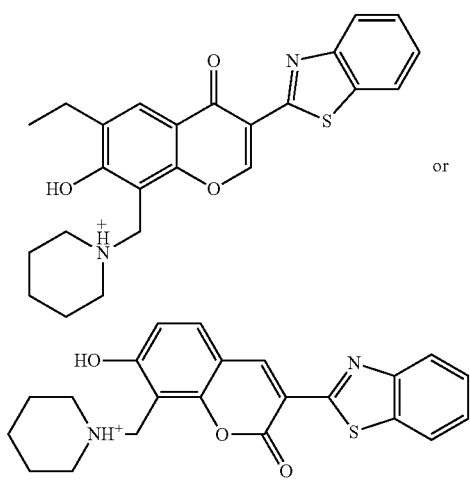

or a pharmaceutically acceptable salt thereof. In some embodiments, the compound has the structure:

or a pharmaceutically acceptable salt thereof.

In some embodiments, the composition is formulated for the treatment of a mammal. In some embodiments, the mammal is a human. In some embodiments, the pharmaceutical composition is formulated for intravenous, intraperitoneal, intratracheal, intratumoral, intramuscular, endoscopic, intralesional, percutaneous, subcutaneous, regional, direct injection, or perfusion administration.

In some embodiments, the pharmaceutical composition further comprises a second anti-cancer therapy or chemotherapeutic. The chemotherapeutic may be, e.g., doxorubicin, cyclophosphamide, docetaxel, paclitaxel, chlorambucil, gencitabine, 6-thioguanine, mercaptupurine, methotrexate, cisplatin, oxaliplatin, carboplatin, vinbastine, etoposide, vincristine, daunomycin, capecitabine, procarbazine, mechlorethamine, cyclophosphamide, camptothecin, bleomycin, busulfan, dactinomycin, tamoxifen, raloxifene, or 5-fluorouracil In another aspect, the present invention describes a compound of the formula:

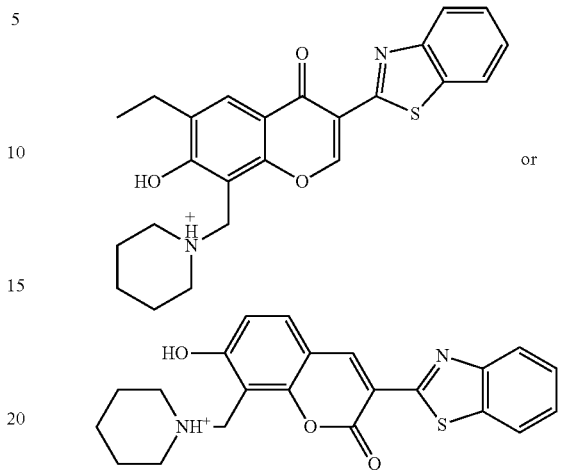

or a pharmaceutical salt thereof. In some embodiments, the pharmaceutical composition is formulated for intravenous, intraperitoneal, intratracheal, intratumoral, intramuscular, endoscopic, intralesional, percutaneous, subcutaneous, regional, direct injection, or perfusion administration.

The cancer can be any type of cancer. For example, the cancer may be oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendocrine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer or skin cancer. The cancer may be deficient in, or have a mutated or inactivated gene such as, e.g., p53, PTEN, ARF, pRB. The cancer may express or overexpress a gene such as, e.g., Her2/Neu. In some embodiments, the cancer has an inactivated, mutated, and/or deficient p53 gene. The cancer may comprise cancer stem cells or cancer initiating cells. In some embodiments, a Skp2 inhibitor may attenuate aerobic glycolysis or induce cellular senescence in cancer stem cells.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-I. Identification of the Skp2 inhibitor which impairs Skp2 SCF E3 ligase activity via preventing Skp2-Skp1 binding. (FIG. 1A) The identified potential binding pockets on the interface of Skp2-Skp1 complex. Skp2 is shown as molecular surface (light grey for carbon, dark gray for nitrogen, and gray for oxygen atoms). Skp1 is displayed in light and dark gray ribbon and stick form. The light gray region represents residues of Skp1 interacting with Skp2 in the two pockets. (FIG. 1B) In vitro Skp2-Skp1 binding assay with or without compound #25. (FIG. 1C) In vivo Skp2-Skp1 binding assay with or without compound #25 in PC3 cells. (FIG. 1D) In vivo p27 ubiquitination assay in 293T cells transfected with p27, His-Ub, along with Xp-Skp2 in the presence of DMSO or compound #25. WCE indicates whole cell extracts. (FIG. 1E) In vitro Skp2-mediated p27 ubiquitination assay was performed with or without Flag-Skp2-SCF or p27 in the presence of DMSO or compound #25. (FIG. 1F) PC3 cells were treated with DMSO or compound #25 at different doses for 24 h and harvested for immunoblotting (IB) assay. (FIG. 1G) In vivo Akt ubiquitination assay in 293T cells transfected with various constructs in the presence of DMSO or compound #25. (FIG. 1H) In vitro Skp2-mediated Akt ubiquitination assay was performed with or without Flag-Skp2-SCF or GST-Akt in the presence of DMSO or compound #25 (FIG. 1I) LNCaP cells were serum starved in the absence or presence of compound #25 for 24 h, stimulated with or without EGF and harvested for IB assay. See also FIG. 8.

FIGS. 2A-D. Skp2 inhibitor directly interacts with Skp2 at Trp97 and Asp 98 residues. (FIG. 2A) Chemical structure of compound #25. 3-(1,3-benzothiazol-2-yl)-6-ethyl-7-hydroxy-8-(1-piperidinylmethyl)-4H-chromen-4-one (upper panel). The docking between compound #25 (stick representation) and predicted pocket 1 of Skp2 (surface representation). The residues in gray form hydrogen bonding/hydrophobic/aromatic stacking interactions with compound #25. The dashed lines represent hydrogen bonds between compound #25 and Skp2 (lower panel). (FIG. 2B) In vivo Skp2-Skp1 binding assay in 293T cells transfected with Skp2 or its various mutants. (FIG. 2C) In vivo p27 ubiquitination assay in 293T cells transfected with various constructs in the presence of DMSO or compound #25. (FIG. 2D) In vitro binding of Skp1 with Skp2 WT or various mutants in the presence of DMSO or compound #25. (FIG. 2E) The extracted ion chromatography spectra demonstrating the quantity of compound #25 bound to GST alone, GST-Skp2 WT, W97A mutant and D98A mutant. The identity of the bound compound was further confirmed by MS/MS analysis as shown in FIG. 10. See also FIGS. 9 and 10.

FIGS. 3A-E. The Skp2 inhibitor specific diminishes E3-ligase activity of Skp2-SCF complex, but not of other F-box SCF complex. (FIGS. 3A-D) 293T cells transfected with various constructs in the presence of DMSO or compound #25 was treated with MG132 for 6 h followed by in vivo ubiquitination assay. (FIG. 3E) LNCaP cells were treated with DMSO, Skp2 inhibitors, or MLN4924 for 24 h, and harvested for IB assay. See also FIG. 11.

FIGS. 4A-H. Inhibition of E3-ligase activity of Skp2-SCF complex results in cancer cell death, glycolysis defects and cellular senescence. (FIG. 4A) Prostate cancer cells and normal epithelial cells (PNT1A) were treated with various doses of compound #25, followed by cell survival assay. (FIG. 4B) Lung cancer cells and normal fibroblasts (IMR90) were treated with various doses of compound #25, followed by cell survival assay. (FIG. 4C) PC3 cells were treated with or without compound #25 for 4 days and harvested for senescence assay. (FIGS. 4D-E) Lactate production was measured in PC3 (FIG. 4D) or LNCaP (FIG. 4E) cells treated with DMSO, LY294002 or compound #25. (FIG. 4F) Apoptosis rate was determined in PC3 cells treated with DMSO or compound #25. (FIGS. 4G-H) PC3 cells with or without Skp2 knockdown (FIG. 4G) or PC3 cells stably expressed with Skp2 WT, W97A or D98A mutants (FIG. 4H) were treated with various doses of compound #25, followed by cell survival assay. Cell survival percentage of each stable cell lines treated with various doses of compound #25 was normalized to that treated with DMSO. Results are presented as mean values±S.D. * indicates $p<0.05$, ** indicates $p<0.01$. See also FIG. 12 and FIG. 13.

FIGS. 5A-E. The structure-activity relationship (SAR) of compound #25 derivatives. (FIGS. A-B) In vitro Skp2-Skp1 binding assay in the presence of DMSO, compound #25 or its derivatives. (FIG. 5C) SAR of compound #25 and its derivatives. #25-5 is illustrated separately due to its unique core structure. (FIG. 5D) In vivo p27 ubiquitination assay in 293T cells transfected with various constructs in the presence of DMSO, compound #25 or its derivatives with MG132 treatment. (FIG. 5E) PC3 cells were treated with various doses of compound #25 or its derivatives, followed by cell survival assay.

FIGS. 6A-G. Skp2 inactivation diminishes cancer stem cell properties and heightens cancer cell sensitivity to chemotherapy. (FIG. 6A) Populations of ALDH+ cells were determined by FACS analysis in PC3 cells treated with vehicle or compound #25. (FIG. 6B) Populations of ALDH+ cells were determined by FACS analysis in PC3 cells with control or Skp2 knockdown. (FIG. 6C) Populations of ALDH+ cells were determined by FACS analysis in PC3 cells with control or Skp2 knockdown treated with vehicle or compound #25. (FIG. 6D) Populations of ALDH+ cells were determined by FACS analysis in PC3 cells with DMSO or LY294002. (FIG. 6E) Populations of ALDH+ cells were determined by FACS analysis in LNCaP cells treated with DMSO, LY294002 or compound #25. (FIGS. 6F-G) Prostate sphere-formation assay in PC3 (FIG. 6F) and LNCaP (FIG. 6G) cells treated with DMSO, LY294002 or compound #25. Results are presented as mean values±S.D. ** indicates $p<0.01$.

FIGS. 7A-G. Skp2 inhibitor suppresses tumor growth in human tumor xenografts. (FIGS. 7A-B) PC3 cells in the absence or presence of compound #25 were treated with Dox (FIG. 7A) or CPA (FIG. 7B), followed by cell survival assay. (FIGS. 7C-D) Nude mice bearing A549 (FIG. 7C) or PC3 (FIG. 7D) tumor xenografts were administration with or without compound #25 via IP injection Mean tumor volumes±s.d. are shown. n=6 mice per group. (FIGS. 7E-F) The quantification results (FIG. 7E) and representative images (FIG. 7F) of histological analysis of p27, p21, pAkt, and Glut1 in PC3-induced tumor xenografts. "Low" indicates 40 mg/kg; "high" indicates 80 mg/kg of compound #25 were injected into mice. Scale bar indicates 100 µm. (FIG. 7G) The working model depicts how Skp2 inhibitor prevents Skp2-SCF complex formation and results in tumor suppression. Results are represented as mean values±S.D. * indicates $p<0.05$, ** indicates $p<0.01$. See also FIG. 14.

FIGS. 8A-F. Identification of Skp2 inhibitor and examination of its inhibitory effect on Skp2, related to FIG. 1. (FIG. 8A) The high-throughput virtual screening workflow for lead identification. Different colors represent different stages of the development. (FIGS. 8B-C) PC3 cells were serum starved in the absence or presence of compound #25 for 24 h, stimulated with or without EGF at various time points and harvested for IB assay. (FIG. 8D) PC3 cells with control or Skp2 silencing were serum starved for 24 h, stimulated with or without EGF at various time points and harvested for IB assay. (FIG. 8E) Real-time PCR analysis of Skp2 mRNA levels in PC3 cells in the presence of DMSO or compound #25 followed by the treatment with or without MG132. (FIG. 8F) IB analysis of Skp2 protein levels in PC3 cells in the presence of DMSO or compound #25 followed by the treatment with or without MG132.

FIGS. 9A-C. $^1$H, $^{13}$C-NMR and LC-MS/MS analysis of Skp2 inhibitor, related to FIG. 2. $^1$H-NMR (FIG. 9A) and $^{13}$C-NMR (FIG. 9B) spectral images of compound #25. (C) LC-MS/MS analysis on a triple quadrupole mass spectrometer of compound #25.

FIGS. 10A-B. LC-MS/MS analysis of the interaction between compound #25 and Skp2 WT or mutants, related to FIG. 2. (FIG. 10A) Left: The workflow illustrated the preparation procedures of protein samples subjected to LC-MS/MS analysis. Right: Coomassie brilliant blue staining showed that WT or mutants of recombinant Skp2 proteins formed complex with Skp1A. (FIG. 10B) The identity of compound #25 bound to GST-Skp2 WT, GSTSkp2 W97A, and GST-Skp2 D98A mutants as shown in FIG. 2E was characterized by LC-MS/MS analysis on an Orbitrap-Elite mass spectrometer.

FIG. 11A-B. Skp2 inhibitor selectively stabilizes substrates of Skp2, but not of other F-box proteins, related to FIG. 3. (FIG. 11A) IB analysis of PC3 cells treated with cyclohexamide (CHX) for various time points in the presence of DMSO or compound #25. (FIG. 11B) In vivo ubiquitination assay in 293T cells transfected with c-Jun, His-Ub, along with Flag-Fbw7 in the presence of PBS or MLN4924 with MG132 treatment.

FIGS. 12A-D. Skp2 inhibitor triggers cell growth suppression and cell cycle arrest at G2/M phase, related to FIG. 4. (FIG. 12A) The impact of Skp2 inhibitor on growth suppression in various cell lines. A panel of cancer cell lines were treated with various doses of Skp2 inhibitor (#25) for 4 days, and viable cell numbers were counted using hemocytometer. Growth inhibition ($IC_{50}$) by compound #25 was derived from the cell counting using hemocytometer. (FIG. 12B) PC3 cells were treated with or without compound #25 for 2 days and cell cycle were determined by PI staining, followed by flow cytometry analysis. G1 phase=61.3±0.3%, S phase=15.6±0.6% and G2/M phase=20.3±0.3% in DMSO-treated PC3 cells while G1 phase=50.1±0.9%, S phase=13.3±0.8% and G2/M phase=24.5±0.3% in #25-treated PC3 cells. (FIG. 12C) Control- or Skp2-knockdown PC3 cells were treated with or without compound #25 for 2 days and cell cycle were determined by PI staining, followed by flow cytometry analysis. Two clones of Skp2 shRNA were used in this assay. G1 phase=53.1±0.8% and S phase=15.9±0.9% and G2/M phase=26.1±0.6% in control-knockdown PC3 cells, G1 phase=49.5±0.4%, S phase=13.6±0.7% and G2/M phase=29.1±0.5% in one clone of Skp2-silenced PC3 cells, G1 phase=54.5±1.6%, S phase=10.6±0.4% and G2/M phase=28.8±0.2% in another clone of Skp2-silenced PC3 cells. (FIG. 12D) WT or $Skp2_{-/-}$ MEFs were treated with or without compound #25 for 2 days, and cell cycle was determined by PI staining, followed by flow cytometry analysis. G1 phase=50.5±4.6%, S phase=9.1±0.6% and G2/M phase=27.8±0.9% in WT MEFs while G1 phase=27.7±1.3%, S phase=8.2±1.9% and G2/M phase=39.0±1.6% in $Skp2_{-/-}$ MEFs. Results are presented as mean values ±S.D. * indicates $p<0.05$, ** indicates $p<0.01$. Results from treatment groups were compared to vehicle-treated group.

FIGS. 13A-D. Skp2 inhibitor triggers cellular apoptosis, related to FIG. 4. (FIG. 13A) PC3 cells were cultured in 10% FBS with or without Skp2 inhibitor for 3 days, and apoptosis was determined by annexin V and PI staining, followed by flow cytometry analysis. (FIG. 13B) LNCaP cells were cultured in 10% FBS with or without Skp2 inhibitor for 3 days, and apoptosis was determined by annexin V staining, followed by flow cytometry analysis. Results are presented as mean±SD. ** indicates $p<0.01$. Results from treatment groups were compared to vehicle-treated group. (FIG. 13C) IB analysis of Skp2 protein levels in control and Skp2-silenced PC3 cells. Two clones of Skp2 shRNA were used in this assay. (FIG. 13D) IB analysis of Skp2 protein levels in PC3 cells overexpressing mock, Skp2 WT, Trp97Ala (W97A) mutant, or Asp98Ala (D98A) mutant.

FIGS. 14A-C. Skp2 inhibitor restricts cancer cell proliferation and triggers apoptosis in prostate tumor xenografts. The quantification results (FIG. 14A) and representative images (FIG. 14B) of histological analysis of Ki-67, TUNEL, Skp2 and HE staining in PC3-driven tumor xenografts. "Low" indicates tumor xenografts treated with 40 mg/kg, while "high" indicates the xenografts treated with 80 mg/kg of compound #25. Scale bar indicates 100 µm. (FIG. 14C) Pharmacokinetic analysis of compound #25. Plasma and tumor distribution following IP injection of compound #25 to nude mice bearing PC3-driven tumor xenograft are analyzed. Three mice were evaluated at each time point. Results are represented as mean values±S.D.

DESCRIPTION OF ILLUSTRATIVE EMBODIMENTS

Figure 15:
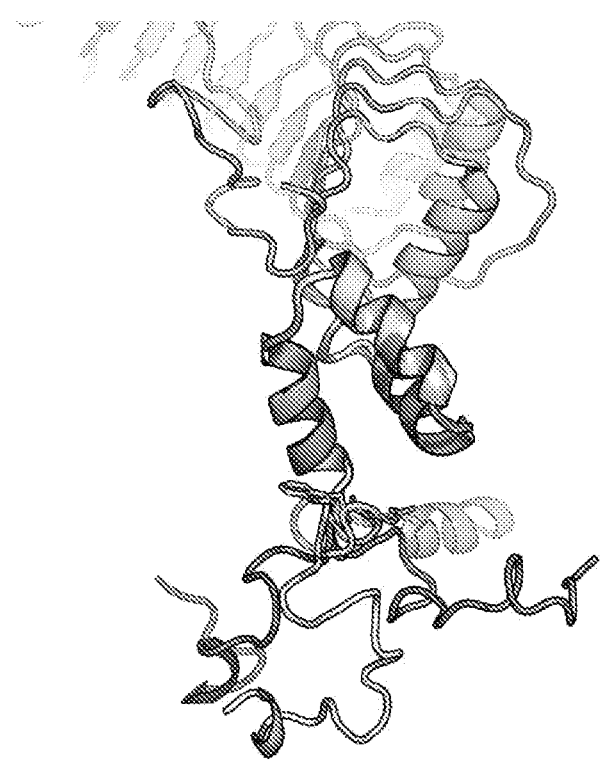
FIG. 15. Proposed Skp2 model. Without wishing to be bound by any theory, several proposed models of Skp2 with more Fbox n-terminal residues that are close to the inhibitor binding pocket are shown. The crystal structure is included in the proposed structural model.

In various aspects, the present invention overcomes limitations in the prior art by providing new anti-cancer compounds and methods of treating cancer. In some embodiments, Skp2 inhibitors have been identified that may be used to treat or reduce the recurrence of a cancer in a subject, such as a human patient.

Skp2 E3 ligase overexpressed in numerous human cancers plays a critical role in cell cycle progression, senescence, metabolism, cancer progression and metastasis. As shown in the below examples, selective Skp2 inhibitors were identified using high-throughput in silico screening of large and diverse chemical libraries. In some aspects, a Skp2 inhibitor provided herein may selectively suppress Skp2 E3 ligase activity, but not activity of other SCF complexes, and phenocopies the effects observed upon the genetic Skp2 deficiency, such as suppressing survival, Akt-mediated glycolysis as well as triggering p53-independent cellular senescence. In some embodiments, the Skp2 inhibitor may reduce or prevent Skp2-promoted Akt ubiquitination and/or reduce glycolysis, e.g., in cancer cells. In some embodiments, the Skp2 inhibitor may impair survival of or kill cancer cells via promoting cell cycle arrest or apoptosis. A role of Skp2 was discovered in positively regulating cancer stem cell populations and self-renewal ability through genetic and pharmacologic approaches. In some embodiments, the Skp2 inhibitor may inhibit growth of cancer stem cells. Skp2 inhibitors were found to exhibit potent anti-tumor activities in multiple animal models and may be used in combination with chemotherapeutic agents to reduce cancer cell survival. These studies provide pharmacologic evidence that Skp2 targeting can be used to restrict cancer stem cell and/or cancer progression.

I. Chemical Group Definitions

When used in the context of a chemical group, "hydrogen" means —H; "hydroxy" means —OH; "oxo" means =O; "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "$\equiv$" represents a single bond or a double bond. Thus, for example, the structure

includes the structures

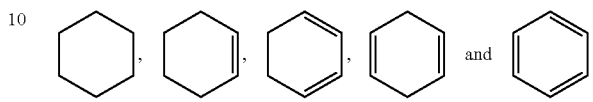

As will be understood by a person of skill in the art, no one such ring atom forms part of more than one double bond. The symbol "$\sim$", when drawn perpendicularly across a bond indicates a point of attachment of the group. It is noted that the point of attachment is typically only identified in this manner for larger groups in order to assist the reader in rapidly and unambiguously identifying a point of attachment. The symbol "◀" means a single bond where the group attached to the thick end of the wedge is "out of the page." The symbol "⦀" means a single bond where the group attached to the thick end of the wedge is "into the page". The symbol "$\sim$" means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

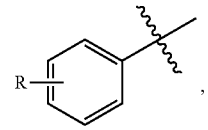

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

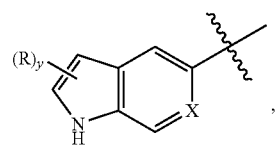

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$," or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (ten-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

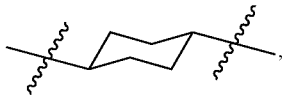 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CH—C$_6$H$_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

are non-limiting examples of alkenediyl groups. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —CH=CHF, —CH=CHI and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. When alkynyl is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

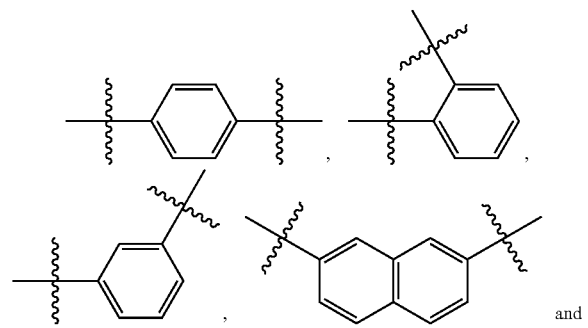

and

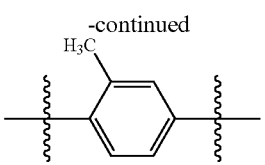

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

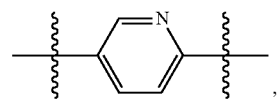

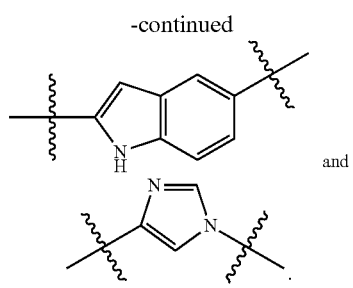
and

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, C(O)CH$_2$CH$_2$CH$_3$, C(O)CH(CH$_3$)$_2$, C(O)CH(CH$_2$)$_2$, C(O)C$_6$H$_5$, C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "dialkylphosphate" when used without the "substituted" modifier refers to the group —OP(O)(OR)(OR'), in which R and R' can be the same or different alkyl groups, or R and R' can be taken together to represent an alkanediyl. Non-limiting examples of dialkylphosphate groups include: —OP(O)(OMe)$_2$, —OP(O)(OEt)(OMe) and —OP(O)(OEt)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, an enzyme, cell, cell receptor, or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, -[—$CH_2CH_2$—]$_n$—, the repeat unit is —$CH_2CH_2$—. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in metal organic frameworks, modified polymers, thermosetting polymers, etc.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC($CH_3$)$_3$), benzyloxycarbonyl, p-methoxybenzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC($CH_3$)$_3$), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC($CH_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Compounds of the Invention

The compounds provided by the present disclosure are shown, for example, above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a structure are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference. In some aspects, one or more compounds described herein, for example, above in the summary of the invention section and in the claims below may be included in a pharmaceutical preparation.

While the exact approach for the synthesis of molecules to be tested will be dependent on the chemical structures that come out of the in silico screening. For the lead compound SZL-P1-41 (#25), the synthesis can begin with the assembly of the appropriately substituted 2-methyl benxothiazoles 8 and 9 as outlined in Scheme 1 using the methodology of Kozikowski et al. (Huang, et al., 2009; Kashiyama, et al., 1999; Mathis, et al., 2003). Treatment of 3-methoxy-aniline 1 or 2-methyl aniline 2 with acetic anhydride/pyridine will afford the corresponding benzanilides 3 and 4. Subsequent treatment of the amides with Lawesson's reagent in refluxing chlorobenzene will give the corresponding thiobenzanilides 5 and 6. Cyclization to the corresponding substituted 2-methylbenzothiazoles 8 and 9 will be accomplished by treatment with potassium ferricyanide in aqueous NaOH. 2-methylbenzothiazole 7 is commercial available and can be used as received. Construction of the appropriately substituted amino isoflavones 32-35 is outlined in Scheme 2. Esterification (Hadj-esfandiari, et al., 2007) of salicylic acid derivatives 10 and 11 with sulfuric acid/ethanol will provide the prerequisite ethyl salicylates 12 and 13. At this point the hydroxyl group will be protected as the tert-butyldimethylsilyl ether 14 and 15 using standard methodology (Lee et al., 2004). With the fully protected ethyl salicylates 14 and 15 in hand, a condensation of the appropriately substituted 2-methylbenzothiazoles 7-9 will be performed (Scheme 1), using lithiated methylbenzothiazoles 7-9 with n-BuLi at −78° C., with the previously prepared ethyl salicylates 14 and 15, using the methodology of Costa et al. (1991) to afford the corresponding condensation products 16-19. De-tert-butylsilylation will be achieved by brief treatment with tetrabutylammonium fluoride (TBAF) will afford the corresponding substituted 2-hydroxydeoxybenzoin compounds 20-23. Cyclization of 20-23 can be accomplished using a modified Venkataraman reaction (Gao, et al., 2003; Gulati, et al., 1943; Nussbaumer, et al., 2002). Treatment with triethyl orthoformate/morpholine/isopropanol at 80° C. affords the isoflavones 24-27. Global demethylation will be accomplished using the methodology of Wang et al. (Ding and Wang, 2005). Thus treatment of 24-27 with boron tribromide at −78° C. and slowly raising the reaction to room temperature will afford the substituted isoflavones 28-31. The benzothiazole moiety of the isoflavones will be stable to conditions of global demethylation as previously observed by Kozikowski et al (Huang, et al., 2009). Final aminomethylation of the substituted isoflavones 28-31 to afford the corresponding N-substituted aminomethyl isoflavones 32-35 will be accomplished by using the methodologies of Frasinyuk et al. (1998) or Liu et al. (2007).

Scheme 1

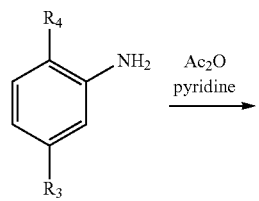

1 $R_3 = CH_3O$, $R_4 = H$
2 $R_3 = H$, $R_4 = CH_3$

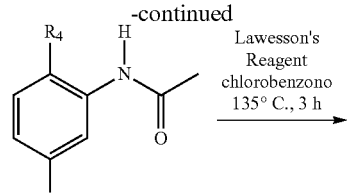

3 $R_3 = CH_3O$, $R_4 = H$
4 $R_3 = H$, $R_4 = CH_3$

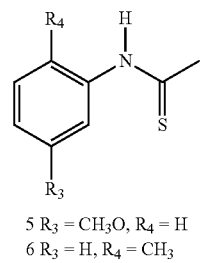 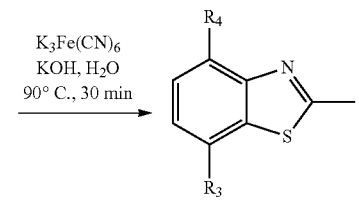

5 $R_3 = CH_3O$, $R_4 = H$
6 $R_3 = H$, $R_4 = CH_3$

8 $R_3 = CH_3O$, $R_4 = H$
9 $R_3 = H$, $R_4 = CH_3$

Scheme 2

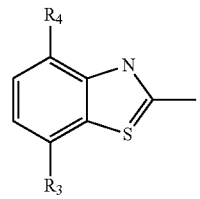

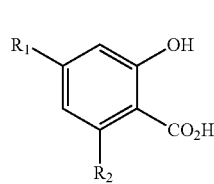 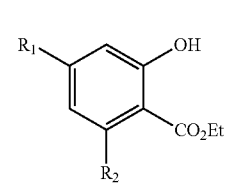 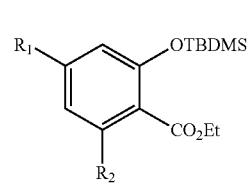

10 $R_1 = CH_3O$, $R_2 = H$
11 $R_1 = CH_3O$, $R_2 = CH_3O$

12 $R_1 = CH_3O$, $R_2 = H$
13 $R_1 = CH_3O$, $R_2 = CH_3O$

14 $R_1 = CH_3O$, $R_2 = H$
15 $R_1 = CH_3O$, $R_2 = CH_3O$ n-BuLi, THF
-78° C., 1 h
7 $R_3 = R_4 = H$
8 $R_3 = CH_3O$, $R_4 = H$
9 $R_3 = H$, $R_4 = CH_3$

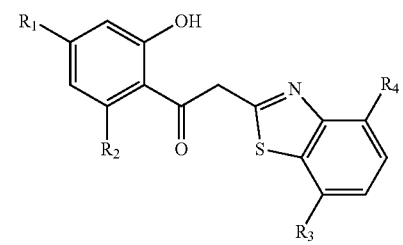

16 $R_1 = CH_3O$, $R_2 = H$, $R_3 = R_4 = H$
17 $R_1 = CH_3O$, $R_2 = H$, $R_3 = OCH_3$, $R_4 = H$
18 $R_1 = CH_3O$, $R_2 = H$, $R_3 = H$, $R_4 = CH_3$
19 $R_1 = CH_3O$, $R_2 = CH_3O$, $R_3 = R_4 = H$

TBAF, THF
rt, 1 hr

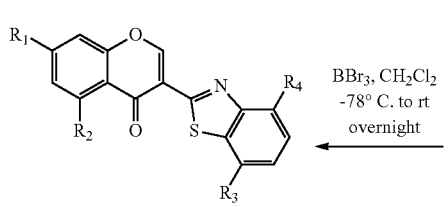
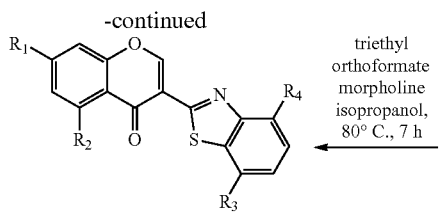
-continued
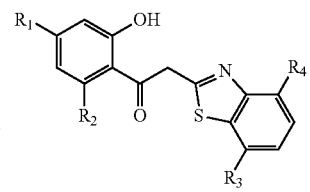

28 R₁ = OH, R₂ = H, R₃ = R₄ = H
29 R₁ = OH, R₂ = H, R₃ = OH, R₄ = H
30 R₁ = OH, R₂ = H, R₃ = H, R₄ = CH₃
31 R₁ = OH, R₂ = OH, R₃ = R₄ = H

24 R₁ = CH₃O, R₂ = H, R₃ = R₄ = H
25 R₁ = CH₃O, R₂ = H, R₃ = OCH₃, R₄ = H
26 R₁ = CH₃O, R₂ = H, R₃ = H, R₄ = CH₃
27 R₁ = CH₃O, R₂ = CH₃O, R₃ = R₄ = H

20 R₁ = CH₃O, R₂ = H, R₃ = R₄ = H
21 R₁ = CH₃O, R₂ = H, R₃ = OCH₃, R₄ = H
22 R₁ = CH₃O, R₂ = H, R₃ = H, R₄ = CH₃
23 R₁ = CH₃O, R₂ = CH₃O, R₃ = R₄ = H

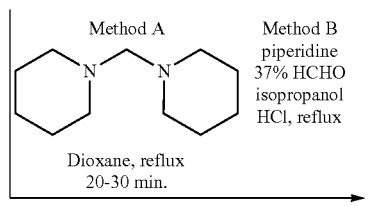
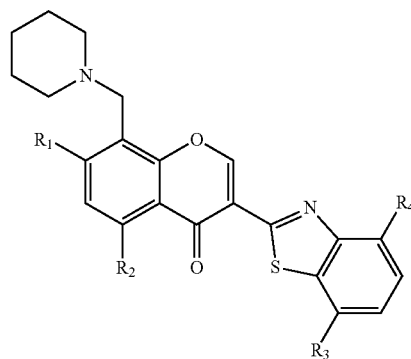

32 R₁ = OH, R₂ = H, R₃ = R₄ = H
33 R₁ = OH, R₂ = H, R₃ = OH, R₄ = H
34 R₁ = OH, R₂ = H, R₃ = H, R₄ = CH₃
35 R₁ = OH, R₂ = OH, R₃ = R₄ = H

Synthetic schemes to build focused libraries of lead SZL-P1-41 (#25). Scheme 1 (upper): 2-methyl benxothiazoles. Scheme 2 (bottom): synthesis of SZL-P1-41 derivatives.

III. Pharmaceutical Compositions

Pharmaceutical compositions of the present invention comprise an effective amount of one or more compounds of the present invention, e.g., a Skp2 inhibitor, or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one compound or Skp2 inhibitor or additional active ingredient will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The compound or Skp2 inhibitor of the present invention may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The compound or Skp2 inhibitor of the present invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include a compound or Skp2 inhibitor of the present invention, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the compound or Skp2 inhibitor of the present invention may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the compound or Skp2 inhibitor of the present invention are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, a compound or Skp2 inhibitor of the present invention may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound or Skp2 inhibitor may be formulated for administration via various miscellaneous routes, for example, topical or transdermal administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described, e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroethylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

IV. Diseases

The present invention can find application in the treatment of any disease for which delivery of a therapeutic nucleic acid to a cell or tissue of a subject is believed to be of therapeutic benefit. Examples of such diseases include hyperproliferative diseases, inflammatory diseases, infectious diseases, degenerative diseases, diabetes, and autoimmune diseases. In some embodiments, the disease is cancer. The cancer may express or overexpress Skp2 relative to a healthy tissue. In some embodiments, a Skp2 inhibitor of the present invention may be used to treat a metabolic disorder such as, e.g., obesity or diabetes.

For example, a compound of the present invention may be administered to treat a cancer. The cancer may be a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, prostate, skin, stomach, testis, tongue, or uterus. In certain embodiments, the cancer is a lymphoma, prostate cancer, or a breast cancer. The cancer may be deficient in gene such as, e.g., p53. For example, the cancer cell may underexpress, comprise one or more mutation(s) in, or have an inactivated p53. The cancer may comprise cancer stem cells.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Nonetheless, it is also recognized that the present invention may also be used to treat a non-cancerous disease (e.g., a fungal infection, a bacterial infection, a viral infection, and/or a neurodegenerative disease).

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Binding Pocket Identification on the Skp2-Skp1 Interface

Due to the large interface between Skp2 and Skp1, visualization analysis and literature report searches were performed to identify residues of Skp2 in contact with Skp1 (Frescas and Pagano, 2008; Hao et al., 2005; Schulman et al., 2000). The Site Finder module in software MOE (MOE v2010, Chemical Computing Group, Montreal, Canada) was used to predict potential small molecule binding pockets. To further refine the definition of the binding pockets and identify hot spot residues, specific hot spot prediction tools including FTMAP (Brenke et al., 2009) and HotPoint (Tuncbag et al., 2010) were used. Combining all of these results, the inventors grouped Skp1-Skp2 contact sites into two pocket-like and distinct regions, as demonstrated in FIG. 1A.

Lead Identification Using High-Throughput Virtual Screening

The two identified pockets in the Skp2-Skp1 complex structure (FIG. 1A) were screened separately with the high-throughput docking program HiPCDock. FIG. 8A illustrates the overall in silico screening procedure. The inventors first focused on commercially available compounds (ca. 120,000 compounds) and performed docking with rigid Skp2 structure. The top scored 20,000 compounds were clustered based on their chemical diversity (Tanimoto coefficient<70%), and the top 1,000 clusters were retained. The representative compounds (the best scored) from each cluster were selected for precision docking using GOLD software. Skp2 flexibility was addressed using both GOLD and normal mode analysis protocols (Du-Cuny et al., 2009; Tran and Zhang, 2011). The inventors selected the top 200 hits for ADMET analysis as described elsewhere (Du-Cuny et al., 2009; Zhang et al., 2007). These 200 hits were also individually inspected for their interactions with Skp2 target. The qualified hits (high docking scores, reasonable binding poses, MWT<500, Log P<5, no hERG inhibition, etc.) were then subjected to evaluations by examining their effect on Skp2-Skp1 disruption.

Cell Culture and Reagents

293T, PC3, A549, H460, H1299, Hep3B and U2OS cells were cultured in DMEM containing 10% fetal bovine serum (FBS) while LNCaP and H3255 were cultured in RPMI-1640 medium containing 10% fetal bovine serum (FBS). $(His)_6$-ubiquitin, GST-Akt, and HA-Akt constructs was described previously (Yang et al., 2009). Flag-Skp2 was a gift from Dr. W. Wei. LY294002 was purchased from Cell signaling.

Immunoblotting Analysis and Immunohistochemistry

Cells were lysed with RIPA buffer in the presence of protease inhibitor cocktail (Roche). The following antibodies were used for immunoblotting analysis: anti-Skp2 (Invitrogen), anti-Xpress (Invitrogen), anti-p27 (BD transduction laboratories), anti-p21 (Santa Cruz), anti-β-actin (Sigma), anti-α-tubulin (Sigma), anti-phospho-Akt (Thr308) (Cell Signaling), anti-phospho-Akt (Ser473) (Cell Signaling), and anti-HA (Convance). For immunohistochemistry, tissues were fixed in 10% formalin and embedded in paraffin in accordance with standard procedures. Sections were stained with anti-Skp2 (Invitrogen), anti-p27 (Epitomics), anti-phosphoAkt (SerS473) (Cell signaling), anti-Glut1 (Abcam), and anti-Ki67 (Abcam). TUNEL staining was performed by using in situ cell death detection kit-POD (Roche).

In Vitro Binding Assay

For in vitro GST-Skp1 and Skp2 interaction, GST-Skp1 proteins purified from the bacterial lysates of BL21 competent cells transformed with pGEX-4X1-Skp1 using the Glutathione-Agarose beads according to the manufacturer's standard procedures. The GST-Skp1 proteins bound to glutathione Sepharose beads (Amersham Biosciences) were then incubated with the in vitro translated [$35^S$]-Skp2 for 2 hours at 4° C. in the interaction buffer with or without compound #25 (20 mM HEPES, PH 7.9, 150 mM KCl. 5 mM EDTA, 0.5 mM DTT, 0.1% (v/v) Nonidet p-40, 0.1% (w/v) BSA, 1 mM PMSF, and 10% Glycerol), washed by the NETN buffer (20 mM Tris, pH 8.0, 100 mM NaCl, 6 mM MgCl2, 1 mM EDTA, 0.5% Nonidet P-40, 1 mM DTT, 8% glycerol, 1 mM PMSF) 4 times, and subjected to 8% SDS-PAGE, followed by autoradiography.

In Vitro and In Vivo Ubiquitination Assay

In vivo and in vitro ubiquitination assays were performed as described with modification (Lin et al., 2009; Yang et al., 2009). For in vitro ubiquitination assay, recombinant GST-Akt proteins were expressed, purified and eluted from the bacterial lysates of BL21 competent cells. Flag-Skp2 SCF complex were expressed in 293T cells, immunoprecipitated by anti-Flag antibody, and eluted from Protein A/G beads using Flag peptides according to manufacturers' standard procedures. Purified GST-Akt and Flag-SCF proteins were incubated for 3 h at 37° C. in the absence and presence of Skp2 inhibitor. After incubation, protein mixtures were diluted in E1A Buffer and the supernatant fluid was precleared with Protein A/G beads for 1 h, and immunoprecipitated overnight with anti-Flag antibody, after which Protein A/G beads were added for an additional 1 h. Beads were washed 4 times with E1A Buffer. Proteins were eluted in SDS-sample buffer and subjected to immunoblotting analysis. For in vivo ubiquitination assay, 293T cells were transfected with the indicated plasmids and cultured in the absence or presence of Skp2 inhibitor for 48 h. 6 h before harvest, cells were cultured in the presence of MG132. After cell harvest, cells were lysed by the denatured buffer (6M guanidine-HCl, 0.1M $Na_2HPO_4$/$NaH_2PO_4$, 10 mM imidazole). The cell extracts were then incubated with nickel beads for 3 h, washed, and subjected to immunoblotting analysis.

Cell Growth and Cell Senescence Assay

For Skp2 inhibitor administration, 5-10×$10^3$ of cells with were seeded in 12 wells in triplicate, 24 h later, treated with compound #25 (refreshed every two days). Four days later, cells were harvested, stained with trypan blue, and viable cells were counted directly under the microscope using hemocytometer. For doxorubicin treatment, 8×$10^3$ of PC3 cells with were seeded in 12 wells in triplicate, 24 h later, treated with various dose of compound #25 in the presence or absence of 10 nM doxorubicin or 25 ng/ml cyclophosphamide for four and three days, respectively (refreshed every two days). After treatment, cells were harvested, stained with trypan blue, and viable cells were counted directly under the microscope using hemocytometer. Cellular senescence was determined by assessing SA-b-gal activity using senescence detection kit according to manufacturers' standard procedures (Calbiochem).

Lactate Production

Prostate cancer cells were plated in 24-well plate and cultured overnight. After serum starvation along with pretreatment of 10 μM LY294002 or Skp2 inhibitor, cells were treated with EGF for 16 h. Culture medium was removed from cells and lactate concentration was determined using lactate test strips and Accutrend Lactate analyzer (Accutrend Lactate, Roche). Next, cells were harvested, stained with trypan blue and viable cell numbers were counted directly under the microscope using hemocytometer. Finally, the rate of lactate production were determined (lactate production rate=lactate concentration/cells/time) and normalized with the rate detected in control group.

Cell Apoptosis Assay

Prostate cancer cells were treated with vehicle (DMSO) or Skp2 inhibitor for 3 days, and collected and labeled with Annexin-V-FITC, followed by flow cytometry analysis. The Annexin-V+ and PC cells indicates apoptotic cell population (Q4).

In Vivo Drug Treatment in the Preclinical Tumor Model

Nude mice bearing PC3 or A549 xenograft tumors (around 100 $mm^3$) were administered with vehicle or 80 mg/kg compound #25 on a daily basis. Tumor size was measured weekly with a caliper, and tumor volume was determined with the standard formula: L×W2×0.52, where L is the longest diameter and W the shortest diameter.

Example 2

Pharmacological Skp2 Inactivation Restricts Cancer Stem Cell Traits and Cancer Progression As shown in the below example, specific Skp2 small molecule inhibitors were identified and shown to produce an effect on tumor suppression. Using rigorously validated structure-based high-throughput virtual screening technologies (Zhang, 2011), multiple compounds were identified that may associate directly with Skp2 to block its interaction with Skp1. Further experiments showed that a select compound disrupts Skp2/Skp1 interaction and inhibits Skp2 SCF E3 ligase activity, leading to inhibiting cancer cell and cancer stem cell growth, and survival. More importantly, the lead compound also exhibited potent anti-tumor activity in the animal studies. These experiments provide evidence that pharmacological inactivation of Skp2 may be a particularly effective approach for cancer treatment.

Identification of Small Molecule Inhibitors of Skp2 Using High-Throughput in Silico Screening Approaches.

Skp2 belongs to the family of F-box proteins and function as substrate recognition factors for SCF E3 ubiquitin-ligase complexes. It contains 424 residues with the F-box domain lying closer to the N-terminal region at the 94-140 position, and the C-terminal region forms a concave surface consisting of ten leucine-rich repeats (LRRs). After the tenth LRR, the ~30-residue C-terminal tail turns back towards the first LRR, forming what has been referred to as a 'safety-belt' that might aid to pin down substrates into the concave surface formed by the LRRs (Gohlke et al., 2000). The crystal structure of Skp2-SCF complex (PDB entry code: 2AST), demonstrated that Skp2 directly interacts with Skp1 via its F-box domain and indirectly associates with Cullin-1 and Rbx1 (Hao et al., 2005; Schulman et al., 2000; Zheng et al., 2002b). As expected, deletion of the F-box compromises Skp2 SCF E3 ligase activity (Carrano et al., 1999; Kim et al., 2003; von der Lehr et al., 2003).

Skp2 and Skp1 form a large Skp2-Skp1 interaction interface (2,980 $Å^2$) (Frescas and Pagano, 2008; Hao et al., 2005; Schulman et al., 2000). Along this interface, some residues contribute more significantly to binding than others; these residues are called hot spots. Based on visualization analysis, literature reports, and as hot spot analysis, the inventors found that there are 19 residues on Skp2 in contact with Skp1. The critical Skp2-Skp1 contact sites were grouped into two pocket-like and distinct regions (FIG. 1A). The first region (referred as pocket 1) is close to the N-terminus of Skp2 and is actually within the F-box motif including Trp97, Phe109, Glu116, Lys119, and Trp127. The second region (referred as pocket 2) has proximity to the corresponding C-terminus of Skp2, formed by the first LRR region and some residues from the F-box (FIG. 1A). These residues were predicted as the most critical to the Skp2-Skp1 interactions. Therefore inhibitors binding to these two pockets would potentially disrupt the Skp2-Skp1 complex.

Based on the above predicted potential binding pockets, high-throughput virtual screening was performed with a rigorously validated hit identification workflow which was employed to successfully develop lead compounds for various targets (FIG. 8A) (Ahad et al., 2011; Mahadevan et al., 2008; Yadav et al., 2012). 120,000 diverse, commercially available chemical compounds were screened using HiPC-Dock and GOLD docking programs, and selected 27 hits that were predicted to exhibit strong binding to Skp2 (FIG. 8A). Among them, 18 hits were predicted to interact with pocket 1 and 11 hits bind to pocket 2. During the selections of these hits, the inventors considered not only the predicted binding affinities, but also various other drug-likeness properties such as solubility and molecular weight. Without wishing to be bound by any theory, the inventors anticipate that by interacting with either (or both) of these two sites, the hits may block the binding of Skp1 to Skp2 and thereby resulting in deconstruction of Skp2 SCF complex (FIG. 1A).

Skp2 Small Molecule Inhibitors Disrupt Skp2-Skp1 Interactions and Skp2 SCF E3 Ligase Activity In Vitro.

To test the hypothesis generated in silico, in vitro GST-pull down assay was performed to assess which compounds from the 27 hits can disrupt Skp2 and Skp1 interactions. 7 out of 27 compounds demonstrated strong inhibition of forming Skp2-Skp1 complex at 20 μM. Next, these 7 compounds were subjected for in vitro Skp2-Skp1 binding assay at lower concentration (5 μM) in order to identifying more potent Skp2 inhibitors (FIG. 1B). Strikingly, it was revealed that SZL-P1-41 (referred as #25) could completely disrupt Skp2-Skp1 interaction at this concentration (FIG. 1B). It should be noted that another compound SZL-P1-35 (referred as #22) also reduced Skp2-Skp1 complex formation, albeit to a lesser extent compared to compound #25 (FIG. 1B). Interaction between Skp2 and Skp1 is prerequisite for the integrity of Skp2 SCF complex and is crucial for executing its E3 ligase activity (Schulman et al., 2000; Zheng et al., 2002b). Thus, this data illustrated that this small molecule identified via high-throughput in silico screening approach indeed disrupts Skp2-Skp1 association.

The inventors focused on compound #25 as it demonstrated promising results in disrupting Skp2-Skp1 complex in vitro (FIG. 1B). The chemical structure of #25 is disclosed in FIG. 1C, and it (magenta sticks in FIG. 2A) binds to Skp2 pocket 1 via strong hydrogen bonding and hydrophobic interactions with key several residues. The benzothiazole substructure interacts with residue Trp97 via hydrogen bonds and aromatic stacking effect. Interestingly, it is also close to a hydrophobic pocket consisting of Trp97, Leu105, Ile108, Trp127 and several other residues (FIG. 2A). Potentially, interaction with this hydrophobic pocket can increase the binding. The other part of the inhibitor is the chromenone moiety which is frequently found in flavones/flavonoids (Wu et al., 2011a; Wu et al., 2011b). This chromenone core, along with its substitutions (hydroxyl and ethyl groups) on the benzene ring, is extended through the channel formed by the F-box domain of Skp2. It forms strong interactions with several residues including Asp98, Arg126 and Trp127 via either hydrogen bonds or hydrophobic interactions. The piperidinyl group does not appear to interact with any part of the Skp2 structure. As comparison, the pocket 2 inhibitors (such as inhibitor #25) exhibit very different core scaffolds. They bind to pocket 2 mainly via interactions with Trp128, Ser132, Trp137, Gln158, and the large leucine-rich hydrophobic pocket formed by the first and second LRRs. It was found that the potent Skp2 inhibitor (inhibitor #25 in FIG. 1B) was predicted to bind to pocket 1, but not pocket 2, indicating that the pocket 1 within the F-box motif is probably more critical to the Skp2-Skp1 interaction. This notion is in agreement with previous reports underscoring the importance of F-box motif in Skp2 SCF complex formation as well as Skp2 E3 ligase activity (Kim et al., 2003; Lin et al., 2009; von der Lehr et al., 2003).

Skp2 Small Molecule Inhibitors Suppress Skp2 SCF E3 Ubiquitin Ligase Activity In Vitro The canonical role of Skp2 SCF complex primarily triggers ubiquitination and degradation of its protein substrates (Chan et al., 2010b; Frescas and Pagano, 2008). Among all canonical Skp2 substrates, p27 is the most well characterized target whose deficiency can rescue the phenotypes observed in Skp2$^{-/-}$ mice, indicating that p27 is a physiological substrate for Skp2 (Nakayama et al., 2004). To determine the efficacy of compound #25 on targeting Skp2 activity in vivo, an in vivo p27 ubiquitination assay was performed to assess its ability to thwart Skp2 SCF E3 ligase activity in vivo. Since compound #25 displayed the highest efficacy in preventing skp2-skp1 complex formation (FIG. 1b), its effect on Skp2 SCF E3 ligase activity were determined FIG. 2A revealed that compound #25 inhibited Skp2-mediated p27 ubiquitination in a dose-dependent manner. Consistent with this p27 ubiquitination assay, it was also found that the treatment of compounds #25 induced endogenous p27 and p21 protein expression in prostate cancer cells (FIGS. 1F and 3E), recapitulating the phenotype upon genetic Skp2 ablation (Carrano et al., 1999; Chan et al., 2012). Similarly, compound #25 also induced expression of p21 (FIGS. 1F and 3E), another Skp2 substrate (Bornstein et al., 2003; Yu et al., 1998).

Akt was found to be a Skp2 substrate that triggers K63-linked Akt polyubiquitination, which does not lead to Akt degradation but instead promotes its membrane recruitment and activation (Chan et al., 2012). Consistent with the genetic evidence that Skp2 regulates Akt ubiquitination, compound #25 also inhibited Skp2-mediated Akt ubiquitination in prostate cancer cells (FIG. 1G). To determine whether the identified Skp2 inhibitor indeed blocks the E3 ligase activity of Skp2 SCF complex in vitro, the impact of compound #25 on Skp2-promoted Akt ubiquitination in vitro was examined. It was observed that while Skp2 promoted recombinant Akt ubiquitination in vitro, the presence of compound #25 attenuated Skp2-mediated Akt ubiquitination (FIG. 1H). Collectively, these results show that compound #25 is a Skp2 inhibitor.

Since Skp2 is required for EGF-mediated Akt phosphorylation and activation by triggering Akt ubiquitination, it was next determined whether Skp2 inhibitor attenuated the process. As expected, compound #25 profoundly inhibited EGF-mediated Akt phosphorylation and activation in various cancer cell lines (FIG. 2E and FIGS. 9A and 9B). However, administration of compound #25, similar to Skp2 deficiency did, displayed no noticeable impact on ERK activation (FIGS. 8C and 8D), underscoring the important role of Skp2 in selectively regulating EGF-mediated Akt signaling. It should be noted that Skp2 inhibitor not only abrogated Skp2 E3 ligase activity, but also downregulated Skp2 protein expression at higher dosage (20 µM), suggesting that disrupting Skp2-Skp1 interaction may result in Skp2 destabilization (FIGS. 1I and 3E and FIG. 8C). Moreover, the compound #25 primary caused downregulartion of Skp2 at the protein level, not mRNA level, and this reduction was partially rescued by proteasome inhibitor (FIGS. 8E and 8F). Collectively, these data indicate that the pharmacologic Skp2 inhibition stabilizes p27 and p21 expression and inhibits EGF-mediated Akt activation.

The Physical Binding of Skp2 Inhibitor to Skp2 Prevents Skp2-Skp1 Complex Formation The chemical structure of #25 disclosed in FIG. 2A is characterized by $^1$H, $^{13}$C NMR and LC-MS/MS analysis (FIG. 9). To understand how compound #25 interacts with Skp2 and prevents Skp2-Skp1 complex formation, molecular docking results were analyzed. The benzothiazole substructure of #25 is predicted to interact with residue Trp97, mainly via aromatic stacking and polar contacts (FIG. 2A). Interestingly, it is also close to a hydrophobic pocket consisting of Trp97, Leu105, Ile108, Phe109 and Trp127 (FIG. 2A). Potentially, interaction with this hydrophobic pocket can increase the binding. The other critical part of the inhibitor is the chromone moiety, which is extended through the pocket formed by residues Asp98 and Trp127 and has contacts with these residues via either hydrogen bonds or hydrophobic/aromatic interactions. Interestingly, the ethyl group on the phenol ring does not contribute significantly to the inhibitor binding to Skp2; however, it extends out into the region where Skp1 occupies when it binds to Skp2. Therefore this moiety is critical for preventing Skp1-Skp2 interactions, and removal of this ethyl group indeed abolished activity, in agreement with the structure-activity relationship studies. Additionally, the piperidine group of #25 is critical for the inhibitor binding as it interacts closely with Asp98 and Trp127.

It was observed that the pocket 2 inhibitors (such as inhibitor #5) have very different core scaffolds. They bind to pocket 2 mainly via interactions with Trp128, Ser132, Trp137, Gln158, and the large leucine-rich hydrophobic pocket formed by the first and second LRRs. The potent Skp2 inhibitor (inhibitor #25 in FIG. 1B) was predicted to bind to pocket 1, but not pocket 2, indicating that the pocket 1 within the F-box motif is probably more critical to the Skp2-Skp1 interaction. This notion is in agreement with previous reports underscoring the Importance of F-box motif in Skp2 SCF complex formation as well as Skp2 E3 ligase activity (Kim et al., 2003; von der Lehr et al., 2003). Based on the modeling predictions, residues Trp97, Asp98, Arg126 and Trp127 from Skp2 directly interact with compound #25 (FIG. 2A). While Pro101, Leu105, Ile108 and Phe109 residues are involved in Skp1 binding, but not significantly contributing to the binding of #25. Site-directed mutagenesis was next performed to mutate these residues to alanine (Ala) and determined which residues of Skp2 are critical for Skp2-Skp1 binding and Skp2 E3 ligase activity. Of these residues, only the Skp2 Trp97Ala, Asp98Ala, and Trp127Ala mutants still retained their binding capacity to Skp1, whereas the rest of other Skp2 mutants lost their interaction with Skp1 (FIG. 2B). The nature of the Arg126Ala mutant, which lost its ability to bind to Skp1, precluded us to further examine the inhibitory effect of compound #25 on its E3 ligase activity and binding to Skp1 For this reason, the inventors focused on Skp2 Trp97Ala, Asp98Ala, and Trp127Ala to determine the activity of compound #25 on their E3 ligase activity and interaction with Skp1. While compound #25 abrogated E3 ligase activity of WT Skp2 and Skp2 Trp127Ala mutant, as determined by in vivo p27 ubiquitination assay, it failed to inhibit E3 ligase activity of Skp2 Trp97Ala and Asp98Ala mutants, (FIG. 2C). Furthermore, in vitro Skp2-Skp1 binding assays revealed that although compound #25 prevented the interaction between WT Skp2 and Skp1, it was unable to inhibit the binding of Skp2 Trp97Ala and Asp98Ala mutants to Skp1 (FIG. 2D). These results suggest that Trp97 and Asp98 residues of Skp2 are critical sites for the binding of Skp2 to compound #25.

To corroborate this notion, the in vitro binding assay was performed to compare the binding affinity of compound #25 to WT Skp2 and Skp2 mutants (Trp97Ala and Asp98Ala) using LC-MS/MS analysis. Of note, since the nature of recombinant Skp2 protein was unstable in the absence of Skp1 (Li et al., 2005), the GST-Skp2 WT, GST-Skp2 Trp97Ala and GST-Skp2Asp98Ala mutants subjected to LC-MS/MS analysis were co-expressed, purified and preformed complex with Skp1 (FIG. 10A). In the preexisting Skp2-Skp1 complex, compound #25 readily bound to WT Skp2, but failed to interact with the Trp97Ala and Asp98Ala mutants (FIG. 2E and FIG. 10B). Accordingly, these results underscore that the binding of compound #25 to Skp2 at Trp97 and Asp98 is essential for blocking Skp2 E3 ligase activity.

Skp2 Inhibitor Specifically Suppresses E3 Ligase Activity of Skp2 SCF Complex, but not that of Other SCF Complexes.

To evaluate the specificity of the Skp2 inhibitor (compound #25), the inventors determined whether compound #25 may affect E3 ligase activity of other F-box proteins, such as FBW7 and β-TRCP. Although compound #25 displayed a profound effect on Skp2-mediated ubiquitination of p27 and Akt (FIGS. 1D, 1E, 1G, and 1F), it showed no appreciable effect on FBW7-mediated c-Jun and MCL-1 or β-TRCP-mediated β-catenin ubiquitination of Snail and IκBα in the presence of proteasome inhibitor (FIG. 3A). Consistent with this notion, compound #25 selectively stabilized Skp2 substrates including p27, p21, and Notch1 but not Fbw7 substrates such c-Jun and MCL-1 and β-TrCP substrates, such as Snail, IκBα, and β-catenin (FIGS. 3E and 11A). However, treatment of MLN4924, a potent inhibitor for Nedd8 activating enzyme (NAE) that suppresses activity of Cullin-RING based ubiquitin ligases (CRLs) and suppresses tumor development in xenograft models (Soucy et al., 2009), profoundly attenuated FBW7-mediated c-Jun ubiquitination (FIG. 11B). Likewise, substrates of SCF complexes, such as c-Jun, p27 and p21, were globally induced by MLN4924 (FIG. 3E). Of note, MLN4924 also induced expression of heat shock protein 27 (Hsp27), indicating that MLN4924 may elicit heat shock response through globally inhibiting intracellular proteolytic response in LNCaP prostate cancer cells (FIG. 3E). These results collectively suggest that this Skp2 inhibitor selectively targets E3 ligase activity of Skp2-SCF complex, but not other F box-containing SCF complexes.

Pharmacological Skp2 Inactivation Restricts Cancer Cell Proliferation and Survival Through Triggering p53-Independent Cellular Senescence and Inhibiting Aerobic Glycolysis Skp2 deficiency has a significant impact on cancer cell proliferation and survival by triggering cellular senescence and aerobic glycolysis (Chan et al., 2011; Chan et al., 2012; Lin et al., 2010). To test the therapeutic values of the Skp2 inhibitor (compound #25), the inventors determined whether compound #25 exhibits a similar impact on cancer cell proliferation and survival through triggering apoptosis and cellular senescence as Skp2 knockdown does. Indeed, Skp2 inhibitor displayed potent effects on cell viability of prostate cancer cell lines, including PC-3 and LNCaP cells, but only slightly affected cell viability of normal prostate epithelial PNT1A cells (FIG. 4A and FIG. 12A). The results indicate that compound #25 has a great selectivity on proliferation of prostate cancer cells over normal cells. Likewise, compound #25 favorably triggered cytotoxicity in tumorigenic lung cancer cells over non-tumorigenic lung fibroblast (FIG. 4B and FIG. 12A). Moreover, compound #25 also displayed a potent suppressive effect on viability of other human-tumor derived cell lines, including H3255 (lung), H3299 (lung), Hep3B (liver), and U2OS (osteocarcinoma), although different cancer cell types displayed variable sensitivity to the Skp2 inhibitor (FIG. 12A).

The underlying mechanism by which Skp2 inhibition regulates cancer cell proliferation and survival was evaluated. Consistent with the genetic Skp2 deficiency, the Skp2 inhibitor also triggered cellular senescence in p53-deficient prostate cancer cells, indicating that pharmacological Skp2 inactivation induced p53-independent senescence response (FIG. 4C). Additionally, Skp2 inactivation was found to suppress aerobic glycolysis in two prostate cancer cell lines similar to that of Akt inactivation, as determined by lactate production (FIGS. 4D and 4E). The inventors also demonstrated that the Skp2 inhibitor elicited cell apoptosis in prostate cancer cells (FIG. 4F and FIG. 13), consistent with the previous studies showing that a higher apoptosis rate was observed in Skp2-deficient cells and tissues (Kitagawa et al., 2008; Wang et al., 2010; Yokoi et al., 2003). These results, along with previous reports, demonstrate that genetic and pharmacological Skp2 inhibition attenuates cancer cell proliferation and survival possibly through regulating p53-independent cellular senescence, aerobic glycolysis or apoptosis.

To determine whether the biological effect of compound #25 is attributed to Skp2 inhibition, the effect of compound #25 on cell survival was explored in control- and Skp2-knockdown prostate cancer cells. While compound #25 displayed potent inhibitory effect on viability of control-knockdown cells in a dose-dependent manner, its inhibitory effect is compromised upon Skp2 silencing (FIG. 4G and FIG. 13C). The ectopic expression of Skp2 Trp97Ala or Skp2 Asp98Ala mutants was demonstrated, which is resistant to the binding of compound #25, attenuated the inhibitory effect of compound #25 on cell viability (FIG. 4H and FIG. 13D). Taken together, these results indicate that the action of compound #25 on cancer cell viability acts through its Skp2 inhibition and binding.

Structure-Activity Relationships (SARs) of Skp2 Inhibitor

To explore the SARs of this Skp2 inhibitor, a series of compound #25 derivatives were identified and evaluated their effects on in vitro Skp2-Skp1 binding (FIGS. 5A-5C). The data demonstrated that the benzothiazole at the $R_0$ position of the chromone core is necessary for binding, in agreement with the docking studies where it forms pi-stacking interactions with residue Trp97. The change of this group to a small thiazole ring caused the loss of activities (comparing #25 to #25-13 and #25-14 in FIGS. 5B and 5C), but modifications to a comparable moiety such as benzoimidazole retained the activities (#25-9). Apparently, the ethyl group on the $R_1$ position is critical as the activities are completely abolished when it is changed to hydrogen (e.g., #25 compared to #25-1 in FIGS. 5A and 5C). This is consistent with the docking observations where this group occupies the space where the Skp1 chain resides in the SCF complex. The SAR analysis indicated that any change to a big group (e.g., from hydrogen to methyl or ethyl ester) at the $R_2$ position is detrimental to the inhibitor binding (e.g. #25 compared to #25-10 and #25-12 in FIGS. 5B and 5C). This is also in agreement with the structural observations where the $R_2$ group has close contacts with Skp2 and therefore a small group is favorable to binding. Additionally, the chromone core of compound #25 can be altered to chromen-2-one, as compound #25-5 exhibited comparable ability to the lead compound (#25) in preventing Skp2-Skp1 interactions (FIGS. 5A and 5C). Modifications on the $R_3$ position, such as from the lead compound #25 to #25-7 or #25-8, destroyed the inhibitor activities. This is not surprising because in the docking models, that the piperidine ring was observed to be in a channel formed by residues Asp98 and Trp127. It is also in proximity to residue Arg126. Therefore, a no-substituted ring structure is preferred (FIGS. 5A and 5C). This also supports the site-directed mutagenesis data that Asp98 is the critical binding residue for Skp2 inhibitors (FIGS. 2 and 5A-5C). It is worth mentioning that the lack of the ethyl group on #25-5 did not affect the activity significantly (FIGS. 5A and 5C) because this compound has a slightly altered binding pose due to its different core scaffold. As a matter of fact, it seems that the piperidine moiety in #25-5 may partially serve the function of the ethyl group to repel Skp1 away.

Based on the SAR analysis, both compounds #25-5 and #25-9 disrupted in vivo Skp2-Skp1 binding as efficiently as lead compound #25 (FIGS. 5A-5C). To determine whether these two derivatives exhibited the same biological efficacy as compound #25, their roles in Skp2 E3 ligase and cancer cell survival were compared. As expected, the compounds profoundly inhibited Skp2-mediated p27 ubiquitination and cancer cell survival as compound #25 did, whereas other derivatives failed to do so (FIGS. 5D and 5E). These data along with mutagenesis results (FIG. 2 and FIG. 5) collectively illustrate that the stable interactions with the Trp97 and Asp98 residues is indispensible for the activities of Skp2 inhibitors in suppressing Skp2-Skp1 binding, Skp2 E3 ligase activity, and cancer cell survival (FIG. 2 and FIG. 5).

Skp2 Inactivation Inhibits Cancer Stem Cell Populations and Self-Renewal Capability Like stem cells (SCs), cancer stem cells (CSCs, also known as cancer initiating cells) express similar surface markers and possess asymmetric cell division and self-renewal capability. CSCs have recently emerged to play roles in cancer cell invasion and metastasis (Li and Tang, 2011; Velasco-Velazquez et al., 2011). However, how CSCs populations and self-renewal ability are regulated remains largely unclear. A recent report illustrated glycine decarboxylase drives CSC properties and tumorigenesis by promoting aerobic glycolysis (Zhang et al., 2012). In addition to glycolysis, cellular senescence through telomere shortening has been linked to restrain CSC populations (Marian et al., 2010a; Marian et al., 2010b). In light of these observations, it was reasoned that targeting cellular senescence and aerobic glycolysis pathways may reduce CSC self-renewal and favor chemotherapy sensitivity.

As Skp2 regulates p53-independent cellular senescence and Akt-mediated aerobic glycolysis, the inventors evaluated whether Skp2 inactivation has any effect on CSC populations and their self-renewal capability. Both Skp2 knockdown and pharmacologic Skp2 inactivation in prostate cancer cells reduced CSCs populations, similar to what the inhibition of the PI3K-Akt pathway did (FIGS. 6A-6E and FIG. 13C). While compound #25 was found to reduce the population of prostate CSCs in a dose dependent manner, it failed to do so upon Skp2 silencing. This data underscores the fact that Skp2-regulated CSC pool size strictly depends on Skp2 (FIG. 6C). The prostate sphere formation assay also revealed that Skp2 inhibition by genetic and pharmacologic approaches markedly suppressed self-renewal ability of prostate CSCs, so did Akt inactivation (FIGS. 6F and 6G). These results indicate that Skp2 plays a significant role in regulating CSC population and self-renewal capability.

The existence of a subset of stem cell-like population in tumor tissues, so called CSCs, is the major cause for cancer cell resistance to chemotherapy (Koch et al., 2010). As genetic and pharmacological Skp2 inactivation effectively restricts CSCs properties in prostate cancer cells (FIG. 6), it was reasoned that the Skp2 inhibitor may sensitize cancer cell response to chemotherapeutic agents, such as doxorubicin (Dox) and cyclophosphamide (CPA) (FIGS. 7A and 7B). Skp2 inhibition increased the efficacy of Dox and CPA on prostate cancer cells, indicating that Skp2 inhibitor may overcome chemo-resistance in prostate cancer cells via eradicating CSC populations.

Pharmacological Skp2 Inactivation Exhibits Strong Anti-Tumor Activities In Vivo.

Escape of cellular senescence and promotion of aerobic glycolysis are two critical hallmarks for cancer progression and cancer drug resistance, and both are critically regulated by Akt activation. Targeting these two events may therefore be a particularly useful approach for cancer treatment. The inventors have identified Skp2 as a regulator in Akt-mediated glycolysis and p27-mediated cellular senescence using genetic and pharmacologic approaches, in turn regulating cancer progression; therefore targeting Skp2 may be an effective strategy for treatment of human cancers. To further support this notion, the efficacy of this Skp2 inhibitor on suppression of preexisting tumors in vivo was examined FIGS. 7C and 7D demonstrated that a Skp2 inhibitor (compound #25) displayed a potent effect on inhibiting the prostate tumor growth and lung tumor growth in vivo. Importantly, it was found that treatment of Skp2 inhibitor induced expression of p27 and p21, apoptosis, and suppressed Akt activation and Glut1 expression (glucose transporter 1), critical regulators for glycolysis, in prostate tumor tissues (FIGS. 7D-7F and FIGS. 14A and 14B). The pharmacokinetic analysis further revealed that the concentration of compound #25 reached maximum levels in blood 1 h after IP administration ($C_{max}$ was 1428±1185 ng/ml), maintained up to 70% of the compound for 6 h, but quickly declined afterward with a terminal concentration of 126±48 ng/ml 24 h after administration (FIG. 14C). Of note, compound #25 indeed reached tumors within 1 h with a concentration of 4787±1967 ng/g and slowly declined in tumor tissues and about 1164±494 ng/ml of compound #25 remained in tumor tissues 24 h after initial administration (FIG. 14C). These results provide pharmacologic evidence that Skp2 targeting or inhibition may be used for the treatment of human cancers.

Identification of Specific Skp2 Inhibitors

Ubiquitination, like phosphorylation, plays important roles in several biological processes by regulating protein turnover, trafficking and signaling activation (Ikeda et al., 2010). Within the ubiquitin signaling network, E3 ubiquitin ligases determining substrate specificity are thought to be compelling druggable targets. Of note, Skp2 frequently upregulated in human cancer is shown to play a critical role in cancer development by targeting p27 protein degradation or activating Akt signaling. Therefore, it is of particular interest to develop cancer therapeutics by inhibiting Skp2 activity. Recently, two small molecules targeting the p27 pathways were identified: a small molecule cpdA targeting p27 ubiquitination (Chen et al., 2008), and MLN4924, a small molecule inhibitor targeting NAE (Soucy et al., 2009). Although cpdA could cause cell cycle arrest, apoptosis, and autophagy in leukemia cells, its in vivo efficacy on tumor growth was not examined. Moreover, it is still unclear how cpdA regulates p27 ubiquitination, and whether it has any direct effect on Skp2 activity remains to be determined. The second study demonstrated that MLN4924 reduced Cul-1 neddylation, accompanied by inducing p27 accumulation, cell cycle arrest, apoptosis, and senescence, in turn suppressing tumor growth in vivo using xenograft tumor models (Lin et al., 2010; Soucy et al., 2009). It was found, however, that MLN4924 has a general effect on targeting F-box proteins including Skp2 and FBW7 (FIGS. 11B and 3E), consistent with the notion that Cul-1-neddylation is required for the integrity and activity of the SCF complex (Liu et al., 2002; Zheng et al., 2002a). As shown in the experiments described herein, compound #25 (SZL-P1-41) was observed to be a specific Skp2 inhibitor by directly binding to Skp2 pocket 1 around the F-box motif and disrupting Skp2-Skp1 interactions, thus abrogating Skp2 E3 ligase activity toward ubiquitination of p27 and Akt (FIGS. 1D and 1G). Remarkably, the Skp2 inhibitor does not affect activity of other F-Box proteins such as FBW7 and β-TrCP (FIG. 3A). The integrated platform of in silico modeling and experimental evaluation was observed to be a cost-effective and time-efficient approach for systematically identifying small molecule inhibitors of Skp2 as well as for other SCF complex and/or F-box proteins.

Targeting p53-Independent Cellular Senescence and Aerobic Glycolysis for Cancer Treatment Induction of cellular senescence resulting from replicative stress or oncogenic insults elicits p53-dependent or -independent pathways that prevent cancer progression. p53-stabilizing small molecules has demonstrated senescence-inducing effects on tumor suppression (Brown et al., 2009), but applying a p53-dependent cellular senescence strategy may not be applicable for a wide range of tumor types since p53 is a prevalently mutated or inactivated gene in human cancer. As such, numerous discoveries have focused on the role of p53-independent pathways in cancer treatment (Chan et al., 2011; Nardella et al., 2011). Genetic ablation of Skp2 in combination of Pten or Arf loss evoked cellular senescence through neither the p19Arf/p53 pathway nor DNA damage response (Lin et al., 2010). In agreement with this notion, indirect targeting of the Skp2-SCF complex via a small molecule (MLN4924) has been shown to trigger p53-independent senescence and repress prostate tumors with p53 inactivation (Lin et al., 2010; Soucy et al., 2009). In the experiments described herein, it was shown for the first time that treatment with a specific Skp2 inhibitor indeed triggers cellular senescence in p53-deficient prostate cancer cells (FIG. 4C) and inhibits prostate tumor growth in vivo (FIGS. 7C and 6F), supporting the notion that targeting oncogenic Skp2 may be a very effective approach for treating advanced human cancers with p53 inactivation.

Aerobic glycolysis is an emerging cancer hallmark, which fuels elevated energy need for cell proliferation and fosters cancer development (Hanahan and Weinberg, 2011). The supporting evidence came from several recent reports showing that numerous metabolic enzymes, such as the pyruvate kinase M2 (PKM2), the isocitrate dehydrogenase 1 and 2 (IDH1/2) and glycine decarboxylase (GLDC), have been linked to cancer development (Christofk et al., 2008; Dang et al., 2009; Parsons et al., 2008; Zhang et al., 2012). Collectively, these reports indicate that targeting glycolytic regulators may represent a useful approach for cancer therapy. As shown herein, pharmacological inhibition of Skp2 impedes cancer glycolysis and cancer development provide an important proof for this concept (FIGS. 4D, 4E, 6F and 7C-7D), thereby supporting the use of small molecule inhibitors targeting glycolysis as cancer therapeutic agents.

Skp2 Regulates CSC Population and Functions

CSCs recently have emerged to be crucial to cancer initiation, progression, and relapse after chemotherapy (Harmes and DiRenzo, 2009; Rajan and Srinivasan, 2008). Thus, orchestrating or targeting the populations and functions of CSCs may help thwart cancer progression and improve the efficacy of current chemotherapy agents. The data presented herein using the genetic (Skp2 knockdown) and pharmacologic (Skp2 selective inhibitors) approaches demonstrated that Skp2 inactivation reduce CSC populations and their ability to form prostate spheres (FIG. 6), providing evidence that Skp2 can regulate the maintenance of CSCs. Given that Skp2 targeting attenuates aerobic glycolysis and induces cellular senescence in cancer cells, these experiments indicates that targeting glycolysis and inducing cellular senescence pathways may represent attractive strategies for CSC treatment and/or elimination. In support of this notion, a recent report shows that a metabolic player, glycine decarboxylase, critically involved in glycolysis, is highly overexpressed in non-small cell lung cancer whose overexpression induces CSC growth and tumorigenesis, whereas its knockdown reduces lung cancer development (Zhang et al., 2012).

Pharmacological Skp2 Inhibition in Treatment of Cancer and Other Diseases

Genetic approaches have demonstrated that Skp2 deficiency inhibits cancer development in multiple mouse models by inducing p53-independent cellular senescence and blocking Akt-mediated aerobic glycolysis (Chan et al., 2012; Lin et al., 2010). In this study, specific Skp2 inhibitors were identified by using in silico high-throughput screening of a large chemical database. These inhibitors were validated for their effects on blocking Skp2-Skp1 interaction, inhibiting Skp2 SCF E3 ligase activity toward ubiquitination of p27 and Aid, and repressing in vivo tumor growth. A function of Skp2 in governing CSC properties (FIG. 7G) was also observed. These experiments provide proof of principle that pharmacologic Skp2 inactivation can profoundly restrict cancer developments in various cancer models and confer sensitivity to chemotherapy, supporting the idea that Skp2 is a promising drug target for human cancers.

Not only does Skp2 regulate glucose metabolism and therefore endows cancer development (Chan et al., 2012), but also it plays an essential role in other metabolic disorder such as obesity, evidenced by a previous report demonstrating that Skp2 ablation protect mice from developing obesity through reducing adipocyte proliferation (Sakai et al., 2007). Having shown the promise of the Skp2 inhibitor in suppressing glycolysis in vitro and in vivo (FIGS. 4D, 4E and 6F), it is anticipated that Skp2 inhibitors may be used as an anti-obesity therapy. As such, the present data opens up a new avenue in multiple therapeutic areas that can translate basic findings into the clinical settings, thereby offering a significant opportunity and potential impact on the treatment of cancer as well as other metabolic disorders.

Selection of Additional Compounds for Structure-Activity Relationship (SAR) Studies and Measurement of Corresponding Activity Additional compounds were tested and their activities were evaluated. A series of in silico experiments were also carried out on compound #25 and on the Skp2 target protein to further elucidate the binding mechanism of the compound and determine how its effects can disrupt the target protein complex. The molecular dynamics of Skp2 structure and their roles in ubiquitination and inhibitor binding are also being evaluated. In particular, the inventors have explored the structure of Skp2 N-terminal residues. Compounds were obtained from chemical libraries, specifically from Chembridge, TimTec and Maybridge vendors.

Based on the results of the first round of testing of similar compounds that were tested and are described herein, additional compounds were identified to improve the activity and help determine SARs that may be responsible for the activity. Synthesis was focused on the key functional moieties of the compound #25, and libraries of derivatives were attempted to be synthesized from late stage intermediates exploring the SAR of each of these regions of the molecule. Based on the modeling and experimental testing results, optimal substituents were combined with rational molecular design. The synthetic schemes below provide an example of detailed synthesis to build focused libraries, beginning with the assembly of the appropriately substituted 2-methyl benxothiazoles 8 and 9 as outlined in Scheme 1 of FIG. 7 using the methodology of Kozikowski et al; Huang et al., 2009; Kashiyama et al., 1999; and Mathis et al., 2003. Treatment of 3-methoxy-aniline 1 or 2-methyl aniline 2 with acetic anhydride/pyridine afforded the corresponding benzanilides 3 and 4. Subsequent treatment of the amides with Lawesson's reagent in refluxing chlorobenzene yielded the corresponding thiobenzanilides 5 and 6. Cyclization to the corresponding substituted 2-methylbenzothiazoles 8 and 9 was accomplished by treatment with potassium ferricyanide in aqueous NaOH. Preparation of 2-methylbenzothiazole 7 is unnecessary due to its commercial availability. Construction of the appropriately substituted amino isoflavones 32-35 is outlined in Scheme 2. Esterification (Hadj-esfandiari et al., 2007) of salicylic acid derivatives 10 and 11 with sulfuric acid/ethanol will provide the prerequisite ethyl salicylates 12 and 13. At this point the hydroxyl group was protected as the tert-butyldimethylsilyl ether 14 and 15 using standard methodology (Lee et al., 2004). With the fully protected ethyl salicylates 14 and 15 in hand, we performed condensation of the appropriately substituted 2-methylbenzothiazoles 7-9 (Scheme 1), which were lithiated with n-BuLi at $-78°$ C., with the previously prepared ethyl salicylates 14 and 15, using the methodology of Costa et al., 1991 to afford the corresponding condensation products 16-19. De-tert-butylsilylation was achieved by brief treatment with tetrabutylammonium fluoride (TBAF) to afford the corresponding substituted 2-hydroxydeoxybenzoin compounds 20-23. Cyclization of 20-23 can be easily accomplished using a modified Venkataraman (Gao et al., 2003; Gulati et al., 1943; Nussbaumer et al., 2005) reaction. Treatment with triethyl orthoformate/morpholine/isopropanol at $80°$ C. affords the isoflavones 24-27. Global demethylation was accomplished using the methodology of Wang et al.; Ding et al., 2005). Thus treatment of 24-27 with boron tribromide at $-78°$ C. and slowly raising the reaction to room temperature afforded the substituted isoflavones 28-31. The benzothiazole moiety of the isoflavones is stable to conditions of global demethylation as previously observed by Kozikowski et al.; and Huang et al., 2009. Final aminomethylation of the substituted isoflavones 28-31 to afford the corresponding N-substituted aminomethyl isoflavones 32-35 was accomplished by using the methodologies of Frasinyuk et al., 1998; or Hu et al.; Liu et al., 2007.

Scheme 1

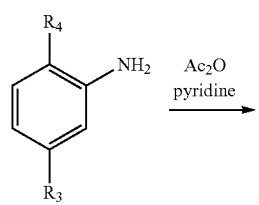

1 $R_3 = CH_3O$, $R_4 = H$
2 $R_3 = H$, $R_4 = CH_3$

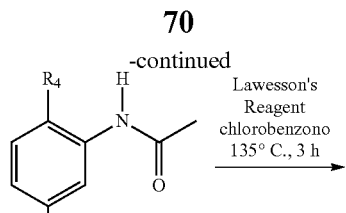

3 $R_3 = CH_3O$, $R_4 = H$
4 $R_3 = H$, $R_4 = CH_3$

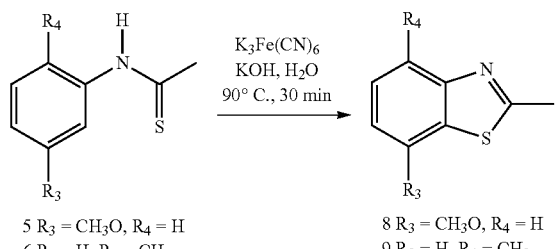

5 $R_3 = CH_3O$, $R_4 = H$
6 $R_3 = H$, $R_4 = CH_3$

8 $R_3 = CH_3O$, $R_4 = H$
9 $R_3 = H$, $R_4 = CH_3$

Scheme 2

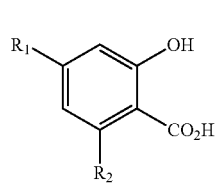

10 $R_1 = CH_3O$, $R_2 = H$
11 $R_1 = CH_3O$, $R_2 = CH_3O$

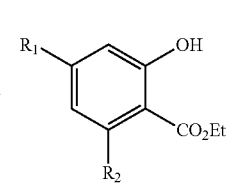

12 $R_1 = CH_3O$, $R_2 = H$
13 $R_1 = CH_3O$, $R_2 = CH_3O$

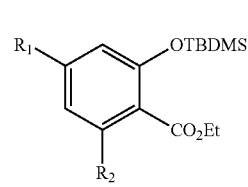

14 $R_1 = CH_3O$, $R_2 = H$
15 $R_1 = CH_3O$, $R_2 = CH_3O$

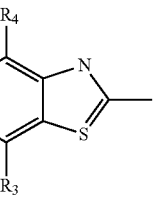

7 $R_3 = R_4 = H$
8 $R_3 = CH_3O$, $R_4 = H$
9 $R_3 = H$, $R_4 = CH_3$

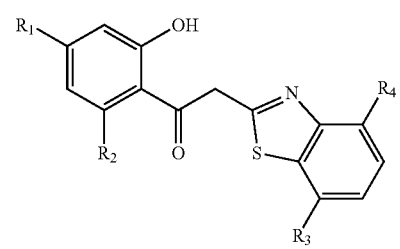

16 $R_1 = CH_3O$, $R_2 = H$, $R_3 = R_4 = H$
17 $R_1 = CH_3O$, $R_2 = H$, $R_3 = OCH_3$, $R_4 = H$
18 $R_1 = CH_3O$, $R_2 = H$, $R_3 = H$, $R_4 = CH_3$
19 $R_1 = CH_3O$, $R_2 = CH_3O$, $R_3 = R_4 = H$

TBAF, THF
rt, 1 hr

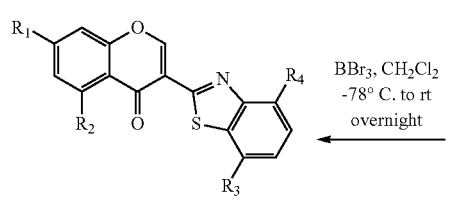 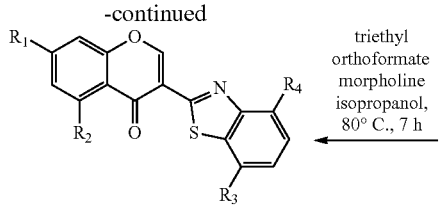 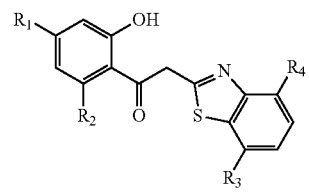

28 R$_1$ = OH, R$_2$ = H, R$_3$ = R$_4$ = H
29 R$_1$ = OH, R$_2$ = H, R$_3$ = OH, R$_4$ =H
30 R$_1$ = OH, R$_2$ = H, R$_3$ = H, R$_4$ = CH$_3$
31 R$_1$ = OH, R$_2$ = OH, R$_3$ = R$_4$ = H

24 R$_1$ = CH$_3$O, R$_2$ = H, R$_3$ = R$_4$ = H
25 R$_1$ = CH$_3$O, R$_2$ = H, R$_3$ = OCH$_3$, R$_4$ = H
26 R$_1$ = CH$_3$O, R$_2$ = H, R$_3$ = H, R$_4$ = CH$_3$
27 R$_1$ = CH$_3$O, R$_2$ = CH$_3$O, R$_3$ = R$_4$ = H

20 R$_1$ = CH$_3$O, R$_2$ = H, R$_3$ = R$_4$ = H
21 R$_1$ = CH$_3$O, R$_2$ = H, R$_3$ = OCH$_3$, R$_4$ = H
22 R$_1$ = CH$_3$O, R$_2$ = H, R$_3$ = H, R$_4$ = CH$_3$
23 R$_1$ = CH$_3$O, R$_2$ = CH$_3$O, R$_3$ = R$_4$ = H

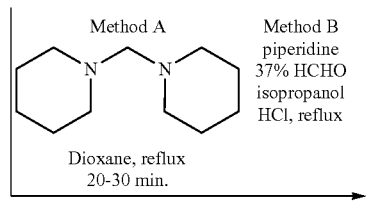 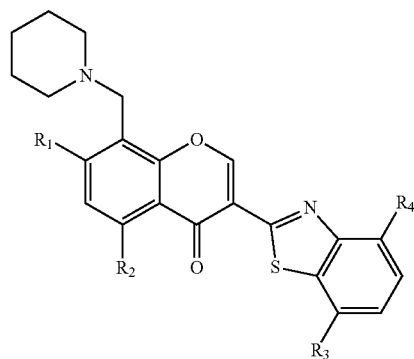

Method A — Dioxane, reflux 20-30 min.
Method B — piperidine 37% HCHO isopropanol HCl, reflux 32 R$_1$ = OH, R$_2$ = H, R$_3$ = R$_4$ = H
33 R$_1$ = OH, R$_2$ = H, R$_3$ = OH, R$_4$ =H
34 R$_1$ = OH, R$_2$ = H, R$_3$ = H, R$_4$ = CH$_3$
35 R$_1$ = OH, R$_2$ = OH, R$_3$ = R$_4$ = H Detailed Synthetic Schemes to Build Focused Libraries of Lead #25.

Scheme 1 (upper): 2-methyl benxothiazoles. Scheme 2 (bottom): synthesis of SZL-P1-41 derivatives.

Below are the original lead compound and 11 similar compounds that were tested for their ability to block the Skp1/Skp2 binding interaction in an in vitro assay. The quantification was made on western blot/images, and the percentages represent the amount of intact Skp1/Skp2 remaining after treatment. In vitro binding assays were performed. For in vitro GST-Skp1 and Skp2 interaction, GST-Skp1 proteins purified from the bacterial lysates of BL21 competent cells transformed with pGEX-4X1-Skp1 using the Glutathione-Agarose beads were performed according to the manufacturer's standard procedures. The GST-Skp1 proteins bound to glutathione Sepharose beads (Amersham Biosciences) were then incubated with the in vitro translated [35$^S$]-Skp2 for 2 hours at 4° C. in the interaction buffer with or without lead compound and 11 similar compounds (20 mM HEPES, PH 7.9, 150 mM KCl. 5 mM EDTA, 0.5 mM DTT, 0.1% (v/v) Nonidet p-40, 0.1% (w/v) BSA, 1 mM PMSF, and 10% Glycerol), washed by the NETN buffer (20 mM Tris, pH 8.0, 100 mM NaCl, 6 mM MgCl2, 1 mM EDTA, 0.5% Nonidet P-40, 1 mM DTT, 8% glycerol, 1 mM PMSF) 4 times, and subjected to 8% SDS-PAGE, followed by autoradiography. The data presented in Table 1 below was obtained using the Skp1/Skp2 binding affinity assay. The quantification percentage results listed below are based on the western blot results.

TABLE 1

| Structure | ID# | Mol Wt | logP | Normalized w/ vehicle treatment |
|---|---|---|---|---|
| 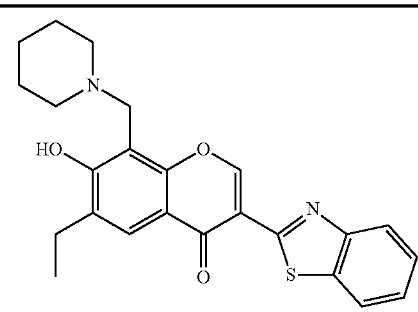 | #25 | 420.527 | 4.58 | 10% |

TABLE 1-continued
| Structure | ID# | Mol Wt | logP | Normalized w/ vehicle treatment |
|---|---|---|---|---|
| 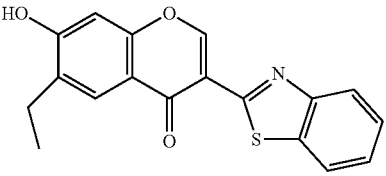 [SMILES: CCc1cc2c(=O)c(-c3nc4ccccc4s3)coc2cc1O] | 378 | 323.366 | 3.598 | 100% (no effect) |
| 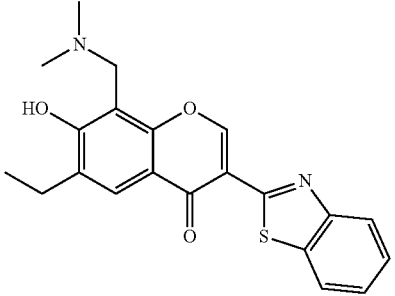 [SMILES: CCc1cc2c(=O)c(-c3nc4ccccc4s3)coc2c(CN(C)C)c1O] | 653 | 380.462 | 3.606 | 8% |
| 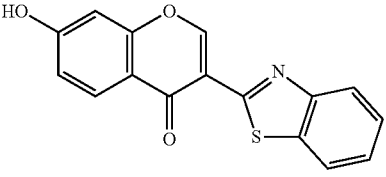 [SMILES: O=c1c(-c2nc3ccccc3s2)coc2cc(O)ccc12] | 684 | 295.312 | 2.79 | 75% |
| 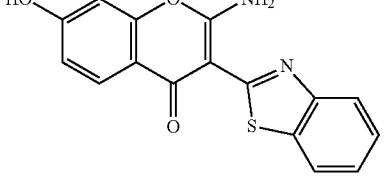 | 649 | 310.327 | 2.881 | 8% |
| 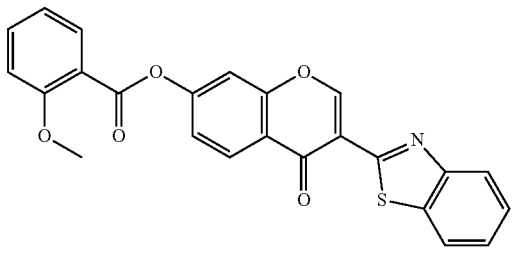 [SMILES: COc1ccccc1C(=O)Oc1ccc2c(=O)c(-c3nc4ccccc4s3)coc2c1] | 837 | 429.446 | 4.647 | 8% |
| 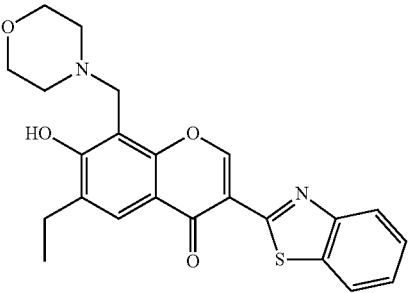 [SMILES: CCc1cc2c(=O)c(-c3nc4ccccc4s3)coc2c(CN2CCOCC2)c1O] | 354 | 422.499 | 3.172 | 10% |

TABLE 1-continued

| Structure | ID# | Mol Wt | logP | Normalized w/ vehicle treatment |
|---|---|---|---|---|
| 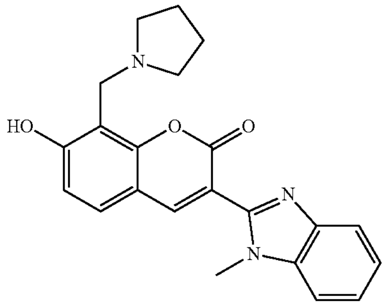 [SMILES: Cn1c(-c2cc3ccc(O)c(CN4CCCC4)c3oc2=O)nc2ccccc21] | 343 | 375.428 | 3.956 | 35% |
| 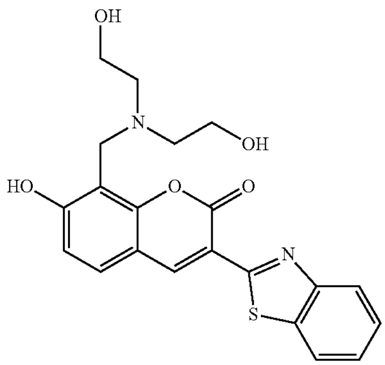 [SMILES: O=c1oc2c(CN(CCO)CCO)c(O)ccc2cc1-c1nc2ccccc2s1] | 719 | 412.46 | 2.524 | 80% |
| 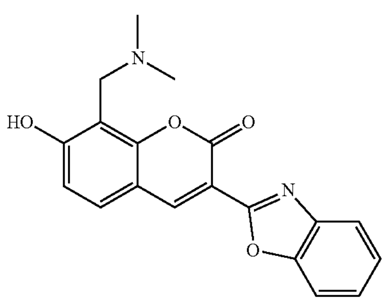 [SMILES: CN(C)Cc1c(O)ccc2cc(-c3nc4ccccc4o3)c(=O)oc12] | 820 | 336.347 | 3.097 | 10% |
| 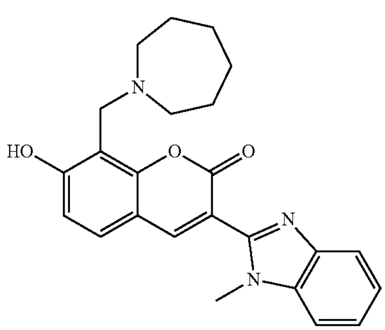 [SMILES: Cn1c(-c2cc3ccc(O)c(CN4CCCCCC4)c3oc2=O)nc2ccccc21] | 580 | 403.482 | 4.84 | 8% |

TABLE 1-continued

| Structure | ID# | Mol Wt | logP | Normalized w/ vehicle treatment |
|---|---|---|---|---|
| (structure) | 435 | 389.455 | 4.398 | 40% |

In Silico Modeling of Skp2 Structural Flexibility and Inhibitor Binding Via Homology Modeling and Molecular Dynamics.

To further guide optimization of compounds with higher binding affinity, a series of experiments were carried out to uncover how the compound #25 may be binding to Skp2 and disrupting the Skp1 interaction. As compound #25 appears to be binding to Skp2 very close to the end of the 2AST crystal structure (interacting with Trp97 and there are 95 residues in the N-terminal tail that were not crystalized in the 2AST structure, the inventors sought to determine how the N-terminal tail might contribute to the binding of compound #25. MODELLER was used to generate a 15 residue homology model of the tail region, and Fbw7 (PDBID: 2OVP) was used as the structural template. Multiple models were generated and loop were refined using MODELLER. The most appropriate model was selected which was used to perform molecular dynamics simulations using AMBER. The criterion for the model selection was primarily based on the position of the N-terminal tail relative to the Skp1 and Cullin 1 (another protein component of the SCF complex). The inventors sampled models that were also diverse in their tail conformations to allow for sampling of more than one possible transition state of this region (e.g., see FIG. 15). The inventors also considered if the model retained the original binding pocket that is seen in the 2AST crystal structure.

These homology models were used as a platform to perform molecular dynamics (MD) simulations and sample the conformational space of Skp2 with the tail attached. Four models generated from homology modeling of the Skp2 Fbox domain with the tail region were submitted for MD simulations using AMBER for 30 ns runs with explicit waters. Using RMSD analysis of the backbone atoms of the structures, the four models were analyzed after they were found to reach a stable conformation and the average structures were calculated. After the 30 ns runs, two of the four tail regions reached a consensus patterns, and one of these models' average structure in the stable time point was used for in silico docking of compound #25, as previously described. It is anticipated that the tail residues may participate in or affect inhibitor binding.

In addition to this study of the tail region of Skp2, the inventors have also conducted MD simulations of the mutant forms of Skp2 that were reported to lose the binding of compound #25, Skp1, or both. The observations are consistent to the mutagenesis studies performed.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,399,363
U.S. Pat. No. 5,466,468
U.S. Pat. No. 5,543,158
U.S. Pat. No. 5,580,579
U.S. Pat. No. 5,629,001
U.S. Pat. No. 5,641,515
U.S. Pat. No. 5,725,871
U.S. Pat. No. 5,756,353
U.S. Pat. No. 5,780,045
U.S. Pat. No. 5,792,451
U.S. Pat. No. 5,804,212
U.S. Pat. No. 6,537,514
U.S. Pat. No. 6,613,308
Ahad et al., *Bioorg. Med. Chem.*, 19:2046-2054, 2011.
Bornstein et al., *J. Biol. Chem.*, 278:25752-25757, 2003.
Brenke et al., *Bioinformatics*, 25(5):621-627, 2009.
Brown et al., *Nat. Rev. Cancer*, 9:862-873, 2009.
Buzzai et al., *Oncogene*, 24:4165-4173, 2005.
Carrano et al., *Nat. Cell Biol.*, 1:193-199, 1999.
Chan et al., *Cell*, 149(5):1098-1111, 2012.
Chan et al., *J. Mol. Med.* (Berl), 89:857-867, 2011.
Chan et al., *Nat. Cell Biol.*, 12:457-467, 2010a.
Chan et al., *Scientific World J.*, 10:1001-1015, 2010b.
Chen et al., *Blood*, 111:4690-4699, 2008.
Christofk et al., *Nature*, 452:230-233, 2008.
Costa, M. W., Brembilla, A., Roizard, D., and Lochon, P. (1991). Action of (2-benzothiazolyl) methyllithium with organic polar functions. Journal of Heterocyclic Chemistry 28, 1541-1544.

Dang et al., *Nature*, 462:739-744, 2009.

Ding, K., and Wang, S. (2005). Efficient synthesis of isoflavone analogues via a Suzuki coupling reaction. Tetrahedron Letters 46, 3707-3709.

Du-Cuny et al., *Bioorg. Med. Chem.*, 17:6983-6992, 2009.

Elstrom et al., *Cancer Res.*, 64:3892-3899, 2004.

Frasinyuk, M. S., Turov, A. V., and Khilya, V. P. (1998). Chemistry of the hetero analogs of isoflavones. 22. Mannich reaction in the benzimidazole and benzothiazole analogs of isoflavones. Chemistry of Heterocyclic Compounds 34, 923-928.

Frescas and Pagano, *Nat. Rev. Cancer*, 8:438-449, 2008.

Gao, G. Y., Li, D. J., and Keung, W. M. (2003). Synthesis of daidzin analogues as potential agents for alcohol abuse. Bioorg Med Chem. 11, 4069-4081.

Gohlke et al., *Perspectives Drug Discov. Design*, 20:115-144, 2000.

Gulati, K. C., Seth, S. R., and Venkataraman, K. (1943). Phloroacetophenone. Organic Synthesis 2, 522.

Hadj-esfandiari, N., Navidpour, L., Shadnia, H., Amini, M., Samadi, N., Faramarzi, M. A., and Shafiee, A. (2007). Synthesis, antibacterial activity, and quantitative structure-activity relationships of new (Z)-2-(nitroimidazolyl-methylene)-3(2H)-benzofuranone derivatives. Bioorg Med Chem Lett 17, 6354-6363.

Hanahan and Weinberg, *Cell*, 144:646-674, 2011.

*Handbook of Pharmaceutical Salts: Properties*, and Use, Stahl & Wermuth (Eds.), Verlag Helvetica Chimica Acta, 2002.

Hao et al., *Mol. Cell*, 20:9-19, 2005.

Harmes and DiRenzo, *J. Mammary Gland Biol. Neoplasia*, 14:19-27, 2009.

Hershko, *Cancer*, 112:1415-1424, 2008.

Huang, Q., Mao, J., Wan, B., Wang, Y., Brun, R., Franzblau, S. G., and Kozikowski, A. P. (2009). Searching for new cures for tuberculosis: design, synthesis, and biological evaluation of 2-methylbenzothiazoles. J Med Chem 52, 6757-6767.

Hwang et al., *Crit. Rev. Ther. Drug Carrier Syst.*, 15(3): 243-284, 1998.

Ikeda et al., *Cell*, 143:677-681, 2010.

Kashiyama, E., Hutchinson, I., Chua, M. S., Stinson, S. F., Phillips, L. R., Kaur, G., Sausville, E. A., Bradshaw, T. D., Westwell, A. D., and Stevens, M. F. (1999). Antitumor benzothiazoles. 8. Synthesis, metabolic formation, and biological properties of the C- and N-oxidation products of antitumor 2-(4-aminophenyl)benzothiazoles. J Med Chem 42, 4172-4184.

Kim et al., *Mol. Cell*, 11:1177-1188, 2003.

Kitagawa et al., *Mol. Cell*, 29:217-231, 2008.

Koch et al., *Semin. Cancer Biol.*, 20:116-124, 2010.

Lee, H. J., Seo, J. W., Lee, B. H., Chung, K. H., and Chi, D. Y. (2004). Syntheses and radical scavenging activities of resveratrol derivatives. Bioorg Med Chem Lett 14, 463-466.

Li et al., 2005

Li and Tang, *J. Surg. Oncol.*, 103:558-562, 2011.

Lin et al., *Nat. Cell Biol.*, 11:420-432, 2009.

Lin et al., *Nature*, 464:374-379, 2010.

Liu et al., *Mol. Cell*, 10:1511-1518, 2002.

Liu, T., Xu, Z., He, Q., Chen, Y., Yang, B., and Hu, Y. (2007). Nitrogen-containing flavonoids as CDK1/Cyclin B inhibitors: design, synthesis, and biological evaluation. Bioorg Med Chem Lett. 17, 278-281.

Mahadevan et al., *Mol. Cancer Ther.*, 7:2621-2632, 2008.

Mandinova and Lee, *Sci. Transl. Med.*, 3:64rv61, 2011.

March's Advanced Organic Chemistry: Reactions, Mechanisms, and Structure, 2007.

Marian et al., *Clin. Cancer Res.*, 16:154-163, 2010a.

Marian et al., *Int. J. Cancer*, 127:321-331, 2010b.

Mathiowitz et al., *Nature*, 386(6623):410-414, 1997.

Mathis, C. A., Wang, Y., Holt, D. P., Huang, G. F., Debnath, M. L., and Klunk, W. E. (2003). Synthesis and evaluation of 11C-labeled 6-substituted 2-arylbenzothiazoles as amyloid imaging agents. J Med Chem. 46, 2740-2754.

Nakayama et al., *Dev. Cell*, 6:661-672, 2004.

Nakayama et al., *EMBO J.*, 19:2069-2081, 2000.

Nardella et al., *Nat. Rev. Cancer*, 11:503-511, 2011.

Nussbaumer, P., Lehr, P., and Billich, A. (2002). 2-Substituted 4-(thio)chromenone 6-O-sulfamates: potent inhibitors of human steroid sulfatase. J Med Chem. 45, 4310-4320.

Parsons et al., *Science*, 321:1807-1812, 2008.

Rajan and Srinivasan, *Stem Cell Rev.*, 4:211-216, 2008.

Remington's Pharmaceutical Sciences" 15th Ed., 1035-1038 and 1570-1580, 1990.

Remington's Science and Practice of Pharmacy, 21st Ed., Mack Printing Company, 2005.

Remington's Pharmaceutical Sciences, 18th Ed. Mack Printing Company, 1289-1329, 1990.

Robey and Hay, *Semin. Cancer Biol.*, 19:25-31, 2009.

Sakai et al., *J. Biol. Chem.*, 282:2038-2046, 2007.

Schulman et al., *Nature*, 408:381-386, 2000.

The Science and Practice of Pharmacy, 21st Ed. Lippincott Williams and Wilkins, 2005

Soucy et al., *Nature*, 458:732-736, 2009.

Takenaga et al., *J. Control Release*, 52(1-2):81-87, 1998.

Tran and Zhang, *J. Chem. Inf. Model*, 51:2352-2360, 2011.

Tuncbag et al., *Nucleic Acids Res.*, 38 (Web Server issue): W402-6, 2010.

Vander Heiden et al., *Science*, 324:1029-1033, 2009.

Vazquez et al., *Nat. Rev. Drug Discov.*, 7:979-987, 2008.

Velasco-Velazquez et al., *Am. J. Pathol.*, 179:2-11, 2011.

von der Lehr et al., *Mol. Cell*, 11:1189-1200, 2003.

Wang et al., *Nat. Genet.*, 42:83-88, 2010.

Warburg, *Science*, 123:309-314, 1956.

Wu et al., *J. Pharmacol. Exp. Ther.*, 336:403-413, 2011a.

Wu et al., *Mol. Pharm.*, 8:2379-2389, 2011b.

Yadav et al., *J. Biol. Chem.*, 287:245-256, 2012.

Yang et al., *Science*, 325:1134-1138, 2009.

Yokoi et al., *Cancer Sci.*, 94:344-349, 2003.

Yu et al., *Proc. Natl. Acad. Sci. USA*, 95:11324-11329, 1998.

Zhang et al., *Cell*, 148:259-272, 2012.

Zhang et al., *J. Comput. Aided Mol. Des.*, 21:97-112, 2007.

Zhang, *Methods Mol. Biol.*, 716:23-38, 2011.

Zheng et al., *Mol. Cell*, 10:1519-1526, 2002a.

Zheng et al., *Nature*, 416:703-709, 2002b.

The invention claimed is:

1. A method of treating a cancer, wherein the cancer exhibits misregulation of Skp2, comprising administering to a subject an effective amount of a compound having the structure:

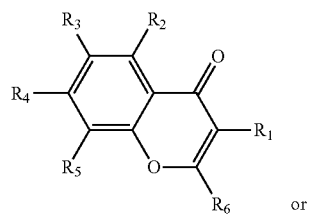 or

-continued

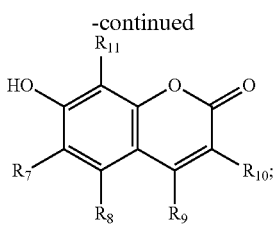

wherein
R₁ and R₁₀ are heteroaryl$_{(C\leq18)}$ or substituted heteroaryl$_{(C\leq18)}$;
R₂, R₄, R₇, R₈, and R₉ are each independently selected from the group consisting of hydrogen, alkyl$_{(C\leq18)}$, substituted alkyl$_{(C\leq18)}$, heteroaryl$_{(C\leq18)}$, substituted heteroaryl$_{(C\leq18)}$, heterocycloalkyl$_{(C\leq18)}$, substituted heterocycloalkyl$_{(C\leq18)}$, acyl$_{(C\leq18)}$, -alkyl$_{(C\leq12)}$-heterocycloalkyl$_{(C\leq18)}$, aryl$_{(C\leq18)}$, OH, SH, CF₃,

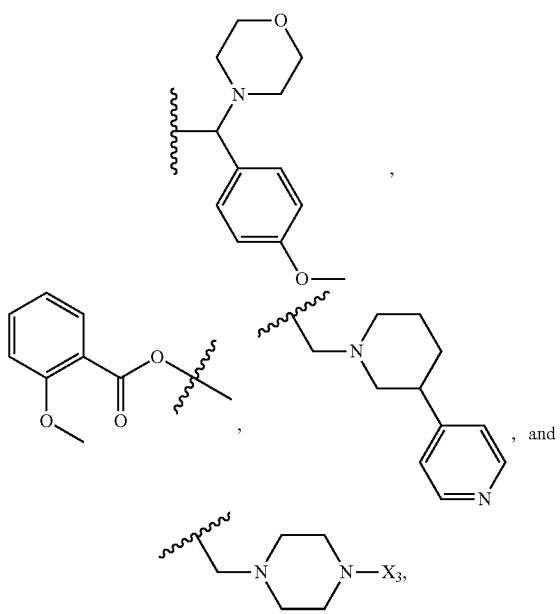

R₃ is alkyl$_{(C\leq18)}$ or substituted alkyl$_{(C\leq18)}$;
X₃ is alkyl$_{(C\leq12)}$ or substituted alkyl$_{(C\leq12)}$;
R₆ is selected from the group consisting of —H, alkyl$_{(C\leq18)}$, —NH₂, —C(O)Oalkyl$_{(C\leq18)}$, and substituted alkyl$_{(C\leq18)}$;
R₅ a is —CH₂—Y₂; wherein Y₂ is selected from the group consisting of —N(CH₃)₂,

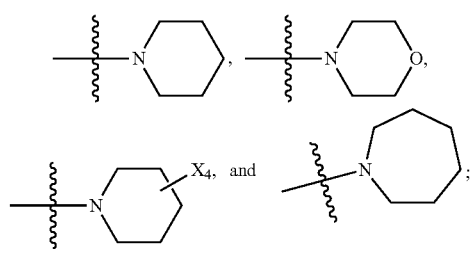

wherein X₄ is alkyl$_{(C1-12)}$;
R₁₁ is —CH₂—Y₂; wherein Y₂ is selected from the group consisting of —N(CH₃)₂,

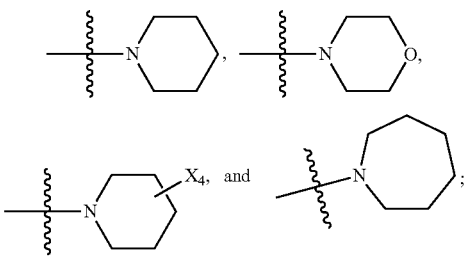

wherein X₄ is alkyl$_{(C1-12)}$ or
a compound of the formula:

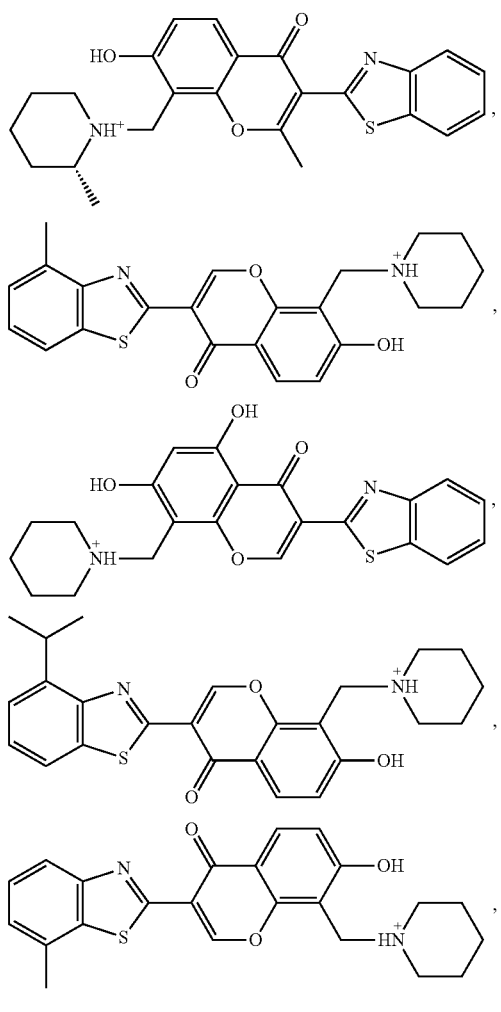

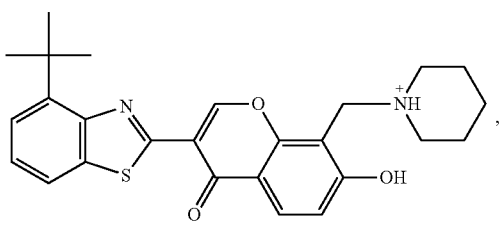

-continued
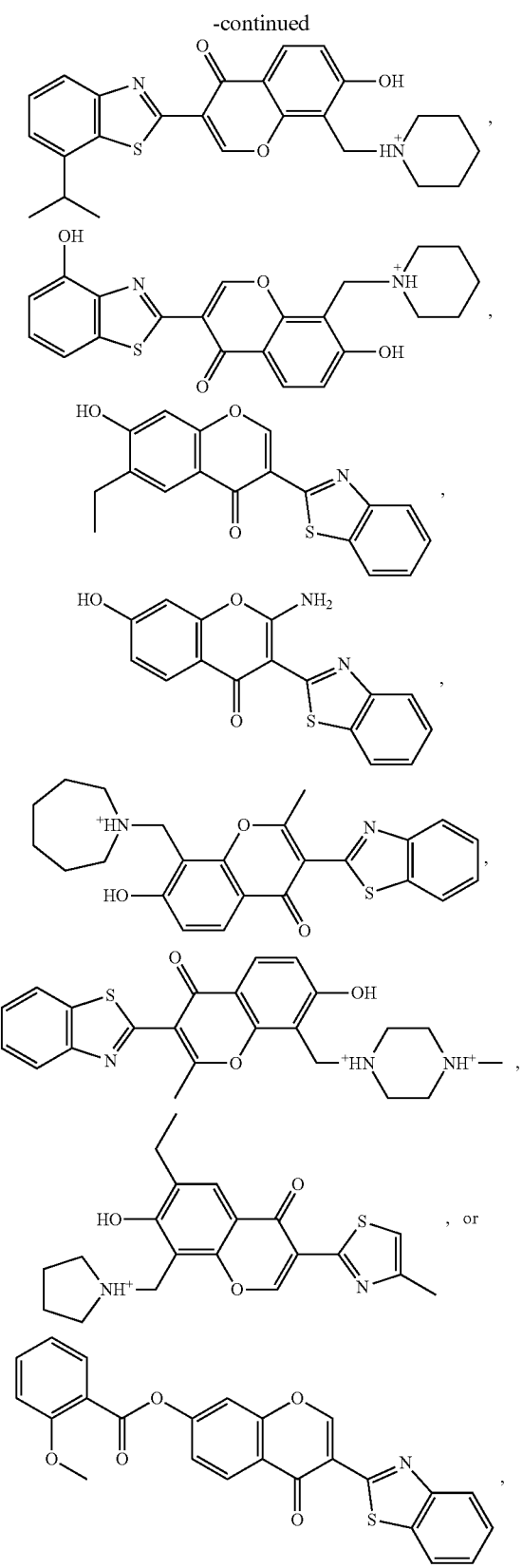
or a pharmaceutically acceptable salt or tautomer thereof.
2. The method of claim 1, wherein the compound has the structure
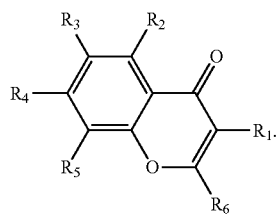
3. The method of claim 2, wherein the compound is selected from the group consisting of
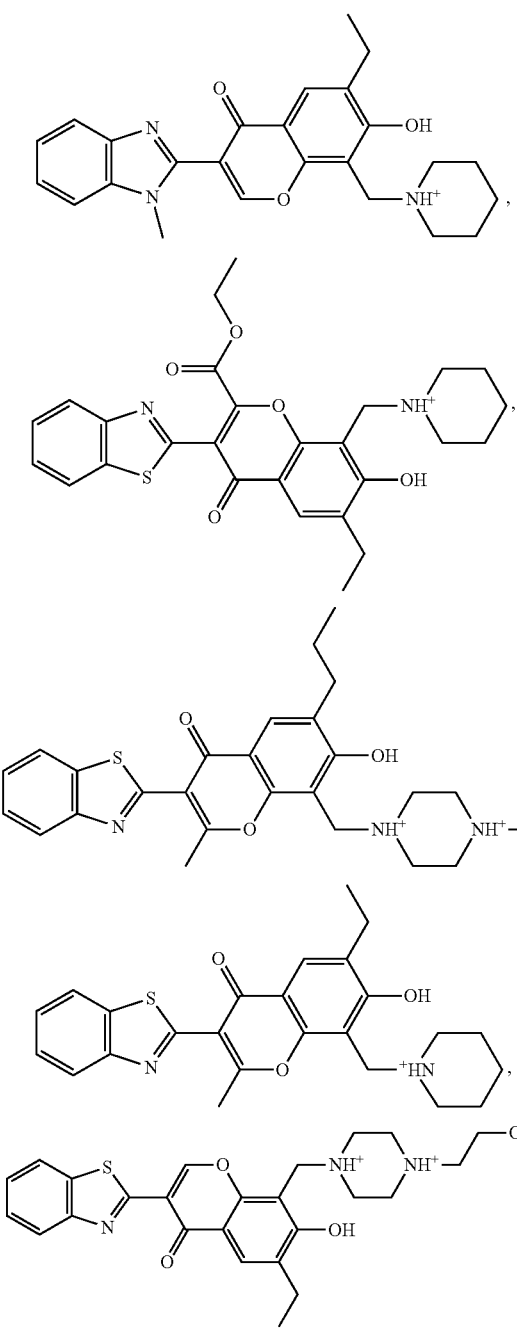

-continued
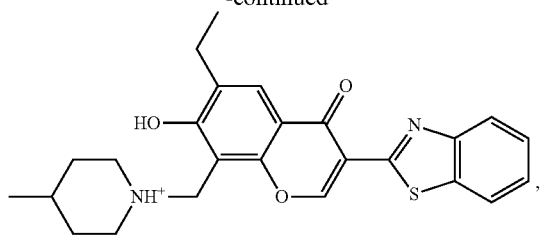
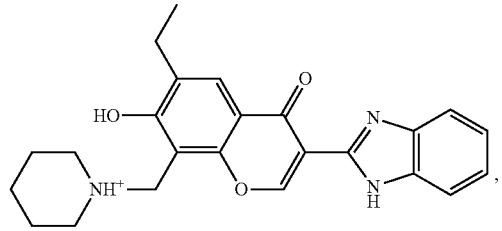
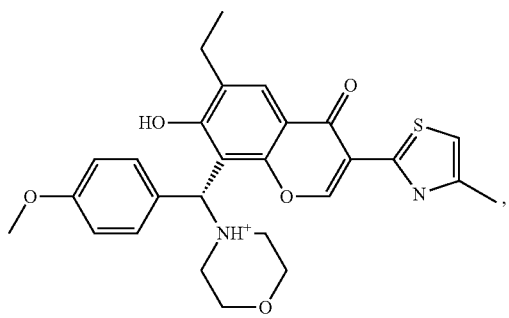
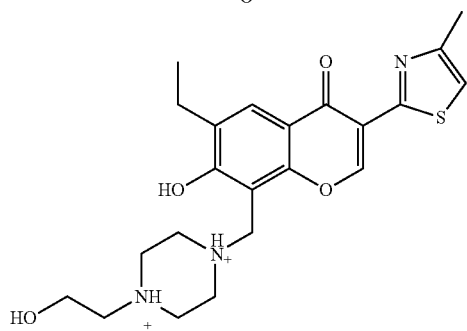
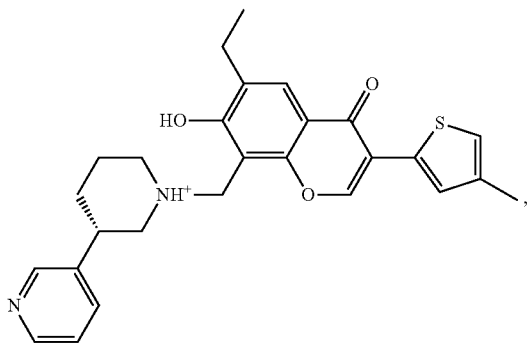
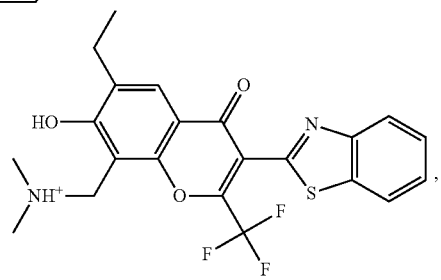
-continued
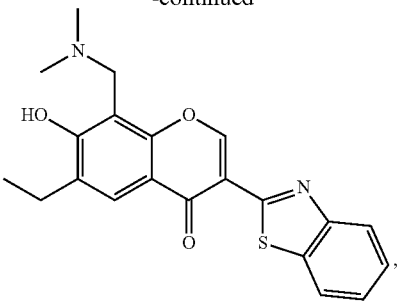
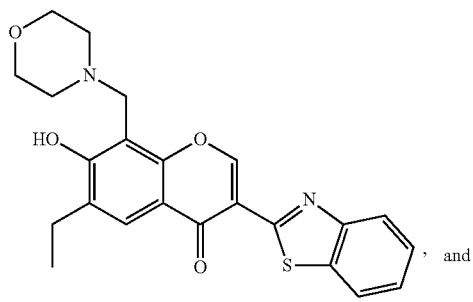
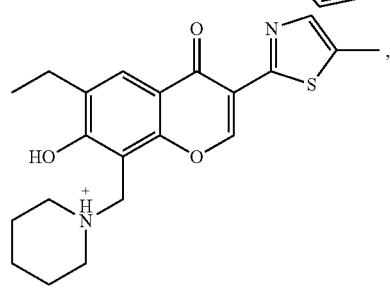
or a pharmaceutically acceptable salt thereof.
4. The method of claim 1, wherein $R_1$ is heteroaryl$_{(C \leq 12)}$.
5. The method of claim 1, wherein the compound has the structure:
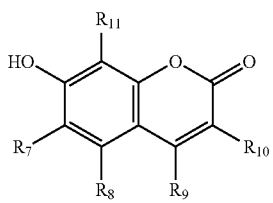
or a pharmaceutically acceptable salt or tautomer thereof.
6. The method of claim 5, wherein the compound has the structure
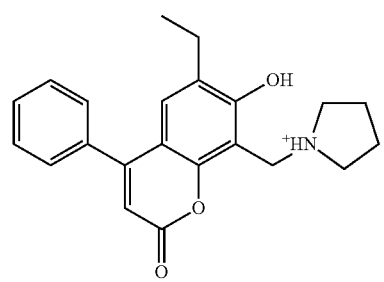
,

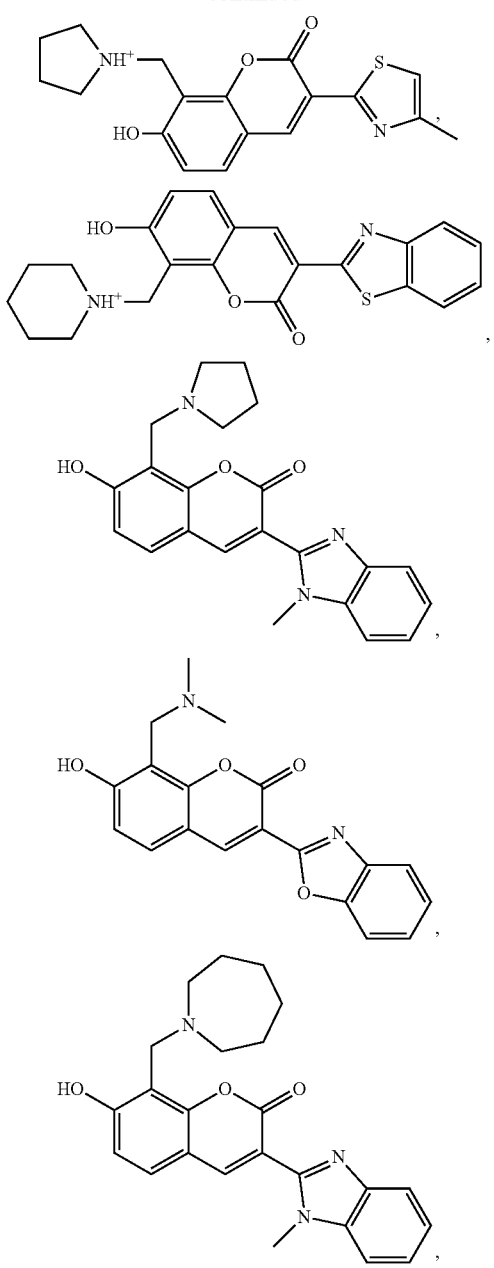

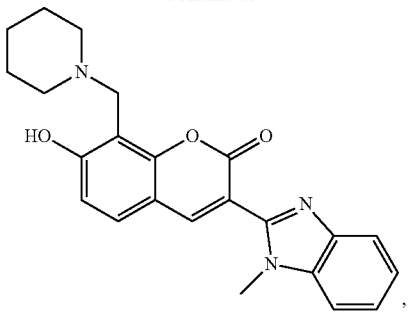 [SMILES: Cn1c(-c2cc3ccc(O)c(CN4CCCCC4)c3oc2=O)nc2ccccc21]

or a pharmaceutically acceptable salt thereof.

7. The method of claim 1, wherein the subject is a mammal.

8. The method of claim 1, wherein the cancer is a lymphoma, lung cancer, breast cancer, prostate cancer, liver cancer, or osteosarcoma.

9. The method of claim 1, further comprising administering an additional anticancer therapy to the subject.

10. The method of claim 1, wherein the composition is administered to the patient intravenously, intraperitoneally, intratracheally, intratumorally, intramuscularly, endoscopically, intralesionally, percutaneously, subcutaneously, regionally, or by direct injection or perfusion.

11. A method of culturing a cell, comprising contacting a plurality of cells in vitro with an amount of a compound of claim 1 effective to reduce differentiation, maintain an amount of dedifferentiation, or maintain a substantially dedifferentiated state in the cells; wherein the cells are pluripotent, multipotent, or totipotent.

12. The method of claim 1, wherein the cancer exhibits overexpression of Skp2.

13. A pharmaceutical composition comprising the compound of claim 1 and a pharmaceutically acceptable carrier or excipient.

14. A compound of the formula:

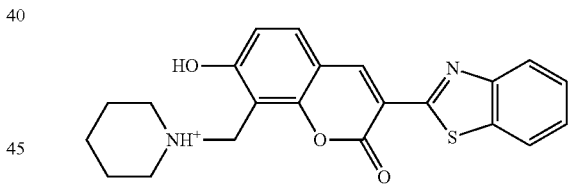

or a pharmaceutical salt thereof.

* * * * *

UNITED STATES PATENT AND TRADEMARK OFFICE
CERTIFICATE OF CORRECTION

PATENT NO. : 9,624,211 B2
APPLICATION NO. : 14/905726
DATED : April 18, 2017
INVENTOR(S) : Shuxing Zhang et al.

Page 1 of 2

It is certified that error appears in the above-identified patent and that said Letters Patent is hereby corrected as shown below:

In Claim 1, Column 81, Line 18, after "acyl$_{(C\leq18)}$," insert -- –C(O)O-alkyl$_{(C\leq18)}$, --.

In Claim 3, Column 84, Line 15, insert missing chemical drawing:

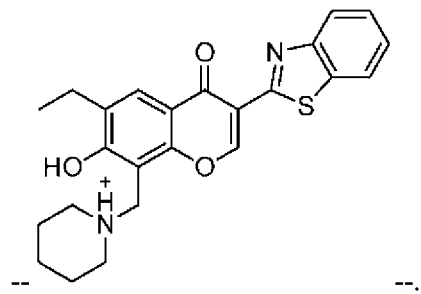

--.

In Claim 3, Column 85, Lines 19-30, delete chemical drawing and insert:

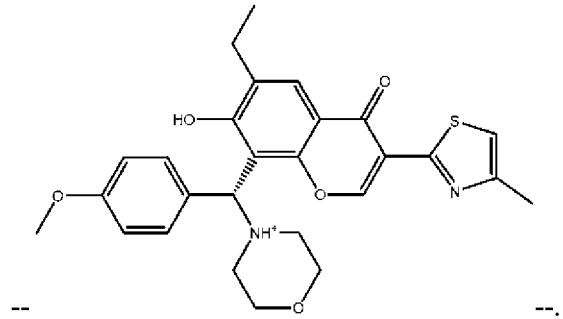

--.

Signed and Sealed this
Twenty-ninth Day of August, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,624,211 B2

In Claim 3, Column 85, Lines 44-56, delete chemical drawing and insert:

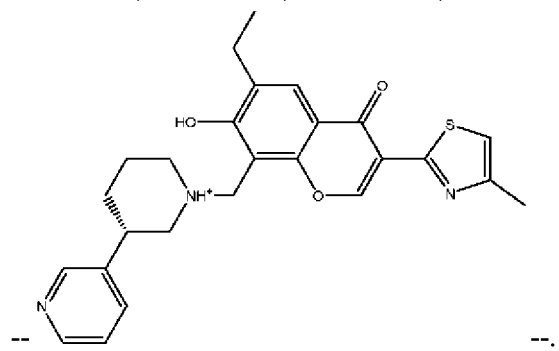

--.